United States Patent
Cassayre et al.

(10) Patent No.: US 7,807,679 B2
(45) Date of Patent: Oct. 5, 2010

(54) PIPERAZINE DERIVATIVES AND THEIR USE IN CONTROLLING PESTS

(75) Inventors: Jérôme Cassayre, Basel (CH); Peter Maienfisch, Basel (CH); Fredrik Cederbaum, Basel (CH); Louis-Pierre Molleyres, Basel (CH); Camilla Corsi, Basel (CH); Thomas Pitterna, Basel (CH)

(73) Assignee: Syngenta Crop Protection, Inc., Greensboro, NC (US)

( * ) Notice: Subject to any disclaimer, the term of this patent is extended or adjusted under 35 U.S.C. 154(b) by 615 days.

(21) Appl. No.: 11/569,006

(22) PCT Filed: May 12, 2005

(86) PCT No.: PCT/IB2005/001468

§ 371 (c)(1),
(2), (4) Date: Jul. 26, 2007

(87) PCT Pub. No.: WO2005/115146

PCT Pub. Date: Dec. 5, 2008

(65) Prior Publication Data

US 2008/0076777 A1    Mar. 27, 2008

(30) Foreign Application Priority Data

May 28, 2004  (GB) ................... 0412072.1

(51) Int. Cl.
*A01N 43/60* (2006.01)
*C07D 401/00* (2006.01)
(52) U.S. Cl. .................. 514/252.12; 514/253.01; 424/405; 544/358; 544/359; 544/360
(58) Field of Classification Search ............ 514/252.12, 514/253.01; 544/358, 359, 360
See application file for complete search history.

(56) References Cited

U.S. PATENT DOCUMENTS 3,457,263 A    7/1969    Regnier et al

FOREIGN PATENT DOCUMENTS

| EP | 0103464 A2 | 3/1984 |
| WO | 0242310 A2 | 5/2002 |
| WO | 2004089905 A1 | 10/2004 |

OTHER PUBLICATIONS

Kinnamon et al. ("Polyamines: agents with macrofilaricidal activity" Annals of Tropical Medicine & Parasitology, 93 (8), 1999, 851-858).*
Guillaumel, J. et al, "Synthesis of bis-heteroaryl piperazine derivatives as potential reverse transcriptase ihibitors". J. Heterocyclic Chem., vol. 38, pp. 985-988, compounds 5A-6G, 2001.

* cited by examiner

*Primary Examiner*—Sharmila Gollamudi Landau
*Assistant Examiner*—Kortney L Klinkel
(74) *Attorney, Agent, or Firm*—William A. Teoli, Jr.

(57) ABSTRACT

The use of a compound of formula (I) wherein Y is a single bond, C=O, C=S or $S(O)_m$ where m is 0, 1 or 2; the ring is a 6-membered aromatic or is a 5 or 6 membered heteroaromatic ring; Ra, $R^1$, $R^2$, $R^4$ and $R^8$ are specified organic groups; n and p are independently 0-4; or salts or N-oxides thereof or compositions containing them in controlling insects, acarines, nematodes or molluscs. Novel compounds are also provided.

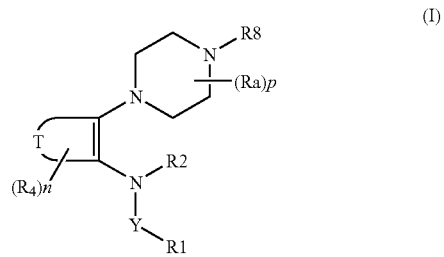

14 Claims, No Drawings

PIPERAZINE DERIVATIVES AND THEIR USE IN CONTROLLING PESTS

This application is a 371 of International Application No. PCT/IB2005/001468 filed May 12, 2005, which claims priority to GB 0412072.1 filed May 28, 2004, the contents of which are incorporated herein by reference.

The present invention relates to piperazine derivatives, to processes for preparing them, to insecticidal, acaricidal, molluscicidal and nematicidal compositions comprising them and to methods of using them to combat and control insect, acarine, mollusc and nematode pests.

piperazine derivatives with antiprotazoal properties are disclosed in for example in US 331,845 and EP103464 discloses pyrimidinyl piperazine compounds with antibacterial properties.

It has now surprisingly been found that certain piperazines have insecticidal properties.

The present invention therefore provides a method of combating and controlling insects, acarines, nematodes or molluscs which comprises applying to a pest, to a locus of a pest, or to a plant susceptible to attack by a pest an insecticidally, acaricidally, nematicidally or molluscicidally effective amount of a compound of formula (I):

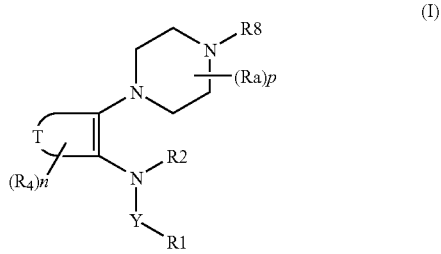

Y is a single bond, C=O, C=S or S(O)$_m$ where m is 0, 1 or 2; the ring

is a 6 membered aromatic ring or is a 5 or 6 membered heteroaromatic ring;

$R^1$ is hydrogen, optionally substituted alkyl, optionally substituted alkoxycarbonyl, optionally substituted alkylcarbonyl, aminocarbonyl, optionally substituted alkylaminocarbonyl, optionally substituted dialkylaminocarbonyl, optionally substituted aryl, optionally substituted heteroaryl, optionally substituted alkoxy, optionally substituted aryloxy, optionally substituted heteroaryloxy, optionally substituted heterocyclyloxy, cyano, optionally substituted alkenyl, optionally substituted alkynyl, optionally substituted cycloalkyl, optionally substituted cycloalkenyl, formyl, optionally substituted heterocyclyl, optionally substituted alkylthio, NO or NR$^{13}$R$^{14}$ where R$^{13}$ and R$^{14}$ are independently hydrogen, COR$^{15}$, optionally substituted alkyl, optionally substituted aryl, optionally substituted heteroaryl, optionally substituted heterocyclyl or R$^{13}$ and R$^{14}$ together with the N atom to which they are attached form a group —N=C(R$^{16}$)—NR$^{17}$R$^{18}$ or R$^{13}$ and R$^{14}$ together with the N atom to which they are attached form a five, six or seven-membered heterocyclic ring which may contain one or two further heteroatoms selected from O, N or S and which may be optionally substituted by one or two C$_{1-6}$ alkyl groups; R$^{15}$ is H, optionally substituted alkyl, optionally substituted alkoxy, optionally substituted aryl, optionally substituted aryloxy optionally substituted heteroaryl, optionally substituted heteroaryloxy or NR$^{19}$R$^{20}$; R$^{16}$, R$^{17}$ and R$^{18}$ are each independently H or lower alkyl; R$^{19}$ and R$^{20}$ are independently optionally substituted alkyl, optionally substituted aryl or optionally substituted heteroaryl;

$R^2$ is H, hydroxy, optionally substituted alkoxy or optionally substituted alkyl; or R$^1$ and R$^2$ together with the groups Y and N form a 5- or 6-membered heterocyclic ring which may optionally contain one further heteroatom selected from O, N or S and which may be optionally substituted by C$_{1-4}$ alkyl, C$_{1-4}$ haloalkyl or halogen;

each R$^4$ is independently halogen, nitro, cyano, optionally substituted C$_{1-8}$ alkyl, optionally substituted C$_{2-6}$ alkenyl, optionally substituted C$_{2-6}$ alkynyl, optionally substituted alkoxycarbonyl, optionally substituted alkylcarbonyl, optionally substituted alkylaminocarbonyl, optionally substituted dialkylaminocarbonyl, optionally substituted C$_{3-7}$ cycloalkyl, optionally substituted aryl, optionally substituted heteroaryl, optionally substituted heterocyclyl, optionally substituted alkoxy, optionally substituted aryloxy, optionally substituted heteroaryloxy, optionally substituted alkylthio or R$^{21}$R$^{22}$N where R$^{21}$ and R$^{22}$ are, independently, hydrogen, C$_{1-8}$ alkyl, C$_{3-7}$ cycloalkyl, C$_{3-6}$ alkenyl, C$_{3-6}$ alkynyl, C$_{3-7}$ cycloalkyl(C$_{1-4}$)alkyl, C$_{2-6}$ haloalkyl, C$_{1-6}$ alkoxy(C$_{1-6}$)alkyl, C$_{1-6}$ alkoxycarbonyl or R$^{21}$ and R$^{22}$ together with the N atom to which they are attached form a five, six or seven-membered heterocyclic ring which may contain one or two further heteroatoms selected from O, N or S and which may be optionally substituted by one or two C$_{1-6}$ alkyl groups, or 2 adjacent groups R$^4$ together with the carbon atoms to which they are attached form a 4, 5, 6, or 7 membered carbocyclic or heterocyclic ring which may be optionally substituted by halogen; n is 0, 1, 2, 3 or 4;

$R^8$ is optionally substituted alkyl, optionally substituted alkenyl, optionally substituted alkynyl, optionally substituted cycloalkyl, optionally substituted aryl, optionally substituted alkoxy, optionally substituted aryloxy, optionally substituted alkoxycarbonyl, optionally substituted alkylcarbonyl or optionally substituted alkenylcarbonyl;

each Ra is independently halogen, hydroxy, cyano, optionally substituted C$_{1-8}$ alkyl, optionally substituted C$_{2-6}$ alkenyl, optionally substituted C$_{2-6}$ alkynyl, optionally substituted alkoxycarbonyl, optionally substituted alkylcarbonyl, optionally substituted alkylaminocarbonyl, optionally substituted dialkylaminocarbonyl, optionally substituted C$_{3-7}$ cycloalkyl, optionally substituted aryl, optionally substituted heteroaryl, optionally substituted heterocyclyl, optionally substituted alkoxy, optionally substituted aryloxy, optionally substituted heteroaryloxy, optionally substituted alkylthio, optionally substituted arylthio or R$^{23}$R$^{24}$N where R$^{23}$ and R$^{24}$ are, independently, hydrogen, C$_{1-8}$ alkyl, C$_{3-7}$ cycloalkyl, C$_{3-6}$ alkenyl, C$_{3-6}$ alkynyl, C$_{3-7}$ cycloalkyl(C$_{1-4}$)alkyl, C$_{2-6}$ haloalkyl, C$_{1-6}$ alkoxy(C$_{1-6}$)alkyl, C$_{1-6}$ alkoxycarbonyl or R$^{23}$ and R$^{24}$ together with the N atom to which they are attached form a five, six or seven-membered heterocyclic ring which may contain one or two further heteroatoms selected from O, N or S and which may be optionally substituted by one or two C$_{1-6}$ alkyl groups, or two Ra groups attached to the same carbon atom are =O, =S, =NRb, =CRcRd where Rb, Rc and Rd are independently H or optionally substituted alkyl; p is 0, 1, 2, 3 or 4 or salts or N-oxides thereof.

The compounds of formula (I) may exist in different geometric or optical isomers or tautomeric forms. This invention covers all such isomers and tautomers and mixtures thereof in all proportions as well as isotopic forms such as deuterated compounds.

Each alkyl moiety either alone or as part of a larger group (such as alkoxy, alkoxycarbonyl, alkylcarbonyl, alkylaminocarbonyl, dialkylaminocarbonyl) is a straight or branched chain and is, for example, methyl, ethyl, n-propyl, n-butyl, n-pentyl, n-hexyl, iso-propyl, n-butyl, sec-butyl, iso-butyl, tert-butyl or neo-pentyl. The alkyl groups are suitably $C_1$ to $C_{12}$ alkyl groups, but are preferably $C_1$-$C_{10}$, more preferably $C_1$-$C_8$, even more preferably $C_1$-$C_6$ and most preferably $C_1$-$C_4$ alkyl groups.

When present, the optional substituents on an alkyl moiety (alone or as part of a larger group such as alkoxy, alkoxycarbonyl, alkylcarbonyl, alkylaminocarbonyl, dialkylaminocarbonyl) include one or more of halogen, nitro, cyano, NCS—, $C_{3-7}$ cycloalkyl (itself optionally substituted with $C_{1-6}$ alkyl or halogen), $C_{5-7}$ cycloalkenyl (itself optionally substituted with $C_{1-6}$ alkyl or halogen), hydroxy, $C_{1-10}$ alkoxy, $C_{1-10}$ alkoxy($C_{1-10}$)alkoxy, tri($C_{1-4}$)alkylsilyl($C_{1-6}$)alkoxy, $C_{1-6}$ alkoxycarbonyl($C_{1-10}$)alkoxy, $C_{1-10}$ haloalkoxy, aryl($C_{1-14}$)-alkoxy (where the aryl group is optionally substituted), $C_{3-7}$ cycloalkyloxy (where the cycloalkyl group is optionally substituted with $C_{1-6}$ alkyl or halogen), $C_{2-10}$ alkenyloxy, $C_{2-10}$ alkynyloxy, SH, $C_{1-10}$ alkylthio, $C_{1-10}$ haloalkylthio, aryl($C_{1-4}$)alkylthio (where the aryl group is optionally substituted), $C_{3-7}$ cycloalkylthio (where the cycloalkyl group is optionally substituted with $C_{1-6}$ alkyl or halogen), tri($C_{1-4}$)alkylsilyl($C_{1-6}$)alkylthio, arylthio (where the aryl group is optionally substituted), $C_{1-6}$ alkylsulfonyl, $C_{1-6}$ haloalkylsulfonyl, $C_{1-6}$ alkylsulfinyl, $C_{1-6}$ haloalkylsulfinyl, arylsulfonyl (where the aryl group may be optionally substituted), tri($C_{1-4}$)alkylsilyl, aryldi($C_{1-4}$)alkylsilyl, ($C_{1-4}$)alkyldiarylsilyl, triarylsilyl, $C_{1-10}$ alkylcarbonyl, $HO_2C$, $C_{1-10}$ alkoxycarbonyl, aminocarbonyl, $C_{1-6}$ alkylaminocarbonyl, di($C_{1-6}$ alkyl) aminocarbonyl, N—($C_{1-3}$ alkyl)-N—($C_{1-3}$ alkoxy)aminocarbonyl, $C_{1-6}$ alkylcarbonyloxy, arylcarbonyloxy (where the aryl group is optionally substituted), di($C_{1-6}$)alkylaminocarbonyloxy, oximes such as =NOalkyl, =NOhaloalkyl and =NOaryl (itself optionally substituted), aryl (itself optionally substituted), heteroaryl (itself optionally substituted), heterocyclyl (itself optionally substituted with $C_{1-6}$ alkyl or halogen), aryloxy (where the aryl group is optionally substituted), heteroaryloxy, (where the heteroaryl group is optionally substituted), heterocyclyloxy (where the heterocyclyl group is optionally substituted with $C_{1-6}$ alkyl or halogen), amino, $C_{1-6}$ alkylamino, di($C_{1-6}$)alkylamino, $C_{1-6}$ alkylcarbonylamino, N—($C_{1-6}$)alkylcarbonyl-N—($C_{1-6}$)alkylamino, $C_{2-6}$ alkenylcarbonyl, $C_{2-6}$ alkynylcarbonyl, $C_{3-6}$ alkenyloxycarbonyl, $C_{3-6}$ alkynyloxycarbonyl, aryloxycarbonyl (where the aryl group is optionally substituted) and arylcarbonyl (where the aryl group is optionally substituted).

Alkenyl and alkynyl moieties can be in the form of straight or branched chains, and the alkenyl moieties, where appropriate, can be of either the (E)- or (Z)-configuration. Examples are vinyl, allyl and propargyl.

When present, the optional substituents on alkenyl or alkynyl include those optional substituents given above for an alkyl moiety.

In the context of this specification acyl is optionally substituted $C_{1-6}$ alkylcarbonyl (for example acetyl), optionally substituted $C_{2-6}$ alkenylcarbonyl, optionally substituted $C_{2-6}$ alkynylcarbonyl, optionally substituted arylcarbonyl (for example benzoyl) or optionally substituted heteroarylcarbonyl.

Halogen is fluorine, chlorine, bromine or iodine.

Haloalkyl groups are alkyl groups which are substituted with one or more of the same or different halogen atoms and are, for example, $CF_3$, $CF_2C_1$, $CF_3CH_2$ or $CHF_2CH_2$.

In the context of the present specification the terms "aryl", "aromatic ring" and "aromatic ring system" refer to ring systems which may be mono-, bi- or tricyclic. Examples of such rings include phenyl, naphthalenyl, anthracenyl, indenyl or phenanthrenyl. A preferred aryl group is phenyl. In addition, the terms "heteroaryl", "heteroaromatic ring" or "heteroaromatic ring system" refer to an aromatic ring system containing at least one heteroatom and consisting either of a single ring or of two or more fused rings. Preferably, single rings will contain up to three and bicyclic systems up to four heteroatoms which will preferably be chosen from nitrogen, oxygen and sulphur. Examples of such groups include furyl, thienyl, pyrrolyl, pyrazolyl, imidazolyl, 1,2,3-triazolyl, 1,2,4-triazolyl, oxazolyl, isoxazolyl, thiazolyl, isothiazolyl, 1,2,3-oxadiazolyl, 1,2,4-oxadiazolyl, 1,3,4-oxadiazolyl, 1,2,5-oxadiazolyl, 1,2,3-thiadiazolyl, 1,2,4-thiadiazolyl, 1,3,4-thiadiazolyl, 1,2,5-thiadiazolyl, pyridyl, pyrimidinyl, pyridazinyl, pyrazinyl, 1,2,3-triazinyl, 1,2,4-triazinyl, 1,3,5-triazinyl, benzofuryl, benzisofuryl, benzothienyl, benzisothienyl, indolyl, isoindolyl, indazolyl, benzothiazolyl, benzisothiazolyl, benzoxazolyl, benzisoxazolyl, benzimidazolyl, 2,1,3-benzoxadiazole quinolinyl, isoquinolinyl, cinnolinyl, phthalazinyl, quinazolinyl, quinoxalinyl, naphthyridinyl, benzotriazinyl, purinyl, pteridinyl and indolizinyl. Preferred examples of heteroaromatic radicals include pyridyl, pyrimidyl, triazinyl, thienyl, furyl, oxazolyl, isoxazolyl, 2,1,3-benzoxadiazole and thiazolyl.

The terms heterocycle and heterocyclyl refer to a non-aromatic ring containing up to 10 atoms including one or more (preferably one or two) heteroatoms selected from O, S and N. Examples of such rings include 1,3-dioxolane, tetrahydrofuran and morpholine.

When present, the optional substituents on heterocyclyl include $C_{1-6}$ alkyl and $C_{1-6}$ haloalkyl as well as those optional substituents given above for an alkyl moiety.

Cycloalkyl includes cyclopropyl, cyclopentyl and cyclohexyl.

Cycloalkenyl includes cyclopentenyl and cyclohexenyl.

When present, the optional substituents on cycloalkyl or cycloalkenyl include $C_{1-3}$ alkyl as well as those optional substituents given above for an alkyl moiety.

Carbocyclic rings include aryl, cycloalkyl and cycloalkenyl groups.

When present, the optional substituents on aryl or heteroaryl are selected independently, from halogen, nitro, cyano, NCS—, $C_{1-6}$ alkyl, $C_{1-6}$ haloalkyl, $C_{1-6}$ alkoxy-($C_{1-6}$) alkyl, $C_{2-6}$ alkenyl, $C_{2-6}$ haloalkenyl, $C_{2-6}$ alkynyl, $C_{3-7}$ cycloalkyl (itself optionally substituted with $C_{1-6}$ alkyl or halogen), $C_{5-7}$ cycloalkenyl (itself optionally substituted with $C_{1-6}$ alkyl or halogen), hydroxy, $C_{1-10}$ alkoxy, $C_{1-10}$ alkoxy($C_{1-10}$)alkoxy, tri($C_{1-4}$)alkyl-silyl($C_{1-6}$)alkoxy, $C_{1-6}$ alkoxycarbonyl($C_{1-10}$)alkoxy, $C_{1-10}$ haloalkoxy, aryl($C_{1-4}$)alkoxy (where the aryl group is optionally substituted with halogen or $C_{1-6}$ alkyl), $C_{3-7}$ cycloalkyloxy (where the cycloalkyl group is optionally substituted with $C_{1-6}$ alkyl or halogen), $C_{2-10}$ alkenyloxy, $C_{2-10}$ alkynyloxy, SH, $C_{1-10}$ alkylthio, $C_{1-10}$ haloalkylthio, aryl($C_{1-4}$)alkylthio $C_{3-7}$ cycloalkylthio (where the cycloalkyl group is optionally substituted with $C_{1-6}$ alkyl or halogen), tri($C_{1-4}$)-alkylsilyl($C_{1-6}$)alkylthio, arylthio, $C_{1-6}$ alkylsulfonyl, $C_{1-6}$ haloalkylsulfonyl, $C_{1-6}$ alkylsulfinyl, $C_{1-6}$ haloalkylsulfinyl, arylsulfonyl, tri($C_{1-4}$)alkylsilyl, aryldi($C_{1-4}$)-alkylsilyl, ($C_{1-4}$)alkyldiarylsilyl, triarylsilyl, $C_{1-10}$ alkylcarbonyl, $HO_2C$, $C_{1-10}$ alkoxycarbonyl, aminocarbonyl, $C_{1-6}$ alkylaminocarbonyl, di($C_{1-6}$ alkyl)-aminocarbonyl, N—($C_{1-3}$ alkyl)-N—($C_{1-3}$ alkoxy)aminocarbonyl, $C_{1-6}$ alkylcarbonyloxy, arylcarbonyloxy, di($C_{1-6}$)alkylamino-carbonyloxy, aryl (itself optionally substituted with $C_{1-6}$ alkyl or halogen), heteroaryl (itself optionally substituted with $C_{1-6}$ alkyl or halogen), heterocyclyl (itself optionally substituted with $C_{1-6}$ alkyl or halogen), aryloxy (where the aryl group is optionally substituted with $C_{1-6}$ alkyl or halogen), heteroaryloxy (where the heteroaryl group is optionally substituted with $C_{1-6}$ alkyl or halogen), heterocyclyloxy (where the heterocyclyl group is optionally substituted with $C_{1-6}$ alkyl or halogen), amino, $C_{1-6}$ alkylamino, di($C_{1-6}$) alkylamino, $C_{1-6}$ alkylcarbonylamino, N—($C_{1-6}$)alkylcarbonyl-N—($C_{1-6}$) alkylamino, arylcarbonyl, (where the aryl group is itself optionally substituted with halogen or $C_{1-6}$ alkyl) or two adjacent positions on an aryl or heteroaryl system may be cyclised to form a 5, 6 or 7 membered carbocyclic or heterocyclic ring, itself optionally substituted with halogen or $C_{1-6}$ alkyl. Further substituents for aryl or heteroaryl include aryl carbonyl amino (where the aryl group is substituted by $C_{1-6}$ alkyl or halogen), ($C_{1-6}$)alkyloxycarbonylamino ($C_{1-6}$)alkyloxycarbonyl-N—($C_{1-6}$)alkylamino, aryloxycarbonylamino (where the aryl group is substituted by $C_{1-6}$ alkyl or halogen), aryloxycarbonyl-N—($C_{1-6}$)alkylamino, (where the aryl group is substituted by $C_{1-6}$ alkyl or halogen), arylsulphonylamino (where the aryl group is substituted by $C_{1-6}$ alkyl or halogen), arylsulphonyl-N—($C_{1-6}$)alkylamino (where the aryl group is substituted by $C_{1-6}$ alkyl or halogen), aryl-N—($C_{1-6}$)alkylamino (where the aryl group is substituted by $C_{1-6}$ alkyl or halogen), arylamino (where the aryl group is substituted by $C_{1-6}$ alkyl or halogen), heteroaryl amino (where the heteroaryl group is substituted by $C_{1-6}$ alkyl or halogen), heterocyclylamino (where the heterocyclyl group is substituted by $C_{1-6}$ alkyl or halogen), aminocarbonylamino, $C_{1-6}$ alkylaminocarbonyl amino, di($C_{1-6}$)alkylaminocarbonyl amino, arylaminocarbonyl amino where the aryl group is substituted by $C_{1-6}$ alkyl or halogen), aryl-N—($C_{1-6}$)alkylaminocarbonylamino where the aryl group is substituted by $C_{1-6}$ alkyl or halogen), $C_{1-6}$ alkylaminocarbonyl-N—($C_{1-6}$) alkyl amino, di($C_{1-6}$)alkylaminocarbonyl-N—($C_{1-6}$)alkyl amino, arylaminocarbonyl-N—($C_{1-6}$)alkyl amino where the aryl group is substituted by $C_{1-6}$ alkyl or halogen) and aryl-N—($C_{1-6}$)alkylaminocarbonyl-N—($C_{1-6}$)alkyl amino where the aryl group is substituted by $C_{1-6}$ alkyl or halogen).

For substituted phenyl moieties, heterocyclyl and heteroaryl groups it is preferred that one or more substituents are independently selected from halogen, $C_{1-6}$ alkyl, $C_{1-6}$ haloalkyl, $C_{1-6}$ alkoxy($C_{1-6}$)alkyl, $C_{1-6}$ alkoxy, $C_{1-6}$ haloalkoxy, $C_{1-6}$ alkylthio, $C_{1-6}$ haloalkylthio, $C_{1-6}$ alkylsulfinyl, $C_{1-6}$ haloalkylsulfinyl, $C_{1-6}$ alkylsulfonyl, $C_{1-6}$ haloalkylsulfonyl, $C_{2-6}$ alkenyl, $C_{2-6}$ haloalkenyl, $C_{2-6}$ alkynyl, $C_{3-7}$ cycloalkyl, nitro, cyano, $CO_2H$, $C_{1-6}$ alkylcarbonyl, $C_{1-6}$ alkoxycarbonyl, $R^{25}R^{26}N$ or $R^{27}R^{28}NC(O)$; wherein $R^{25}$, $R^{26}$, $R^{27}$ and $R^{28}$ are, independently, hydrogen or $C_{1-6}$ alkyl. Further preferred substituents are aryl and heteroaryl groups.

Haloalkenyl groups are alkenyl groups which are substituted with one or more of the same or different halogen atoms.

It is to be understood that dialkylamino substituents include those where the dialkyl groups together with the N atom to which they are attached form a five, six or seven-membered heterocyclic ring which may contain one or two further heteroatoms selected from O, N or S and which is optionally substituted by one or two independently selected ($C_{1-6}$)alkyl groups. When heterocyclic rings are formed by joining two groups on an N atom, the resulting rings are suitably pyrrolidine, piperidine, thiomorpholine and morpholine each of which may be substituted by one or two independently selected ($C_{1-6}$) alkyl groups.

Preferably the optional substituents on an alkyl moiety include one or more of halogen, nitro, cyano, $HO_2C$, $C_{1-10}$ alkoxy (itself optionally substituted by $C_{1-10}$ alkoxy), aryl ($C_{1-4}$)alkoxy, $C_{1-10}$ alkylthio, $C_{1-10}$ alkylcarbonyl, $C_{1-10}$ alkoxycarbonyl, $C_{1-6}$ alkylaminocarbonyl, di($C_{1-6}$ alkyl)aminocarbonyl, ($C_{1-6}$)alkylcarbonyloxy, optionally substituted phenyl, heteroaryl, aryloxy, arylcarbonyloxy, heteroaryloxy, heterocyclyl, heterocyclyloxy, $C_{3-7}$ cycloalkyl (itself optionally substituted with ($C_{1-6}$)alkyl or halogen), $C_{3-7}$ cycloalkyloxy, $C_{5-7}$ cycloalkenyl, $C_{1-6}$ alkylsulfonyl, $C_{1-6}$ alkylsulfinyl, tri($C_{1-4}$)alkylsilyl, tri($C_{1-4}$)alkylsilyl($C_{1-6}$)alkoxy, aryldi($C_{1-4}$)alkylsilyl, ($C_{1-4}$)alkyldiarylsilyl and triarylsilyl.

Preferably the optional substituents on alkenyl or alkynyl include one or more of halogen, aryl and $C_{3-7}$ cycloalkyl.

A preferred optional substituent for heterocyclyl is $C_{1-6}$ alkyl.

Preferably the optional substituents for cycloalkyl include halogen, cyano and $C_{1-3}$ alkyl.

Preferably the optional substituents for cycloalkenyl include $C_{1-3}$ alkyl, halogen and cyano.

Preferred groups for T, Y, Ra, $R^1$, $R^2$, $R^4$ and $R^8$ in any combination thereof are set out below.

Preferably Y is a single bond, C═O or C═S.

More preferably Y is a single bond or C═O.

Most preferably Y is C═O.

Preferably $R^1$ is hydrogen, $C_{1-6}$ alkyl, $C_{1-6}$ cyanoalkyl, $C_{1-6}$ haloalkyl, $C_{3-7}$ cycloalkyl($C_{1-4}$)alkyl, $C_{1-6}$ alkoxy($C_{1-6}$)alkyl, heteroaryl($C_{1-6}$)alkyl (wherein the heteroaryl group may be optionally substituted by halo, nitro, cyano, $C_{1-6}$ alkyl, $C_{1-6}$ haloalkyl, $C_{1-6}$ alkoxy, $C_{1-6}$ haloalkoxy, $C_{1-6}$ alkylsulfonyl, $C_{1-6}$ alkylsulfinyl, $C_{1-6}$ alkylthio, $C_{1-6}$ alkoxycarbonyl, $C_{1-6}$ alkylcarbonylamino, arylcarbonyl, or two adjacent positions on the heteroaryl system may be cyclised to form a 5, 6 or 7 membered carbocyclic or heterocyclic ring, itself optionally substituted with halogen), aryl($C_{1-6}$)alkyl (wherein the aryl group may be optionally substituted by halo, nitro, cyano, $C_{1-6}$ alkyl, $C_{1-6}$ haloalkyl, $C_{1-6}$ alkoxy, $C_{1-6}$ haloalkoxy, $C_{1-6}$ alkylsulfonyl, $C_{1-6}$ alkylsulfinyl, $C_{1-6}$ alkylthio, $C_{1-6}$ alkoxycarbonyl, $C_{1-6}$ alkylcarbonylamino, arylcarbonyl, or two adjacent positions on the aryl system may be cyclised to form a 5, 6 or 7 membered carbocyclic or heterocyclic ring, itself optionally substituted with halogen), $C_{1-6}$ alkylcarbonylamino($C_{1-6}$)alkyl, aryl (which may be optionally substituted by halo, nitro, cyano, $C_{1-6}$ alkyl, $C_{1-6}$ haloalkyl, $C_{1-6}$ alkoxy, $C_{1-6}$ haloalkoxy, $C_{1-6}$ alkylsulfonyl, $C_{1-6}$ alkylsulfinyl, $C_{1-6}$ alkylthio, $C_{1-6}$ alkoxycarbonyl, $C_{1-6}$ alkylcarbonylamino, arylcarbonyl, or two adjacent positions on the aryl system may be cyclised to form a 5, 6 or 7 membered carbocyclic or heterocyclic ring, itself optionally substituted with halogen), heteroaryl (which may be optionally substituted by halo, nitro, cyano, $C_{1-6}$ alkyl, $C_{1-6}$ haloalkyl, $C_{1-6}$ alkoxy, $C_{1-6}$ haloalkoxy, $C_{1-6}$ alkylsulfonyl, $C_{1-6}$ alkylsulfinyl, $C_{1-6}$ alkylthio, $C_{1-6}$ alkoxycarbonyl, $C_{1-6}$ alkylcarbonylamino, arylcarbonyl, or two adjacent positions on the heteroaryl system may be cyclised to form a 5, 6 or 7 membered carbocyclic or heterocyclic ring, itself optionally substituted with halogen), $C_{1-6}$ alkoxy, $C_{1-6}$ haloalkoxy, phenoxy (wherein the phenyl group is optionally substituted by halogen, $C_{1-4}$ alkyl, $C_{1-4}$ alkoxy, $C_{1-4}$ haloalkyl, $C_{1-4}$ haloalkoxy, CN, $NO_2$, aryl, heteroaryl, amino or dialkylamino), heteroaryloxy (optionally substituted by halo, nitro, cyano, $C_{1-6}$ alkyl, $C_{1-6}$ haloalkyl, $C_{1-6}$ alkoxy or $C_{1-6}$ haloalkoxy), heterocyclyloxy (optionally substituted by halo, $C_{1-6}$ alkyl, $C_{1-6}$ haloalkyl, $C_{1-6}$ alkoxy or $C_{1-6}$ haloalkoxy), cyano, $C_{2-6}$ alkenyl, $C_{2-6}$ alkynyl, $C_{3-6}$ cycloalkyl, $C_{5-7}$ cycloalkenyl, heterocyclyl (optionally substituted by halo, nitro, cyano, $C_{1-6}$ alkyl, $C_{1-6}$ haloalkyl, $C_{1-6}$ alkoxy or $C_{1-6}$ haloalkoxy), $C_{1-6}$ alkylthio, $C_{1-6}$ haloalkylthio or $NR^{13}R^{14}$ where $R^{13}$ and $R^{14}$ are independently hydrogen, $C_{1-6}$ alkyl, $C_{1-6}$ haloalkyl, $C_{1-6}$ alkoxy($C_{1-6}$) alkyl, phenyl (which may be optionally substituted by halogen, $C_{1-4}$ alkyl, $C_{1-4}$ alkoxy, $C_{1-4}$ haloalkyl, $C_{1-4}$ haloalkoxy, CN, $NO_2$, aryl, heteroaryl, amino, dialkylamino or $C_{1-4}$ alkoxycarbonyl), phenyl ($C_{1-6}$)alkyl (wherein the phenyl group may be optionally substituted by halogen, $C_{1-4}$ alkyl, $C_{1-4}$ alkoxy, $C_{1-4}$ haloalkyl, $C_{1-4}$ haloalkoxy, CN, $NO_2$, aryl, heteroaryl, amino, dialkylamino, $C_{1-6}$ alkylsulfonyl, $C_{1-6}$ alkoxycarbonyl, or two adjacent positions on the phenyl ring may be cyclised to form a 5, 6 or 7 membered carbocyclic or heterocyclic ring, itself optionally substituted with halogen), heteroaryl ($C_{1-6}$) alkyl (wherein the heteroaryl group may be optionally substituted by halo, nitro, cyano, $C_{1-6}$ alkyl, $C_{1-6}$ haloalkyl, $C_{1-6}$ alkoxy, $C_{1-6}$ haloalkoxy, $C_{1-6}$ alkylsulfonyl, $C_{1-6}$ alkylsulfinyl, $C_{1-6}$ alkylthio, $C_{1-6}$ alkoxycarbonyl, $C_{1-6}$ alkylcarbonylamino, arylcarbonyl, or two adjacent positions on the heteroaryl system may be cyclised to form a 5, 6 or 7 membered carbocyclic or heterocyclic ring, itself optionally substituted with halogen) or heteroaryl (which may be optionally substituted by halo, nitro, cyano, $C_{1-6}$ alkyl, $C_{1-6}$ haloalkyl, $C_{1-6}$ alkoxy or $C_{1-6}$ haloalkoxy, $C_{1-4}$ alkoxycarbonyl $C_{1-6}$ alkylcarbonylamino, phenyloxycarbonylamino (wherein the phenyl group is optionally substituted by halogen, $C_{1-4}$ alkyl, $C_{1-4}$ alkoxy, $C_{1-4}$ haloalkyl, $C_{1-4}$ haloalkoxy, CN, $NO_2$, aryl, heteroaryl, amino or dialkylamino), amino, $C_{1-6}$ alkylamino or phenylamino (wherein the phenyl group is optionally substituted halogen, $C_{1-4}$ alkyl, $C_{1-4}$ alkoxy, $C_{1-4}$ haloalkyl, $C_{1-4}$ haloalkoxy, CN, $NO_2$, aryl, heteroaryl, amino or dialkylamino)).

More preferably $R^1$ is $C_{1-6}$ alkyl, $C_{1-6}$ haloalkyl, $C_{1-6}$ alkoxy($C_{1-6}$)alkyl, heteroaryl($C_{1-3}$) alkyl (wherein the heteroaryl group may be optionally substituted by halo, nitro, cyano, $C_{1-6}$ alkyl, $C_{1-6}$ haloalkyl, $C_{1-6}$ alkoxy, $C_{1-6}$ haloalkoxy, $C_{1-6}$ alkylsulfonyl, $C_{1-6}$ alkoxycarbonyl, or two adjacent positions on the heteroaryl system may be cyclised to form a 5, 6 or 7 membered carbocyclic or heterocyclic ring, itself optionally substituted with halogen), phenyl($C_{1-3}$)alkyl (wherein the phenyl group may be optionally substituted by halogen, $C_{1-4}$ alkyl, $C_{1-4}$ alkoxy, $C_{1-4}$ haloalkyl, $C_{1-4}$ haloalkoxy, CN, $NO_2$, aryl, heteroaryl, amino, dialkylamino, $C_{1-6}$ alkylsulfonyl, $C_{1-6}$ alkoxycarbonyl, or two adjacent positions on the phenyl ring may be cyclised to form a 5, 6 or 7 membered carbocyclic or heterocyclic ring, itself optionally substituted with halogen), phenyl (which may be optionally substituted by halogen, $C_{1-4}$ alkyl, $C_{1-4}$ alkoxy, $C_{1-4}$ haloalkyl, $C_{1-4}$ haloalkoxy, CN, $NO_2$, aryl, heteroaryl, amino, dialkylamino, $C_{1-6}$ alkylsulfonyl, $C_{1-6}$ alkoxycarbonyl, or two adjacent positions on the phenyl ring may be cyclised to form a 5, 6 or 7 membered carbocyclic or heterocyclic ring, itself optionally substituted with halogen), heteroaryl (which may be optionally substituted by halo, nitro, cyano, $C_{1-6}$ alkyl, $C_{1-6}$ haloalkyl, $C_{1-6}$ alkoxy, $C_{1-6}$ haloalkoxy, $C_{1-6}$ alkylsulfonyl, $C_{1-6}$ alkoxycarbonyl, or two adjacent positions on the heteroaryl system may be cyclised to form a 5, 6 or 7 membered carbocyclic or heterocyclic ring, itself optionally substituted with halogen), $C_{1-6}$ alkoxy, $C_{1-6}$ haloalkoxy, $C_{2-6}$ alkenyl, heterocyclyl (optionally substituted by halo, cyano, $C_{1-6}$ alkyl, $C_{1-6}$ haloalkyl, $C_{1-6}$ alkoxy or $C_{1-6}$ haloalkoxy), $C_{1-6}$ alkylthio, $C_{1-6}$ haloalkylthio or $NR^{13}R^{14}$ where $R^{13}$ and $R^{14}$ are independently hydrogen, $C_{1-6}$ alkyl or $C_{1-6}$ haloalkyl, $C_{1-6}$ alkoxy($C_{1-6}$)alkyl, $C_{2-6}$ alkylcarbonyl, phenylcarbonyl, (where the phenyl is optionally substituted by halogen, $C_{1-4}$ alkyl, $C_{1-4}$ alkoxy, $C_{1-4}$ haloalkyl, $C_{1-4}$ haloalkoxy, CN, $NO_2$, aryl, heteroaryl, amino or dialkylamino), phenyl($C_{1-3}$)alkyl (wherein the phenyl group may be optionally substituted by halogen, $C_{1-4}$ alkyl, $C_{1-4}$ alkoxy, $C_{1-4}$ haloalkyl, $C_{1-4}$ haloalkoxy, CN, $NO_2$, aryl, heteroaryl, amino, dialkylamino, $C_{1-6}$ alkylsulfonyl, $C_{1-6}$ alkoxycarbonyl, or two adjacent positions on the phenyl ring may be cyclised to form a 5, 6 or 7 membered carbocyclic or heterocyclic ring, itself optionally substituted with halogen) or heteroaryl($C_{1-3}$)alkyl (wherein the heteroaryl group may be optionally substituted by halo, nitro, cyano, $C_{1-6}$ alkyl, $C_{1-6}$ haloalkyl, $C_{1-6}$ alkoxy, $C_{1-6}$ haloalkoxy, $C_{1-6}$ alkylsulfonyl, $C_{1-6}$ alkylsulfinyl, $C_{1-6}$ alkylthio, $C_{1-6}$ alkoxycarbonyl, $C_{1-6}$ alkylcarbonylamino, arylcarbonyl, or two adjacent positions on the heteroaryl system may be cyclised to form a 5, 6 or 7 membered carbocyclic or heterocyclic ring, itself optionally substituted with halogen).

Even more preferably $R^1$ is $C_{1-6}$ alkyl, $C_{1-6}$ haloalkyl, heteroaryl($C_{1-3}$)alkyl (wherein the heteroaryl group may be optionally substituted by halo, cyano, $C_{1-6}$ alkyl, $C_{1-6}$ haloalkyl and where the heteroaryl group is a thiazole, pyridine, pyrimidine, pyrazine or pyridazine ring), heteroaryl (optionally substituted by halo, cyano, $C_{1-6}$ alkyl, $C_{1-6}$ haloalkyl and where the heteroaryl group is a pyridine, pyrimidine, 2,1,3-benzoxadiazole, pyrazine or pyridazine ring), $C_{1-6}$ alkoxy, $C_{1-6}$ alkoxy($C_{1-6}$)alkyl, $C_{1-6}$ alkylamino, $C_{1-6}$ alkyoxy($C_{1-6}$)alkylamino or heteroaryl($C_{1-3}$)alkylamino (wherein the heteroaryl group may be optionally substituted by halo, cyano, $C_{1-6}$ alkyl, $C_{1-6}$ haloalkyl and where the heteroaryl group is a thiazole, pyridine, pyrimidine, pyrazine or pyridazine ring).

Most preferably $R^1$ is pyridyl (optionally substituted by halo, $C_{1-3}$ alkyl or $C_{1-3}$ haloalkyl) especially halo-substituted pyridyl.

It is preferred that $R^2$ is hydrogen, hydroxy, $C_{1-6}$ alkyl or $C_{1-6}$ haloalkyl.

More preferably $R^2$ is hydrogen, $C_{1-4}$ alkyl or $C_{1-4}$ haloalkyl.

Even more preferably $R^2$ is hydrogen or $C_{1-4}$ alkyl.

Yet more preferably $R^2$ is independently hydrogen or methyl.

Most preferably $R^2$ is hydrogen.

Preferably each $R^4$ is independently halogen, cyano, $C_{1-8}$ alkyl, $C_{1-8}$ haloalkyl, $C_{1-6}$ cyanoalkyl, $C_{1-6}$ alkoxy($C_{1-6}$) alkyl, $C_{3-7}$ cycloalkyl($C_{1-6}$)alkyl, $C_{5-6}$ cycloalkenyl($C_{1-6}$) alkyl, $C_{3-6}$ alkenyloxy($C_{1-6}$)alkyl, $C_{3-6}$ alkynyloxy($C_{1-6}$) alkyl, aryloxy($C_{1-6}$)alkyl, $C_{1-6}$ carboxyalkyl, $C_{1-6}$ alkylcarbonyl($C_{1-6}$)alkyl, $C_{2-6}$ alkenylcarbonyl($C_{1-6}$)alkyl, $C_{2-6}$ alkynylcarbonyl($C_{1-6}$)-alkyl, $C_{1-6}$ alkoxycarbonyl($C_{1-6}$) alkyl, $C_{3-6}$ alkenyloxycarbonyl($C_{1-6}$)alkyl, $C_{3-6}$ alkynyloxycarbonyl($C_{1-6}$)alkyl, aryloxycarbonyl($C_{1-6}$)alkyl, $C_{1-6}$ alkylthio($C_{1-6}$)alkyl, $C_{1-6}$ alkylsulfinyl($C_{1-6}$)alkyl, $C_{1-6}$ alkylsulfonyl($C_{1-6}$)alkyl, aminocarbonyl($C_{1-6}$)alkyl, $C_{1-6}$ alkylaminocarbonyl($C_{1-6}$)alkyl, di($C_{1-6}$)alkylaminocarbonyl ($C_{1-6}$)alkyl, phenyl($C_{1-4}$)alkyl (wherein the phenyl group is optionally substituted by halogen, $C_{1-4}$ alkyl, $C_{1-4}$ alkoxy, $C_{1-4}$ haloalkyl, $C_{1-4}$ haloalkoxy, CN, $NO_2$, aryl, heteroaryl, amino or dialkylamino), heteroaryl($C_{1-4}$)alkyl (wherein the heteroaryl group is optionally substituted by halo, nitro, cyano, $C_{1-6}$ alkyl, $C_{1-6}$ haloalkyl, $C_{1-6}$ alkoxy or $C_{1-6}$ haloalkoxy), heterocyclyl($C_{1-4}$)alkyl (wherein the heterocyclyl group is optionally substituted by halo, nitro, cyano, $C_{1-6}$ alkyl, $C_{1-6}$ haloalkyl, $C_{1-6}$ alkoxy or $C_{1-6}$ haloalkoxy), $C_{2-6}$ alkenyl, aminocarbonyl($C_{2-6}$)alkenyl, $C_{1-6}$ alkylaminocarbonyl($C_{2-6}$)alkenyl, di($C_{1-6}$)alkylaminocarbonyl($C_{2-6}$)alkenyl, phenyl($C_{2-4}$)-alkenyl, (wherein the phenyl group is optionally substituted by halogen, $C_{1-4}$ alkyl, $C_{1-4}$ alkoxy, $C_{1-4}$ haloalkyl, $C_{1-4}$ haloalkoxy, CN, $NO_2$, aryl, heteroaryl, amino or dialkylamino), $C_{2-6}$ alkynyl, trimethylsilyl($C_{2-6}$)alkynyl, aminocarbonyl($C_{2-6}$)alkynyl, $C_{1-6}$ alkylaminocarbonyl($C_{2-6}$) alkynyl, di($C_{1-6}$)alkylaminocarbonyl($C_{2-6}$)alkynyl, $C_{1-6}$ alkoxycarbonyl, $C_{3-7}$ cycloalkyl, $C_{3-7}$ halocycloalkyl, $C_{3-7}$ cyanocycloalkyl, $C_{1-3}$ alkyl($C_{3-7}$)-cycloalkyl, $C_{1-3}$ alkyl($C_{3-7}$)halocycloalkyl, phenyl (optionally substituted by halogen, $C_{1-4}$ alkyl, $C_{1-4}$ alkoxy, $C_{1-4}$ haloalkyl, $C_{1-4}$ haloalkoxy, CN, $NO_2$, aryl, heteroaryl, amino or dialkylamino), heteroaryl (optionally substituted by halo, nitro, cyano, $C_{1-6}$ alkyl, $C_{1-6}$ haloalkyl, $C_{1-6}$ alkoxy or $C_{1-6}$ haloalkoxy), heterocyclyl (wherein the heterocyclyl group is optionally substituted by halo, nitro, cyano, $C_{1-6}$ alkyl, $C_{1-6}$ haloalkyl, $C_{1-6}$ alkoxy or $C_{1-6}$ haloalkoxy), or 2 adjacent groups $R^4$ together with the carbon atoms to which they are attached form a 4, 5, 6 or 7 membered carbocyclic or heterocyclic ring which may be optionally substituted by halogen, $C_{1-8}$ alkoxy, $C_{1-6}$ haloalkoxy, phenoxy (optionally substituted by halo, nitro, cyano, $C_{1-6}$ alkyl, $C_{1-6}$ haloalkyl, $C_{1-6}$ alkoxy or $C_{1-6}$ haloalkoxy), heteroaryloxy (optionally substituted by halo, nitro, cyano, $C_{1-6}$ alkyl, $C_{1-6}$ haloalkyl, $C_{1-6}$ alkoxy or $C_{1-6}$ haloalkoxy), $C_{1-8}$ alkylthio or $R^{19}R^{20}N$ where $R^{19}$ and $R^{20}$ are, independently, hydrogen, $C_{1-8}$ alkyl, $C_{3-7}$ cycloalkyl, $C_{3-6}$ alkenyl, $C_{3-6}$ alkynyl, $C_{2-6}$ haloalkyl, $C_{1-6}$ alkoxycarbonyl or $R^{19}$ and $R^{20}$ together with the N atom to which they are attached form a five, six or seven-membered heterocyclic ring which may contain one or two further heteroatoms selected from O, N or S and which may be optionally substituted by one or two $C_{1-6}$ alkyl groups; n is 0, 1, 2 or 3.

More preferably each $R^4$ is independently halogen, cyano, $C_{1-8}$ alkyl, $C_{1-8}$ haloalkyl, $C_{1-8}$ cyanoalkyl, $C_{1-6}$ alkoxy($C_{1-6}$)alkyl, $C_{2-6}$ alkynyl, trimethylsilyl($C_{2-6}$)alkynyl, $C_{1-6}$ alkoxycarbonyl, $C_{3-7}$ cycloalkyl, $C_{1-3}$ alkyl ($C_{3-7}$) cycloalkyl, phenyl (optionally substituted by halogen, $C_{1-4}$ alkyl, $C_{1-4}$ alkoxy, $C_{1-4}$ haloalkyl, $C_{1-4}$ haloalkoxy, CN, $NO_2$, aryl, heteroaryl, amino or dialkylamino), heterocyclyl (optionally substituted by halo, nitro, cyano, $C_{1-6}$ alkyl, $C_{1-6}$ haloalkyl, $C_{1-6}$ alkoxy or $C_{1-6}$ haloalkoxy), $C_{1-8}$ alkoxy, $C_{1-6}$ haloalkoxy, phenoxy (optionally substituted by halogen, $C_{1-4}$ alkyl, $C_{1-4}$ alkoxy, $C_{1-4}$ haloalkyl, $C_{1-4}$ haloalkoxy, CN, $NO_2$, aryl, heteroaryl, amino or dialkylamino), heteroaryloxy (optionally substituted by halo, nitro, cyano, $C_{1-3}$ alkyl, $C_{1-3}$ haloalkyl, $C_{1-3}$ alkoxy or $C_{1-3}$ haloalkoxy), di($C_{1-8}$) alkylamino, or 2 adjacent groups $R^4$ together with the carbon atoms to which they are attached form a 4, 5, 6 or 7 membered carbocyclic or heterocyclic ring which may be optionally substituted by halogen; n is 0, 1, 2 or 3.

Even more preferably each $R^4$ is independently halogen, cyano, $C_{1-8}$ alkyl, $C_{1-8}$ haloalkyl, $C_{1-8}$ cyanoalkyl, $C_{1-6}$ alkoxy($C_{1-6}$)alkyl, $C_{2-6}$ alkynyl, heterocyclyl (optionally substituted by $C_{1-6}$ alkyl), $C_{1-8}$ alkoxy, $C_{1-6}$ haloalkoxy, phenoxy (optionally substituted by halo, cyano, $C_{1-3}$ alkyl or $C_{1-3}$ haloalkyl), heteroaryloxy (optionally substituted by halo, cyano, $C_{1-3}$ alkyl or $C_{1-3}$ haloalkyl), di($C_{1-8}$)alkylamino or 2 adjacent groups $R^4$ together with the carbon atoms to which they are attached form a 4, 5, 6 or 7 membered carbocyclic or heterocyclic ring which may be optionally substituted by halogen; n is 0, 1, 2 or 3.

Yet more preferably each $R^4$ is independently fluoro, chloro, bromo, cyano, $C_{1-4}$ alkyl, $C_{1-4}$ haloalkyl, $C_{1-4}$ cyanoalkyl or $C_{1-3}$ alkoxy($C_{1-3}$)alkyl; n is 0, 1, 2 or 3, preferably 0, 1 or 2.

Most preferably each $R^4$ is independently fluoro, chloro, bromo, $C_{1-4}$ alkyl or $C_{1-4}$ haloalkyl; n is 1, 2 or 3, preferably 1 or 2.

Preferably $R^8$ is $C_{1-10}$ alkyl, $C_{1-10}$ haloalkyl, aryl($C_{1-6}$)alkyl (wherein the aryl group is optionally substituted by halogen, $C_{1-4}$ alkyl, $C_{1-4}$ alkoxy, $C_{1-4}$ haloalkyl, $C_{1-4}$ haloalkoxy, CN, $NO_2$, aryl, heteroaryl, amino or dialkylamino), heteroaryl($C_{1-6}$)alkyl (wherein the heteroaryl group is optionally substituted by halogen, $C_{1-4}$ alkyl, $C_{1-4}$ alkoxy, $C_{1-4}$ haloalkyl, $C_{1-4}$ haloalkoxy, CN, $NO_2$, aryl, heteroaryl, amino or dialkylamino), arylcarbonyl-($C_{1-6}$)alkyl (wherein the aryl group may be optionally substituted by halogen, $C_{1-4}$ alkyl, $C_{1-4}$ alkoxy, $C_{1-4}$ haloalkyl, $C_{1-4}$ haloalkoxy, CN, $NO_2$, aryl, heteroaryl, amino or dialkylamino and the alkyl group may be optionally substituted by aryl), $C_{2-8}$ alkenyl, $C_{2-8}$ haloalkenyl, aryl($C_{2-6}$)-alkenyl (wherein the aryl group is optionally substituted halogen, $C_{1-4}$ alkyl, $C_{1-4}$ alkoxy, $C_{1-4}$ haloalkyl, $C_{1-4}$ haloalkoxy, CN, $NO_2$, aryl, heteroaryl, amino or dialkylamino, $C_{1-6}$ alkoxycarbonyl, or two adjacent substituents can cyclise to form a 5, 6 or 7 membered carbocyclic or heterocyclic ring), heteroaryl($C_{2-6}$)-alkenyl (wherein the heteroaryl group is optionally substituted halogen, $C_{1-4}$ alkyl, $C_{1-4}$ alkoxy, $C_{1-4}$ haloalkyl, $C_{1-4}$ haloalkoxy, CN, $NO_2$, aryl, heteroaryl, amino or dialkylamino, $C_{1-6}$ alkoxycarbonyl, or two adjacent substituents can cyclise to form a 5, 6 or 7 membered carbocyclic or heterocyclic ring), $C_{2-6}$ alkynyl, phenyl($C_{2-6}$)alkynyl (wherein the phenyl group is optionally substituted by halogen, $C_{1-4}$ alkyl, $C_{1-4}$ alkoxy, $C_{1-4}$ haloalkyl, $C_{1-4}$ haloalkoxy, CN, $NO_2$, aryl, heteroaryl, amino or dialkylamino), $C_{3-7}$ cycloalkyl, $C_{1-6}$ alkoxycarbonyl, $C_{1-6}$ alkylcarbonyl, $C_{1-6}$ haloalkylcarbonyl or aryl($C_{2-6}$)alkenylcarbonyl (wherein the aryl group may be optionally substituted halogen, $C_{1-4}$ alkyl, $C_{1-4}$ alkoxy, $C_{1-4}$ haloalkyl, $C_{1-4}$ haloalkoxy, CN, $NO_2$, aryl, heteroaryl, amino or dialkylamino), or $-C(R^{51})(R^{52})-[CR^{53}=CR^{54}]z-R^{55}$ where z is 1 or 2, $R^{51}$ and $R^{52}$ are each independently H, halo or $C_{1-2}$ alkyl, $R^{53}$ and $R^{54}$ are each independently H, halogen, $C_{1-4}$ alkyl or $C_{1-4}$ haloalkyl and $R^{55}$ is optionally substituted aryl or optionally substituted heteroaryl.

More preferably $R^8$ is phenyl($C_{1-4}$)alkyl (wherein the phenyl group is optionally substituted by halogen, $C_{1-4}$ alkyl, $C_{1-4}$ alkoxy, $C_{1-4}$ haloalkyl, $C_{1-4}$ haloalkoxy, CN, $NO_2$, aryl, heteroaryl, amino or dialkylamino), heteroaryl($C_{1-6}$)alkyl (wherein the heteroaryl group is optionally substituted halogen, $C_{1-4}$ alkyl, $C_{1-4}$ alkoxy, $C_{1-4}$ haloalkyl, $C_{1-4}$ haloalkoxy, CN, $NO_2$, aryl, heteroaryl, amino or dialkylamino), phenyl($C_{2-6}$)alkenyl (wherein the phenyl group is optionally substituted by halogen, $C_{1-4}$ alkyl, $C_{1-4}$ alkoxy, $C_{1-4}$ haloalkyl, $C_{1-4}$ haloalkoxy, CN, $NO_2$, aryl, heteroaryl, amino or dialkylamino), heteroaryl($C_{2-6}$)alkenyl (wherein the heteroaryl group is optionally substituted by halogen, $C_{1-4}$ alkyl, $C_{1-4}$ alkoxy, $C_{1-4}$ haloalkyl, $C_{1-4}$ haloalkoxy, CN, $NO_2$, aryl, heteroaryl, amino or dialkylamino) or phenyl($C_{2-6}$)alkynyl (wherein the phenyl group is optionally substituted by halogen, $C_{1-4}$ alkyl, $C_{1-4}$ alkoxy, $C_{1-4}$ haloalkyl, $C_{1-4}$ haloalkoxy, CN, $NO_2$, aryl, heteroaryl, amino or dialkylamino, or $-C(R^{51})(R^{52})-[CR^{53}=CR^{54}]z-R^{55}$ where z is 1 or 2, $R^{51}$ and $R^{52}$ are each independently H, halo or $C_{1-2}$ alkyl, $R^{53}$ and $R^{54}$ are each independently H, halogen, $C_{1-4}$ alkyl or $C_{1-4}$ haloalkyl and $R^{55}$ is optionally substituted aryl or optionally substituted heteroaryl.

Most preferably $R^8$ is $-C(R^{51})(R^{52})-[CR^{53}=CR^{54}]z-R^{55}$ where z is 1 or 2, preferably 1, $R^{51}$ and $R^{52}$ are each independently H or $C_{1-2}$ alkyl, $R^{53}$ and $R^{54}$ are each independently H, halogen, $C_{1-4}$ alkyl or $C_{1-4}$ haloalkyl and $R^{55}$ is phenyl substituted by halogen, $C_{1-4}$ alkyl, $C_{1-4}$ alkoxy, $C_{1-4}$ haloalkyl, $C_{1-4}$ haloalkoxy, CN, $NO_2$, aryl, heteroaryl, amino or dialkylamino or heteroaryl substituted by halogen, $C_{1-4}$ alkyl, $C_{1-4}$ alkoxy, $C_{1-4}$ haloalkyl, $C_{1-4}$ haloalkoxy, CN, $NO_2$, aryl, heteroaryl, amino or dialkylamino.

$R^{51}$ and $R^{52}$ are preferably hydrogen.

$R^{53}$ and $R^{54}$ are preferably hydrogen or halogen, especially hydrogen.

$R^{55}$ is preferably phenyl substituted with one to three substituents selected from halogen, $C_{1-4}$ alkyl, $C_{1-4}$ alkoxy, $C_{1-4}$ haloalkyl, $C_{1-4}$ haloalkoxy, CN, $NO_2$, aryl, heteroaryl, amino or dialkylamino.

Preferably each Ra is independently halo, cyano, $C_{1-3}$ alkyl, hydroxy or two Ra groups together with the carbon atom to which they are attached form =O, =S, =NRb, =CRcRd where Rb, Rc and Rd are independently H or optionally substituted alkyl, and p is 0, 1 or 2.

More preferably each Ra is independently fluoro, methyl, hydroxy or two Ra groups together with the carbon atom to which they are attached form a carbonyl group and p is 0, 1 or 2.

Most preferably p is 0.

It is preferred that that ring

is a 6-membered aromatic ring or is 5 or 6 membered heteroaromatic ring wherein the ring members are each independently CH, S, N, $NR^4$, O, or $CR^4$ provided that at least one ring member is other than CH or CR4 and that there are no more than one O or S atoms present in the ring.

More preferably the ring

is a benzene, pyridine, pyrimidine, pyrazine, pyridazine, triazine, furan, thiophene, pyrrole, imidazole, pyrazole, oxazole, thiazole, isoxazole, isothiazole, [1,2,3]triazole, [1,2,3]oxadiazole or [1,2,3]thiadiazole.

Most preferably the ring

is a benzene or pyridine ring.

Certain compounds of formula (I) are novel and as such form a further aspect of the invention. One group of novel compounds are compounds of formula I'

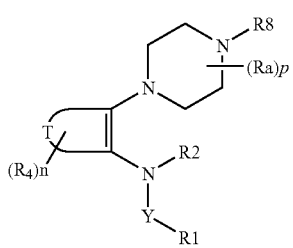

wherein $R^1$, $R^2$, $R^4$, Ra, T, Y, n and p are as defined in relation to formula I and $R^8$ is —$C(R^{51})(R^{52})$—$[CR^{53}$=$CR^{54}]z$-$R^{55}$ where z is 1 or 2, preferably 1, $R^{51}$ and $R^{52}$ are each independently H or $C_{1-2}$ alkyl, $R^{53}$ and $R^{54}$ are each independently H, halogen, $C_{1-4}$ alkyl or $C_{1-4}$ haloalkyl and $R^{55}$ is phenyl substituted by halogen, $C_{1-4}$ alkyl, $C_{1-4}$ alkoxy, $C_{1-4}$ haloalkyl, $C_{1-4}$ haloalkoxy, CN, $NO_2$, aryl, heteroaryl, amino or dialkylamino or heteroaryl substituted by halogen, $C_{1-4}$ alkyl, $C_{1-4}$ alkoxy, $C_{1-4}$ haloalkyl, $C_{1-4}$ haloalkoxy, CN, $NO_2$, aryl, heteroaryl, amino or dialkylamino.

The compounds in Tables I to XXV below illustrate the compounds of the invention.

Table I provides 897 compounds of formula Ia

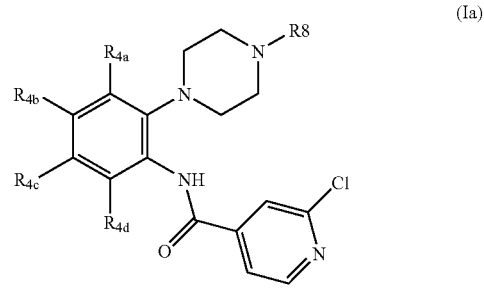

wherein the values of $R^8$, $R^{4a}$, $R^{4b}$, $R^{4c}$ and $R^{4d}$ are given in Table 1.

TABLE 1

| Compound No | $R^8$ | $R^{4a}$ | $R^{4b}$ | $R^{4c}$ | $R^{4d}$ |
|---|---|---|---|---|---|
| I-1 | 4-chlorobenzyl | H | H | H | H |
| I-2 | Cinnamyl | H | H | H | H |
| I-3 | 4-chlorocinnamyl | H | H | H | H |
| I-4 | 4-fluorocinnamyl | H | H | H | H |
| I-5 | 4-bromocinnamyl | H | H | H | H |
| I-6 | 4-trifluoromethylcinnamyl | H | H | H | H |
| I-7 | 4-trifluoromethoxycinnamyl | H | H | H | H |
| I-8 | 4-pentafluoroethoxycinnamyl | H | H | H | H |
| I-9 | 4-methoxycinnamyl | H | H | H | H |
| I-10 | 4-ethoxycinnamyl | H | H | H | H |
| I-11 | 4-cyanocinnamyl | H | H | H | H |
| I-12 | 3-(6-chloro-pyridin-3-yl)-allyl | H | H | H | H |
| I-13 | 3-(4-chlorophenyl)-but-2-enyl | H | H | H | H |
| I-14 | 3-(4-chlorophenyl)-3-fluoro-allyl | H | H | H | H |
| I-15 | 3-chloro-4-fluoro-cinnamyl | H | H | H | H |
| I-16 | 3,5-dichloro-cinnamyl | H | H | H | H |
| I-17 | 5-phenyl-penta-2,4-dienyl | H | H | H | H |
| I-18 | 4-isopropyloxycarbonylamino-cinnamyl | H | H | H | H |
| I-19 | 3-naphthalen-2-yl-allyl | H | H | H | H |
| I-20 | 3-(5-trifluoromethyl-pyridin-2-yl)-allyl | H | H | H | H |
| I-21 | 3-(5-chloro-pyridin-2-yl)-allyl | H | H | H | H |
| I-22 | 3-pyridin-4-yl-allyl | H | H | H | H |
| I-23 | 3-(2-Chloro-pyridin-4-yl)-allyl | H | H | H | H |
| I-24 | 4-chlorobenzyl | H | F | H | H |
| I-25 | Cinnamyl | H | F | H | H |
| I-26 | 4-chlorocinnamyl | H | F | H | H |
| I-27 | 4-fluorocinnamyl | H | F | H | H |
| I-28 | 4-bromocinnamyl | H | F | H | H |
| I-29 | 4-trifluoromethylcinnamyl | H | F | H | H |
| I-30 | 4-trifluoromethoxycinnamyl | H | F | H | H |
| I-31 | 4-pentafluoroethoxycinnamyl | H | F | H | H |
| I-32 | 4-methoxycinnamyl | H | F | H | H |
| I-33 | 4-ethoxycinnamyl | H | F | H | H |
| I-34 | 4-cyanocinnamyl | H | F | H | H |
| I-35 | 3-(6-chloro-pyridin-3-yl)-allyl | H | F | H | H |
| I-36 | 3-(4-chlorophenyl)-but-2-enyl | H | F | H | H |
| I-37 | 3-(4-chlorophenyl)-3-fluoro-allyl | H | F | H | H |
| I-38 | 3-chloro-4-fluoro-cinnamyl | H | F | H | H |
| I-39 | 3,5-dichloro-cinnamyl | H | F | H | H |
| I-40 | 5-phenyl-penta-2,4-dienyl | H | F | H | H |

TABLE 1-continued

| Compound No | R⁸ | R⁴ᵃ | R⁴ᵇ | R⁴ᶜ | R⁴ᵈ |
|---|---|---|---|---|---|
| I-41 | 4-isopropyloxycarbonylamino-cinnamyl | H | F | H | H |
| I-42 | 3-naphthalen-2-yl-allyl | H | F | H | H |
| I-43 | 3-(5-trifluoromethyl-pyridin-2-yl)-allyl | H | F | H | H |
| I-44 | 3-(5-chloro-pyridin-2-yl)-allyl | H | F | H | H |
| I-45 | 3-pyridin-4-yl-allyl | H | F | H | H |
| I-46 | 3-(2-Chloro-pyridin-4-yl)-allyl | H | F | H | H |
| I-47 | 4-chlorobenzyl | H | Cl | H | H |
| I-48 | Cinnamyl | H | Cl | H | H |
| I-49 | 4-chlorocinnamyl | H | Cl | H | H |
| I-50 | 4-fluorocinnamyl | H | Cl | H | H |
| I-51 | 4-bromocinnamyl | H | Cl | H | H |
| I-52 | 4-trifluoromethylcinnamyl | H | Cl | H | H |
| I-53 | 4-trifluoromethoxycinnamyl | H | Cl | H | H |
| I-54 | 4-pentafluoroethoxycinnamyl | H | Cl | H | H |
| I-55 | 4-methoxycinnamyl | H | Cl | H | H |
| I-56 | 4-ethoxycinnamyl | H | Cl | H | H |
| I-57 | 4-cyanocinnamyl | H | Cl | H | H |
| I-58 | 3-(6-chloro-pyridin-3-yl)-allyl | H | Cl | H | H |
| I-59 | 3-(4-chlorophenyl)-but-2-enyl | H | Cl | H | H |
| I-60 | 3-(4-chlorophenyl)-3-fluoro-allyl | H | Cl | H | H |
| I-61 | 3-chloro-4-fluoro-cinnamyl | H | Cl | H | H |
| I-62 | 3,5-dichloro-cinnamyl | H | Cl | H | H |
| I-63 | 5-phenyl-penta-2,4-dienyl | H | Cl | H | H |
| I-64 | 4-isopropyloxycarbonylamino-cinnamyl | H | Cl | H | H |
| I-65 | 3-naphthalen-2-yl-allyl | H | Cl | H | H |
| I-66 | 3-(5-trifluoromethyl-pyridin-2-yl)-allyl | H | Cl | H | H |
| I-67 | 3-(5-chloro-pyridin-2-yl)-allyl | H | Cl | H | H |
| I-68 | 3-pyridin-4-yl-allyl | H | Cl | H | H |
| I-69 | 3-(2-Chloro-pyridin-4-yl)-allyl | H | Cl | H | H |
| I-70 | 4-chlorobenzyl | H | H | F | H |
| I-71 | Cinnamyl | H | H | F | H |
| I-72 | 4-chlorocinnamyl | H | H | F | H |
| I-73 | 4-fluorocinnamyl | H | H | F | H |
| I-74 | 4-bromocinnamyl | H | H | F | H |
| I-75 | 4-trifluoromethylcinnamyl | H | H | F | H |
| I-76 | 4-trifluoromethoxycinnamyl | H | H | F | H |
| I-77 | 4-pentafluoroethoxycinnamyl | H | H | F | H |
| I-78 | 4-methoxycinnamyl | H | H | F | H |
| I-79 | 4-ethoxycinnamyl | H | H | F | H |
| I-80 | 4-cyanocinnamyl | H | H | F | H |
| I-81 | 3-(6-chloro-pyridin-3-yl)-allyl | H | H | F | H |
| I-82 | 3-(4-chlorophenyl)-but-2-enyl | H | H | F | H |
| I-83 | 3-(4-chlorophenyl)-3-fluoro-allyl | H | H | F | H |
| I-84 | 3-chloro-4-fluoro-cinnamyl | H | H | F | H |
| I-85 | 3,5-dichloro-cinnamyl | H | H | F | H |
| I-86 | 5-phenyl-penta-2,4-dienyl | H | H | F | H |
| I-87 | 4-isopropyloxycarbonylamino-cinnamyl | H | H | F | H |
| I-88 | 3-naphthalen-2-yl-allyl | H | H | F | H |
| I-89 | 3-(5-trifluoromethyl-pyridin-2-yl)-allyl | H | H | F | H |
| I-90 | 3-(5-chloro-pyridin-2-yl)-allyl | H | H | F | H |
| I-91 | 3-pyridin-4-yl-allyl | H | H | F | H |
| I-92 | 3-(2-Chloro-pyridin-4-yl)-allyl | H | H | F | H |
| I-93 | 4-chlorobenzyl | H | H | Cl | H |
| I-94 | Cinnamyl | H | H | Cl | H |
| I-95 | 4-chlorocinnamyl | H | H | Cl | H |
| I-96 | 4-fluorocinnamyl | H | H | Cl | H |
| I-97 | 4-bromocinnamyl | H | H | Cl | H |
| I-98 | 4-trifluoromethylcinnamyl | H | H | Cl | H |
| I-99 | 4-trifluoromethoxycinnamyl | H | H | Cl | H |
| I-100 | 4-pentafluoroethoxycinnamyl | H | H | Cl | H |
| I-101 | 4-methoxycinnamyl | H | H | Cl | H |
| I-102 | 4-ethoxycinnamyl | H | H | Cl | H |
| I-103 | 4-cyanocinnamyl | H | H | Cl | H |
| I-104 | 3-(6-chloro-pyridin-3-yl)-allyl | H | H | Cl | H |
| I-105 | 3-(4-chlorophenyl)-but-2-enyl | H | H | Cl | H |
| I-106 | 3-(4-chlorophenyl)-3-fluoro-allyl | H | H | Cl | H |
| I-107 | 3-chloro-4-fluoro-cinnamyl | H | H | Cl | H |
| I-108 | 3,5-dichloro-cinnamyl | H | H | Cl | H |
| I-109 | 5-phenyl-penta-2,4-dienyl | H | H | Cl | H |
| I-110 | 4-isopropyloxycarbonylamino-cinnamyl | H | H | Cl | H |
| I-111 | 3-naphthalen-2-yl-allyl | H | H | Cl | H |
| I-112 | 3-(5-trifluoromethyl-pyridin-2-yl)-allyl | H | H | Cl | H |
| I-113 | 3-(5-chloro-pyridin-2-yl)-allyl | H | H | Cl | H |
| I-114 | 3-pyridin-4-yl-allyl | H | H | Cl | H |
| I-115 | 3-(2-Chloro-pyridin-4-yl)-allyl | H | H | Cl | H |
| I-116 | 4-chlorobenzyl | Cl | Cl | H | H |
| I-117 | Cinnamyl | Cl | Cl | H | H |
| I-118 | 4-chlorocinnamyl | Cl | Cl | H | H |
| I-119 | 4-fluorocinnamyl | Cl | Cl | H | H |
| I-120 | 4-bromocinnamyl | Cl | Cl | H | H |
| I-121 | 4-trifluoromethylcinnamyl | Cl | Cl | H | H |
| I-122 | 4-trifluoromethoxycinnamyl | Cl | Cl | H | H |
| I-123 | 4-pentafluoroethoxycinnamyl | Cl | Cl | H | H |
| I-124 | 4-methoxycinnamyl | Cl | Cl | H | H |
| I-125 | 4-ethoxycinnamyl | Cl | Cl | H | H |
| I-126 | 4-cyanocinnamyl | Cl | Cl | H | H |
| I-127 | 3-(6-chloro-pyridin-3-yl)-allyl | Cl | Cl | H | H |
| I-128 | 3-(4-chlorophenyl)-but-2-enyl | Cl | Cl | H | H |
| I-129 | 3-(4-chlorophenyl)-3-fluoro-allyl | Cl | Cl | H | H |
| I-130 | 3-chloro-4-fluoro-cinnamyl | Cl | Cl | H | H |
| I-131 | 3,5-dichloro-cinnamyl | Cl | Cl | H | H |
| I-132 | 5-phenyl-penta-2,4-dienyl | Cl | Cl | H | H |
| I-133 | 4-isopropyloxycarbonylamino-cinnamyl | Cl | Cl | H | H |
| I-134 | 3-naphthalen-2-yl-allyl | Cl | Cl | H | H |
| I-135 | 3-(5-trifluoromethyl-pyridin-2-yl)-allyl | Cl | Cl | H | H |
| I-136 | 3-(5-chloro-pyridin-2-yl)-allyl | Cl | Cl | H | H |
| I-137 | 3-pyridin-4-yl-allyl | Cl | Cl | H | H |
| I-138 | 3-(2-Chloro-pyridin-4-yl)-allyl | Cl | Cl | H | H |
| I-139 | 4-chlorobenzyl | F | F | H | H |
| I-140 | Cinnamyl | F | F | H | H |
| I-141 | 4-chlorocinnamyl | F | F | H | H |
| I-142 | 4-fluorocinnamyl | F | F | H | H |
| I-143 | 4-bromocinnamyl | F | F | H | H |
| I-144 | 4-trifluoromethylcinnamyl | F | F | H | H |
| I-145 | 4-trifluoromethoxycinnamyl | F | F | H | H |
| I-146 | 4-pentafluoroethoxycinnamyl | F | F | H | H |
| I-147 | 4-methoxycinnamyl | F | F | H | H |
| I-148 | 4-ethoxycinnamyl | F | F | H | H |
| I-149 | 4-cyanocinnamyl | F | F | H | H |
| I-150 | 3-(6-chloro-pyridin-3-yl)-allyl | F | F | H | H |
| I-151 | 3-(4-chlorophenyl)-but-2-enyl | F | F | H | H |
| I-152 | 3-(4-chlorophenyl)-3-fluoro-allyl | F | F | H | H |
| I-153 | 3-chloro-4-fluoro-cinnamyl | F | F | H | H |
| I-154 | 3,5-dichloro-cinnamyl | F | F | H | H |
| I-155 | 5-phenyl-penta-2,4-dienyl | F | F | H | H |
| I-156 | 4-isopropyloxycarbonylamino-cinnamyl | F | F | H | H |
| I-157 | 3-naphthalen-2-yl-allyl | F | F | H | H |
| I-158 | 3-(5-trifluoromethyl-pyridin-2-yl)-allyl | F | F | H | H |
| I-159 | 3-(5-chloro-pyridin-2-yl)-allyl | F | F | H | H |
| I-160 | 3-pyridin-4-yl-allyl | F | F | H | H |
| I-161 | 3-(2-Chloro-pyridin-4-yl)-allyl | F | F | H | H |
| I-162 | 4-chlorobenzyl | F | H | F | H |
| I-163 | Cinnamyl | F | H | F | H |
| I-164 | 4-chlorocinnamyl | F | H | F | H |
| I-165 | 4-fluorocinnamyl | F | H | F | H |
| I-166 | 4-bromocinnamyl | F | H | F | H |
| I-167 | 4-trifluoromethylcinnamyl | F | H | F | H |
| I-168 | 4-trifluoromethoxycinnamyl | F | H | F | H |
| I-169 | 4-pentafluoroethoxycinnamyl | F | H | F | H |
| I-170 | 4-methoxycinnamyl | F | H | F | H |
| I-171 | 4-ethoxycinnamyl | F | H | F | H |
| I-172 | 4-cyanocinnamyl | F | H | F | H |
| I-173 | 3-(6-chloro-pyridin-3-yl)-allyl | F | H | F | H |
| I-174 | 3-(4-chlorophenyl)-but-2-enyl | F | H | F | H |

TABLE 1-continued

| Compound No | R⁸ | R⁴ᵃ | R⁴ᵇ | R⁴ᶜ | R⁴ᵈ |
|---|---|---|---|---|---|
| I-175 | 3-(4-chlorophenyl)-3-fluoro-allyl | F | H | F | H |
| I-176 | 3-chloro-4-fluoro-cinnamyl | F | H | F | H |
| I-177 | 3,5-dichloro-cinnamyl | F | H | F | H |
| I-178 | 5-phenyl-penta-2,4-dienyl | F | H | F | H |
| I-179 | 4-isopropyloxycarbonylamino-cinnamyl | F | H | F | H |
| I-180 | 3-naphthalen-2-yl-allyl | F | H | F | H |
| I-181 | 3-(5-trifluoromethyl-pyridin-2-yl)-allyl | F | H | F | H |
| I-182 | 3-(5-chloro-pyridin-2-yl)-allyl | F | H | F | H |
| I-183 | 3-pyridin-4-yl-allyl | F | H | F | H |
| I-184 | 3-(2-Chloro-pyridin-4-yl)-allyl | F | H | F | H |
| I-185 | 4-chlorobenzyl | F | H | H | F |
| I-186 | Cinnamyl | F | H | H | F |
| I-187 | 4-chlorocinnamyl | F | H | H | F |
| I-188 | 4-fluorocinnamyl | F | H | H | F |
| I-189 | 4-bromocinnamyl | F | H | H | F |
| I-190 | 4-trifluoromethylcinnamyl | F | H | H | F |
| I-191 | 4-trifluoromethoxycinnamyl | F | H | H | F |
| I-192 | 4-pentafluoroethoxycinnamyl | F | H | H | F |
| I-193 | 4-methoxycinnamyl | F | H | H | F |
| I-194 | 4-ethoxycinnamyl | F | H | H | F |
| I-195 | 4-cyanocinnamyl | F | H | H | F |
| I-196 | 3-(6-chloro-pyridin-3-yl)-allyl | F | H | H | F |
| I-197 | 3-(4-chlorophenyl)-but-2-enyl | F | H | H | F |
| I-198 | 3-(4-chlorophenyl)-3-fluoro-allyl | F | H | H | F |
| I-199 | 3-chloro-4-fluoro-cinnamyl | F | H | H | F |
| I-200 | 3,5-dichloro-cinnamyl | F | H | H | F |
| I-201 | 5-phenyl-penta-2,4-dienyl | F | H | H | F |
| I-202 | 4-isopropyloxycarbonylamino-cinnamyl | F | H | H | F |
| I-203 | 3-naphthalen-2-yl-allyl | F | H | H | F |
| I-204 | 3-(5-trifluoromethyl-pyridin-2-yl)-allyl | F | H | H | F |
| I-205 | 3-(5-chloro-pyridin-2-yl)-allyl | F | H | H | F |
| I-206 | 3-pyridin-4-yl-allyl | F | H | H | F |
| I-207 | 3-(2-Chloro-pyridin-4-yl)-allyl | F | H | H | F |
| I-208 | 4-chlorobenzyl | Cl | H | Cl | H |
| I-209 | Cinnamyl | Cl | H | Cl | H |
| I-210 | 4-chlorocinnamyl | Cl | H | Cl | H |
| I-211 | 4-fluorocinnamyl | Cl | H | Cl | H |
| I-212 | 4-bromocinnamyl | Cl | H | Cl | H |
| I-213 | 4-trifluoromethylcinnamyl | Cl | H | Cl | H |
| I-214 | 4-trifluoromethoxycinnamyl | Cl | H | Cl | H |
| I-215 | 4-pentafluoroethoxycinnamyl | Cl | H | Cl | H |
| I-216 | 4-methoxycinnamyl | Cl | H | Cl | H |
| I-217 | 4-ethoxycinnamyl | Cl | H | Cl | H |
| I-218 | 4-cyanocinnamyl | Cl | H | Cl | H |
| I-219 | 3-(6-chloro-pyridin-3-yl)-allyl | Cl | H | Cl | H |
| I-220 | 3-(4-chlorophenyl)-but-2-enyl | Cl | H | Cl | H |
| I-221 | 3-(4-chlorophenyl)-3-fluoro-allyl | Cl | H | Cl | H |
| I-222 | 3-chloro-4-fluoro-cinnamyl | Cl | H | Cl | H |
| I-223 | 3,5-dichloro-cinnamyl | Cl | H | Cl | H |
| I-224 | 5-phenyl-penta-2,4-dienyl | Cl | H | Cl | H |
| I-225 | 4-isopropyloxycarbonylamino-cinnamyl | Cl | H | Cl | H |
| I-226 | 3-naphthalen-2-yl-allyl | Cl | H | Cl | H |
| I-227 | 3-(5-trifluoromethyl-pyridin-2-yl)-allyl | Cl | H | Cl | H |
| I-228 | 3-(5-chloro-pyridin-2-yl)-allyl | Cl | H | Cl | H |
| I-229 | 3-pyridin-4-yl-allyl | Cl | H | Cl | H |
| I-230 | 3-(2-Chloro-pyridin-4-yl)-allyl | Cl | H | Cl | H |
| I-231 | 4-chlorobenzyl | Cl | H | H | Cl |
| I-232 | Cinnamyl | Cl | H | H | Cl |
| I-233 | 4-chlorocinnamyl | Cl | H | H | Cl |
| I-234 | 4-fluorocinnamyl | Cl | H | H | Cl |
| I-235 | 4-bromocinnamyl | Cl | H | H | Cl |
| I-236 | 4-trifluoromethylcinnamyl | Cl | H | H | Cl |
| I-237 | 4-trifluoromethoxycinnamyl | Cl | H | H | Cl |
| I-238 | 4-pentafluoroethoxycinnamyl | Cl | H | H | Cl |
| I-239 | 4-methoxycinnamyl | Cl | H | H | Cl |
| I-240 | 4-ethoxycinnamyl | Cl | H | H | Cl |
| I-241 | 4-cyanocinnamyl | Cl | H | H | Cl |
| I-242 | 3-(6-chloro-pyridin-3-yl)-allyl | Cl | H | H | Cl |
| I-243 | 3-(4-chlorophenyl)-but-2-enyl | Cl | H | H | Cl |
| I-244 | 3-(4-chlorophenyl)-2-fluoro-allyl | Cl | H | H | Cl |
| I-245 | 3-chloro-4-fluoro-cinnamyl | Cl | H | H | Cl |
| I-246 | 3,5-dichloro-cinnamyl | Cl | H | H | Cl |
| I-247 | 5-phenyl-penta-2,4-dienyl | Cl | H | H | Cl |
| I-248 | 4-isopropyloxycarbonylamino-cinnamyl | Cl | H | H | Cl |
| I-249 | 3-naphthalen-2-yl-allyl | Cl | H | H | Cl |
| I-250 | 3-(5-trifluoromethyl-pyridin-2-yl)-allyl | Cl | H | H | Cl |
| I-251 | 3-(5-chloro-pyridin-2-yl)-allyl | Cl | H | H | Cl |
| I-252 | 3-pyridin-4-yl-allyl | Cl | H | H | Cl |
| I-253 | 3-(2-Chloro-pyridin-4-yl)-allyl | Cl | H | H | Cl |
| I-254 | 4-chlorobenzyl | F | Cl | H | H |
| I-255 | Cinnamyl | F | Cl | H | H |
| I-256 | 4-chlorocinnamyl | F | Cl | H | H |
| I-257 | 4-fluorocinnamyl | F | Cl | H | H |
| I-258 | 4-bromocinnamyl | F | Cl | H | H |
| I-259 | 4-trifluoromethylcinnamyl | F | Cl | H | H |
| I-260 | 4-trifluoromethoxycinnamyl | F | Cl | H | H |
| I-261 | 4-pentafluoroethoxycinnamyl | F | Cl | H | H |
| I-262 | 4-methoxycinnamyl | F | Cl | H | H |
| I-263 | 4-ethoxycinnamyl | F | Cl | H | H |
| I-264 | 4-cyanocinnamyl | F | Cl | H | H |
| I-265 | 3-(6-chloro-pyridin-3-yl)-allyl | F | Cl | H | H |
| I-266 | 3-(4-chlorophenyl)-but-2-enyl | F | Cl | H | H |
| I-267 | 3-(4-chlorophenyl)-3-fluoro-allyl | F | Cl | H | H |
| I-268 | 3-chloro-4-fluoro-cinnamyl | F | Cl | H | H |
| I-269 | 3,5-dichloro-cinnamyl | F | Cl | H | H |
| I-270 | 5-phenyl-penta-2,4-dienyl | F | Cl | H | H |
| I-271 | 4-isopropyloxycarbonylamino-cinnamyl | F | Cl | H | H |
| I-272 | 3-naphthalen-2-yl-allyl | F | Cl | H | H |
| I-273 | 3-(5-trifluoromethyl-pyridin-2-yl)-allyl | F | Cl | H | H |
| I-274 | 3-(5-chloro-pyridin-2-yl)-allyl | F | Cl | H | H |
| I-275 | 3-pyridin-4-yl-allyl | F | Cl | H | H |
| I-276 | 3-(2-Chloro-pyridin-4-yl)-allyl | F | Cl | H | H |
| I-277 | 4-chlorobenzyl | F | H | Cl | H |
| I-278 | Cinnamyl | F | H | Cl | H |
| I-279 | 4-chlorocinnamyl | F | H | Cl | H |
| I-280 | 4-fluorocinnamyl | F | H | Cl | H |
| I-281 | 4-bromocinnamyl | F | H | Cl | H |
| I-282 | 4-trifluoromethylcinnamyl | F | H | Cl | H |
| I-283 | 4-trifluoromethoxycinnamyl | F | H | Cl | H |
| I-284 | 4-pentafluoroethoxycinnamyl | F | H | Cl | H |
| I-285 | 4-methoxycinnamyl | F | H | Cl | H |
| I-286 | 4-ethoxycinnamyl | F | H | Cl | H |
| I-287 | 4-cyanocinnamyl | F | H | Cl | H |
| I-288 | 3-(6-chloro-pyridin-3-yl)-allyl | F | H | Cl | H |
| I-289 | 3-(4-chlorophenyl)-but-2-enyl | F | H | Cl | H |
| I-290 | 3-(4-chlorophenyl)-3-fluoro-allyl | F | H | Cl | H |
| I-291 | 3-chloro-4-fluoro-cinnamyl | F | H | Cl | H |
| I-292 | 3,5-dichloro-cinnamyl | F | H | Cl | H |
| I-293 | 5-phenyl-penta-2,4-dienyl | F | H | Cl | H |
| I-294 | 4-isopropyloxycarbonylamino-cinnamyl | F | H | Cl | H |
| I-295 | 3-naphthalen-2-yl-allyl | F | H | Cl | H |
| I-296 | 3-(5-trifluoromethyl-pyridin-2-yl)-allyl | F | H | Cl | H |
| I-297 | 3-(5-chloro-pyridin-2-yl)-allyl | F | H | Cl | H |
| I-298 | 3-pyridin-4-yl-allyl | F | H | Cl | H |
| I-299 | 3-(2-Chloro-pyridin-4-yl)-allyl | F | H | Cl | H |
| I-300 | 4-chlorobenzyl | F | H | H | Cl |
| I-301 | Cinnamyl | F | H | H | Cl |
| I-302 | 4-chlorocinnamyl | F | H | H | Cl |
| I-303 | 4-fluorocinnamyl | F | H | H | Cl |
| I-304 | 4-bromocinnamyl | F | H | H | Cl |
| I-305 | 4-trifluoromethylcinnamyl | F | H | H | Cl |
| I-306 | 4-trifluoromethoxycinnamyl | F | H | H | Cl |
| I-307 | 4-pentafluoroethoxycinnamyl | F | H | H | Cl |
| I-308 | 4-methoxycinnamyl | F | H | H | Cl |

TABLE 1-continued

| Compound No | R⁸ | R⁴ᵃ | R⁴ᵇ | R⁴ᶜ | R⁴ᵈ |
|---|---|---|---|---|---|
| I-309 | 4-ethoxycinnamyl | F | H | H | Cl |
| I-310 | 4-cyanocinnamyl | F | H | H | Cl |
| I-311 | 3-(6-chloro-pyridin-3-yl)-allyl | F | H | H | Cl |
| I-312 | 3-(4-chlorophenyl)-but-2-enyl | F | H | H | Cl |
| I-313 | 3-(4-chlorophenyl)-3-fluoro-allyl | F | H | H | Cl |
| I-314 | 3-chloro-4-fluoro-cinnamyl | F | H | H | Cl |
| I-315 | 3,5-dichloro-cinnamyl | F | H | H | Cl |
| I-316 | 5-phenyl-penta-2,4-dienyl | F | H | H | Cl |
| I-317 | 4-isopropyloxycarbonylamino-cinnamyl | F | H | H | Cl |
| I-318 | 3-naphthalen-2-yl-allyl | F | H | H | Cl |
| I-319 | 3-(5-trifluoromethyl-pyridin-2-yl)-allyl | F | H | H | Cl |
| I-320 | 3-(5-chloro-pyridin-2-yl)-allyl | F | H | H | Cl |
| I-321 | 3-pyridin-4-yl-allyl | F | H | H | Cl |
| I-322 | 3-(2-Chloro-pyridin-4-yl)-allyl | F | H | H | Cl |
| I-323 | 4-chlorobenzyl | Cl | F | H | H |
| I-324 | Cinnamyl | Cl | F | H | H |
| I-325 | 4-chlorocinnamyl | Cl | F | H | H |
| I-326 | 4-fluorocinnamyl | Cl | F | H | H |
| I-327 | 4-bromocinnamyl | Cl | F | H | H |
| I-328 | 4-trifluoromethylcinnamyl | Cl | F | H | H |
| I-329 | 4-trifluoromethoxycinnamyl | Cl | F | H | H |
| I-330 | 4-pentafluoroethoxycinnamyl | Cl | F | H | H |
| I-331 | 4-methoxycinnamyl | Cl | F | H | H |
| I-332 | 4-ethoxycinnamyl | Cl | F | H | H |
| I-333 | 4-cyanocinnamyl | Cl | F | H | H |
| I-334 | 3-(6-chloro-pyridin-3-yl)-allyl | Cl | F | H | H |
| I-335 | 3-(4-chlorophenyl)-but-2-enyl | Cl | F | H | H |
| I-336 | 3-(4-chlorophenyl)-3-fluoro-allyl | Cl | F | H | H |
| I-337 | 3-chloro-4-fluoro-cinnamyl | Cl | F | H | H |
| I-338 | 3,5-dichloro-cinnamyl | Cl | F | H | H |
| I-339 | 5-phenyl-penta-2,4-dienyl | Cl | F | H | H |
| I-340 | 4-isopropyloxycarbonylamino-cinnamyl | Cl | F | H | H |
| I-341 | 3-naphthalen-2-yl-allyl | Cl | F | H | H |
| I-342 | 3-(5-trifluoromethyl-pyridin-2-yl)-allyl | Cl | F | H | H |
| I-343 | 3-(5-chloro-pyridin-2-yl)-allyl | Cl | F | H | H |
| I-344 | 3-pyridin-4-yl-allyl | Cl | F | H | H |
| I-345 | 3-(2-Chloro-pyridin-4-yl)-allyl | Cl | F | H | H |
| I-346 | 4-chlorobenzyl | H | F | Cl | H |
| I-347 | Cinnamyl | H | F | Cl | H |
| I-348 | 4-chlorocinnamyl | H | F | Cl | H |
| I-349 | 4-fluorocinnamyl | H | F | Cl | H |
| I-350 | 4-bromocinnamyl | H | F | Cl | H |
| I-351 | 4-trifluoromethylcinnamyl | H | F | Cl | H |
| I-352 | 4-trifluoromethoxycinnamyl | H | F | Cl | H |
| I-353 | 4-pentafluoroethoxycinnamyl | H | F | Cl | H |
| I-354 | 4-methoxycinnamyl | H | F | Cl | H |
| I-355 | 4-ethoxycinnamyl | H | F | Cl | H |
| I-356 | 4-cyanocinnamyl | H | F | Cl | H |
| I-357 | 3-(6-chloro-pyridin-3-yl)-allyl | H | F | Cl | H |
| I-358 | 3-(4-chlorophenyl)-but-2-enyl | H | F | Cl | H |
| I-359 | 3-(4-chlorophenyl)-3-fluoro-allyl | H | F | Cl | H |
| I-360 | 3-chloro-4-fluoro-cinnamyl | H | F | Cl | H |
| I-361 | 3,5-dichloro-cinnamyl | H | F | Cl | H |
| I-362 | 5-phenyl-penta-2,4-dienyl | H | F | Cl | H |
| I-363 | 4-isopropyloxycarbonylamino-cinnamyl | H | F | Cl | H |
| I-364 | 3-naphthalen-2-yl-allyl | H | F | Cl | H |
| I-365 | 3-(5-trifluoromethyl-pyridin-2-yl)-allyl | H | F | Cl | H |
| I-366 | 3-(5-chloro-pyridin-2-yl)-allyl | H | F | Cl | H |
| I-367 | 3-pyridin-4-yl-allyl | H | F | Cl | H |
| I-368 | 3-(2-Chloro-pyridin-4-yl)-allyl | H | F | Cl | H |
| I-369 | 4-chlorobenzyl | H | F | H | Cl |
| I-370 | Cinnamyl | H | F | H | Cl |
| I-371 | 4-chlorocinnamyl | H | F | H | Cl |
| I-372 | 4-fluorocinnamyl | H | F | H | Cl |
| I-373 | 4-bromocinnamyl | H | F | H | Cl |
| I-374 | 4-trifluoromethylcinnamyl | H | F | H | Cl |
| I-375 | 4-trifluoromethoxycinnamyl | H | F | H | Cl |
| I-376 | 4-pentafluoroethoxycinnamyl | H | F | H | Cl |
| I-377 | 4-methoxycinnamyl | H | F | H | Cl |
| I-378 | 4-ethoxycinnamyl | H | F | H | Cl |
| I-379 | 4-cyanocinnamyl | H | F | H | Cl |
| I-380 | 3-(6-chloro-pyridin-3-yl)-allyl | H | F | H | Cl |
| I-381 | 3-(4-chlorophenyl)-but-2-enyl | H | F | H | Cl |
| I-382 | 3-(4-chlorophenyl)-3-fluoro-allyl | H | F | H | Cl |
| I-383 | 3-chloro-4-fluoro-cinnamyl | H | F | H | Cl |
| I-384 | 3,5-dichloro-cinnamyl | H | F | H | Cl |
| I-385 | 5-phenyl-penta-2,4-dienyl | H | F | H | Cl |
| I-386 | 4-isopropyloxycarbonylamino-cinnamyl | H | F | H | Cl |
| I-387 | 3-naphthalen-2-yl-allyl | H | F | H | Cl |
| I-388 | 3-(5-trifluoromethyl-pyridin-2-yl)-allyl | H | F | H | Cl |
| I-389 | 3-(5-chloro-pyridin-2-yl)-allyl | H | F | H | Cl |
| I-390 | 3-pyridin-4-yl-allyl | H | F | H | Cl |
| I-391 | 3-(2-Chloro-pyridin-4-yl)-allyl | H | F | H | Cl |
| I-392 | 4-chlorobenzyl | Cl | H | F | H |
| I-393 | Cinnamyl | Cl | H | F | H |
| I-394 | 4-chlorocinnamyl | Cl | H | F | H |
| I-395 | 4-fluorocinnamyl | Cl | H | F | H |
| I-396 | 4-bromocinnamyl | Cl | H | F | H |
| I-397 | 4-trifluoromethylcinnamyl | Cl | H | F | H |
| I-398 | 4-trifluoromethoxycinnamyl | Cl | H | F | H |
| I-399 | 4-pentafluoroethoxycinnamyl | Cl | H | F | H |
| I-400 | 4-methoxycinnamyl | Cl | H | F | H |
| I-401 | 4-ethoxycinnamyl | Cl | H | F | H |
| I-402 | 4-cyanocinnamyl | Cl | H | F | H |
| I-403 | 3-(6-chloro-pyridin-3-yl)-allyl | Cl | H | F | H |
| I-404 | 3-(4-chlorophenyl)-but-2-enyl | Cl | H | F | H |
| I-405 | 3-(4-chlorophenyl)-3-fluoro-allyl | Cl | H | F | H |
| I-406 | 3-chloro-4-fluoro-cinnamyl | Cl | H | F | H |
| I-407 | 3,5-dichloro-cinnamyl | Cl | H | F | H |
| I-408 | 5-phenyl-penta-2,4-dienyl | Cl | H | F | H |
| I-409 | 4-isopropyloxycarbonylamino-cinnamyl | Cl | H | F | H |
| I-410 | 3-naphthalen-2-yl-allyl | Cl | H | F | H |
| I-411 | 3-(5-trifluoromethyl-pyridin-2-yl)-allyl | Cl | H | F | H |
| I-412 | 3-(5-chloro-pyridin-2-yl)-allyl | Cl | H | F | H |
| I-413 | 3-pyridin-4-yl-allyl | Cl | H | F | H |
| I-414 | 3-(2-Chloro-pyridin-4-yl)-allyl | Cl | H | F | H |
| I-415 | 4-chlorobenzyl | H | Cl | F | H |
| I-416 | Cinnamyl | H | Cl | F | H |
| I-417 | 4-chlorocinnamyl | H | Cl | F | H |
| I-418 | 4-fluorocinnamyl | H | Cl | F | H |
| I-419 | 4-bromocinnamyl | H | Cl | F | H |
| I-420 | 4-trifluoromethylcinnamyl | H | Cl | F | H |
| I-421 | 4-trifluoromethoxycinnamyl | H | Cl | F | H |
| I-422 | 4-pentafluoroethoxycinnamyl | H | Cl | F | H |
| I-423 | 4-methoxycinnamyl | H | Cl | F | H |
| I-424 | 4-ethoxycinnamyl | H | Cl | F | H |
| I-425 | 4-cyanocinnamyl | H | Cl | F | H |
| I-426 | 3-(6-chloro-pyridin-3-yl)-allyl | H | Cl | F | H |
| I-427 | 3-(4-chlorophenyl)-but-2-enyl | H | Cl | F | H |
| I-428 | 3-(4-chlorophenyl)-3-fluoro-allyl | H | Cl | F | H |
| I-429 | 3-chloro-4-fluoro-cinnamyl | H | Cl | F | H |
| I-430 | 3,5-dichloro-cinnamyl | H | Cl | F | H |
| I-431 | 5-phenyl-penta-2,4-dienyl | H | Cl | F | H |
| I-432 | 4-isopropyloxycarbonylamino-cinnamyl | H | Cl | F | H |
| I-433 | 3-naphthalen-2-yl-allyl | H | Cl | F | H |
| I-434 | 3-(5-trifluoromethyl-pyridin-2-yl)-allyl | H | Cl | F | H |
| I-435 | 3-(5-chloro-pyridin-2-yl)-allyl | H | Cl | F | H |
| I-436 | 3-pyridin-4-yl-allyl | H | Cl | F | H |
| I-437 | 3-(2-Chloro-pyridin-4-yl)-allyl | H | Cl | F | H |
| I-438 | 4-chlorobenzyl | H | H | F | Cl |
| I-439 | Cinnamyl | H | H | F | Cl |
| I-440 | 4-chlorocinnamyl | H | H | F | Cl |
| I-441 | 4-fluorocinnamyl | H | H | F | Cl |
| I-442 | 4-bromocinnamyl | H | H | F | Cl |

TABLE 1-continued

| Compound No | R$^8$ | R$^{4a}$ | R$^{4b}$ | R$^{4c}$ | R$^{4d}$ |
|---|---|---|---|---|---|
| I-443 | 4-trifluoromethylcinnamyl | H | H | F | Cl |
| I-444 | 4-trifluoromethoxycinnamyl | H | H | F | Cl |
| I-445 | 4-pentafluoroethoxycinnamyl | H | H | F | Cl |
| I-446 | 4-methoxycinnamyl | H | H | F | Cl |
| I-447 | 4-ethoxycinnamyl | H | H | F | Cl |
| I-448 | 4-cyanocinnamyl | H | H | F | Cl |
| I-449 | 3-(6-chloro-pyridin-3-yl)-allyl | H | H | F | Cl |
| I-450 | 3-(4-chlorophenyl)-but-2-enyl | H | H | F | Cl |
| I-451 | 3-(4-chlorophenyl)-3-fluoro-allyl | H | H | F | Cl |
| I-452 | 3-chloro-4-fluoro-cinnamyl | H | H | F | Cl |
| I-453 | 3,5-dichloro-cinnamyl | H | H | F | Cl |
| I-454 | 5-phenyl-penta-2,4-dienyl | H | H | F | Cl |
| I-455 | 4-isopropyloxycarbonylamino-cinnamyl | H | H | F | Cl |
| I-456 | 3-naphthalen-2-yl-allyl | H | H | F | Cl |
| I-457 | 3-(5-trifluoromethyl-pyridin-2-yl)-allyl | H | H | F | Cl |
| I-458 | 3-(5-chloro-pyridin-2-yl)-allyl | H | H | F | Cl |
| I-459 | 3-pyridin-4-yl-allyl | H | H | F | Cl |
| I-460 | 3-(2-Chloro-pyridin-4-yl)-allyl | H | H | F | Cl |
| I-461 | 4-chlorobenzyl | Cl | H | H | F |
| I-462 | Cinnamyl | Cl | H | H | F |
| I-463 | 4-chlorocinnamyl | Cl | H | H | F |
| I-464 | 4-fluorocinnamyl | Cl | H | H | F |
| I-465 | 4-bromocinnamyl | Cl | H | H | F |
| I-466 | 4-trifluoromethylcinnamyl | Cl | H | H | F |
| I-467 | 4-trifluoromethoxycinnamyl | Cl | H | H | F |
| I-468 | 4-pentafluoroethoxycinnamyl | Cl | H | H | F |
| I-469 | 4-methoxycinnamyl | Cl | H | H | F |
| I-470 | 4-ethoxycinnamyl | Cl | H | H | F |
| I-471 | 4-cyanocinnamyl | Cl | H | H | F |
| I-472 | 3-(6-chloro-pyridin-3-yl)-allyl | Cl | H | H | F |
| I-473 | 3-(4-chlorophenyl)-but-2-enyl | Cl | H | H | F |
| I-474 | 3-(4-chlorophenyl)-3-fluoro-allyl | Cl | H | H | F |
| I-475 | 3-chloro-4-fluoro-cinnamyl | Cl | H | H | F |
| I-476 | 3,5-dichloro-cinnamyl | Cl | H | H | F |
| I-477 | 5-phenyl-penta-2,4-dienyl | Cl | H | H | F |
| I-478 | 4-isopropyloxycarbonylamino-cinnamyl | Cl | H | H | F |
| I-479 | 3-naphthalen-2-yl-allyl | Cl | H | H | F |
| I-480 | 3-(5-trifluoromethyl-pyridin-2-yl)-allyl | Cl | H | H | F |
| I-481 | 3-(5-chloro-pyridin-2-yl)-allyl | Cl | H | H | F |
| I-482 | 3-pyridin-4-yl-allyl | Cl | H | H | F |
| I-483 | 3-(2-Chloro-pyridin-4-yl)-allyl | Cl | H | H | F |
| I-484 | 4-chlorobenzyl | H | Cl | H | F |
| I-485 | Cinnamyl | H | Cl | H | F |
| I-486 | 4-chlorocinnamyl | H | Cl | H | F |
| I-487 | 4-fluorocinnamyl | H | Cl | H | F |
| I-488 | 4-bromocinnamyl | H | Cl | H | F |
| I-489 | 4-trifluoromethylcinnamyl | H | Cl | H | F |
| I-490 | 4-trifluoromethoxycinnamyl | H | Cl | H | F |
| I-491 | 4-pentafluoroethoxycinnamyl | H | Cl | H | F |
| I-492 | 4-methoxycinnamyl | H | Cl | H | F |
| I-493 | 4-ethoxycinnamyl | H | Cl | H | F |
| I-494 | 4-cyanocinnamyl | H | Cl | H | F |
| I-495 | 3-(6-chloro-pyridin-3-yl)-allyl | H | Cl | H | F |
| I-496 | 3-(4-chlorophenyl)-but-2-enyl | H | Cl | H | F |
| I-497 | 3-(4-chlorophenyl)-3-fluoro-allyl | H | Cl | H | F |
| I-498 | 3-chloro-4-fluoro-cinnamyl | H | Cl | H | F |
| I-499 | 3,5-dichloro-cinnamyl | H | Cl | H | F |
| I-500 | 5-phenyl-penta-2,4-dienyl | H | Cl | H | F |
| I-501 | 4-isopropyloxycarbonylamino-cinnamyl | H | Cl | H | F |
| I-502 | 3-naphthalen-2-yl-allyl | H | Cl | H | F |
| I-503 | 3-(5-trifluoromethyl-pyridin-2-yl)-allyl | H | Cl | H | F |
| I-504 | 3-(5-chloro-pyridin-2-yl)-allyl | H | Cl | H | F |
| I-505 | 3-pyridin-4-yl-allyl | H | Cl | H | F |
| I-506 | 3-(2-Chloro-pyridin-4-yl)-allyl | H | Cl | H | F |
| I-507 | 4-chlorobenzyl | H | H | Cl | F |
| I-508 | Cinnamyl | H | H | Cl | F |
| I-509 | 4-chlorocinnamyl | H | H | Cl | F |
| I-510 | 4-fluorocinnamyl | H | H | Cl | F |
| I-511 | 4-bromocinnamyl | H | H | Cl | F |
| I-512 | 4-trifluoromethylcinnamyl | H | H | Cl | F |
| I-513 | 4-trifluoromethoxycinnamyl | H | H | Cl | F |
| I-514 | 4-pentafluoroethoxycinnamyl | H | H | Cl | F |
| I-515 | 4-methoxycinnamyl | H | H | Cl | F |
| I-516 | 4-ethoxycinnamyl | H | H | Cl | F |
| I-517 | 4-cyanocinnamyl | H | H | Cl | F |
| I-518 | 3-(6-chloro-pyridin-3-yl)-allyl | H | H | Cl | F |
| I-519 | 3-(4-chlorophenyl)-but-2-enyl | H | H | Cl | F |
| I-520 | 3-(4-chlorophenyl)-3-fluoro-allyl | H | H | Cl | F |
| I-521 | 3-chloro-4-fluoro-cinnamyl | H | H | Cl | F |
| I-522 | 3,5-dichloro-cinnamyl | H | H | Cl | F |
| I-523 | 5-phenyl-penta-2,4-dienyl | H | H | Cl | F |
| I-524 | 4-isopropyloxycarbonylamino-cinnamyl | H | H | Cl | F |
| I-525 | 3-naphthalen-2-yl-allyl | H | H | Cl | F |
| I-526 | 3-(5-trifluoromethyl-pyridin-2-yl)-allyl | H | H | Cl | F |
| I-527 | 3-(5-chloro-pyridin-2-yl)-allyl | H | H | Cl | F |
| I-528 | 3-pyridin-4-yl-allyl | H | H | Cl | F |
| I-529 | 3-(2-Chloro-pyridin-4-yl)-allyl | H | H | Cl | F |
| I-530 | 4-chlorobenzyl | H | F | F | F |
| I-531 | Cinnamyl | H | F | F | F |
| I-532 | 4-chlorocinnamyl | H | F | F | F |
| I-533 | 4-fluorocinnamyl | H | F | F | F |
| I-534 | 4-bromocinnamyl | H | F | F | F |
| I-535 | 4-trifluoromethylcinnamyl | H | F | F | F |
| I-536 | 4-trifluoromethoxycinnamyl | H | F | F | F |
| I-537 | 4-pentafluoroethoxycinnamyl | H | F | F | F |
| I-538 | 4-methoxycinnamyl | H | F | F | F |
| I-539 | 4-ethoxycinnamyl | H | F | F | F |
| I-540 | 4-cyanocinnamyl | H | F | F | F |
| I-541 | 3-(6-chloro-pyridin-3-yl)-allyl | H | F | F | F |
| I-542 | 3-(4-chlorophenyl)-but-2-enyl | H | F | F | F |
| I-543 | 3-(4-chlorophenyl)-3-fluoro-allyl | H | F | F | F |
| I-544 | 3-chloro-4-fluoro-cinnamyl | H | F | F | F |
| I-545 | 3,5-dichloro-cinnamyl | H | F | F | F |
| I-546 | 5-phenyl-penta-2,4-dienyl | H | F | F | F |
| I-547 | 4-isopropyloxycarbonylamino-cinnamyl | H | F | F | F |
| I-548 | 3-naphthalen-2-yl-allyl | H | F | F | F |
| I-549 | 3-(5-trifluoromethyl-pyridin-2-yl)-allyl | H | F | F | F |
| I-550 | 3-(5-chloro-pyridin-2-yl)-allyl | H | F | F | F |
| I-551 | 3-pyridin-4-yl-allyl | H | F | F | F |
| I-552 | 3-(2-Chloro-pyridin-4-yl)-allyl | H | F | F | F |
| I-553 | 4-chlorobenzyl | F | H | F | F |
| I-554 | Cinnamyl | F | H | F | F |
| I-555 | 4-chlorocinnamyl | F | H | F | F |
| I-556 | 4-fluorocinnamyl | F | H | F | F |
| I-557 | 4-bromocinnamyl | F | H | F | F |
| I-558 | 4-trifluoromethylcinnamyl | F | H | F | F |
| I-559 | 4-trifluoromethoxycinnamyl | F | H | F | F |
| I-560 | 4-pentafluoroethoxycinnamyl | F | H | F | F |
| I-561 | 4-methoxycinnamyl | F | H | F | F |
| I-562 | 4-ethoxycinnamyl | F | H | F | F |
| I-563 | 4-cyanocinnamyl | F | H | F | F |
| I-564 | 3-(6-chloro-pyridin-3-yl)-allyl | F | H | F | F |
| I-565 | 3-(4-chlorophenyl)-but-2-enyl | F | H | F | F |
| I-566 | 3-(4-chlorophenyl)-3-fluoro-allyl | F | H | F | F |
| I-567 | 3-chloro-4-fluoro-cinnamyl | F | H | F | F |
| I-568 | 3,5-dichloro-cinnamyl | F | H | F | F |
| I-569 | 5-phenyl-penta-2,4-dienyl | F | H | F | F |
| I-570 | 4-isopropyloxycarbonylamino-cinnamyl | F | H | F | F |
| I-571 | 3-naphthalen-2-yl-allyl | F | H | F | F |
| I-572 | 3-(5-trifluoromethyl-pyridin-2-yl)-allyl | F | H | F | F |
| I-573 | 3-(5-chloro-pyridin-2-yl)-allyl | F | H | F | F |
| I-574 | 3-pyridin-4-yl-allyl | F | H | F | F |
| I-575 | 3-(2-Chloro-pyridin-4-yl)-allyl | F | H | F | F |
| I-576 | 4-chlorobenzyl | F | F | H | F |

TABLE 1-continued

| Compound No | R⁸ | R⁴ᵃ | R⁴ᵇ | R⁴ᶜ | R⁴ᵈ |
|---|---|---|---|---|---|
| I-577 | Cinnamyl | F | F | H | F |
| I-578 | 4-chlorocinnamyl | F | F | H | F |
| I-579 | 4-fluorocinnamyl | F | F | H | F |
| I-580 | 4-bromocinnamyl | F | F | H | F |
| I-581 | 4-trifluoromethylcinnamyl | F | F | H | F |
| I-582 | 4-trifluoromethoxycinnamyl | F | F | H | F |
| I-583 | 4-pentafluoroethoxycinnamyl | F | F | H | F |
| I-584 | 4-methoxycinnamyl | F | F | H | F |
| I-585 | 4-ethoxycinnamyl | F | F | H | F |
| I-586 | 4-cyanocinnamyl | F | F | H | F |
| I-587 | 3-(6-chloro-pyridin-3-yl)-allyl | F | F | H | F |
| I-588 | 3-(4-chlorophenyl)-but-2-enyl | F | F | H | F |
| I-589 | 3-(4-chlorophenyl)-3-fluoro-allyl | F | F | H | F |
| I-590 | 3-chloro-4-fluoro-cinnamyl | F | F | H | F |
| I-591 | 3,5-dichloro-cinnamyl | F | F | H | F |
| I-592 | 5-phenyl-penta-2,4-dienyl | F | F | H | F |
| I-593 | 4-isopropyloxycarbonylamino-cinnamyl | F | F | H | F |
| I-594 | 3-naphthalen-2-yl-allyl | F | F | H | F |
| I-595 | 3-(5-trifluoromethyl-pyridin-2-yl)-allyl | F | F | H | F |
| I-596 | 3-(5-chloro-pyridin-2-yl)-allyl | F | F | H | F |
| I-597 | 3-pyridin-4-yl-allyl | F | F | H | F |
| I-598 | 3-(2-Chloro-pyridin-4-yl)-allyl | F | F | H | F |
| I-599 | 4-chlorobenzyl | F | F | F | H |
| I-600 | Cinnamyl | F | F | F | H |
| I-601 | 4-chlorocinnamyl | F | F | F | H |
| I-602 | 4-fluorocinnamyl | F | F | F | H |
| I-603 | 4-bromocinnamyl | F | F | F | H |
| I-604 | 4-trifluoromethylcinnamyl | F | F | F | H |
| I-605 | 4-trifluoromethoxycinnamyl | F | F | F | H |
| I-606 | 4-pentafluoroethoxycinnamyl | F | F | F | H |
| I-607 | 4-methoxycinnamyl | F | F | F | H |
| I-608 | 4-ethoxycinnamyl | F | F | F | H |
| I-609 | 4-cyanocinnamyl | F | F | F | H |
| I-610 | 3-(6-chloro-pyridin-3-yl)-allyl | F | F | F | H |
| I-611 | 3-(4-chlorophenyl)-but-2-enyl | F | F | F | H |
| I-612 | 3-(4-chlorophenyl)-3-fluoro-allyl | F | F | F | H |
| I-613 | 3-chloro-4-fluoro-cinnamyl | F | F | F | H |
| I-614 | 3,5-dichloro-cinnamyl | F | F | F | H |
| I-615 | 5-phenyl-penta-2,4-dienyl | F | F | F | H |
| I-616 | 4-isopropyloxycarbonylamino-cinnamyl | F | F | F | H |
| I-617 | 3-naphthalen-2-yl-allyl | F | F | F | H |
| I-618 | 3-(5-trifluoromethyl-pyridin-2-yl)-allyl | F | F | F | H |
| I-619 | 3-(5-chloro-pyridin-2-yl)-allyl | F | F | F | H |
| I-620 | 3-pyridin-4-yl-allyl | F | F | F | H |
| I-621 | 3-(2-Chloro-pyridin-4-yl)-allyl | F | F | F | H |
| I-622 | 4-chlorobenzyl | H | Cl | Cl | Cl |
| I-623 | Cinnamyl | H | Cl | Cl | Cl |
| I-624 | 4-chlorocinnamyl | H | Cl | Cl | Cl |
| I-625 | 4-fluorocinnamyl | H | Cl | Cl | Cl |
| I-626 | 4-bromocinnamyl | H | Cl | Cl | Cl |
| I-627 | 4-trifluoromethylcinnamyl | H | Cl | Cl | Cl |
| I-628 | 4-trifluoromethoxycinnamyl | H | Cl | Cl | Cl |
| I-629 | 4-pentafluoroethoxycinnamyl | H | Cl | Cl | Cl |
| I-630 | 4-methoxycinnamyl | H | Cl | Cl | Cl |
| I-631 | 4-ethoxycinnamyl | H | Cl | Cl | Cl |
| I-632 | 4-cyanocinnamyl | H | Cl | Cl | Cl |
| I-633 | 3-(6-chloro-pyridin-3-yl)-allyl | H | Cl | Cl | Cl |
| I-634 | 3-(4-chlorophenyl)-but-2-enyl | H | Cl | Cl | Cl |
| I-635 | 3-(4-chlorophenyl)-3-fluoro-allyl | H | Cl | Cl | Cl |
| I-636 | 3-chloro-4-fluoro-cinnamyl | H | Cl | Cl | Cl |
| I-637 | 3,5-dichloro-cinnamyl | H | Cl | Cl | Cl |
| I-638 | 5-phenyl-penta-2,4-dienyl | H | Cl | Cl | Cl |
| I-639 | 4-isopropyloxycarbonylamino-cinnamyl | H | Cl | Cl | Cl |
| I-640 | 3-naphthalen-2-yl-allyl | H | Cl | Cl | Cl |
| I-641 | 3-(5-trifluoromethyl-pyridin-2-yl)-allyl | H | Cl | Cl | Cl |
| I-642 | 3-(5-chloro-pyridin-2-yl)-allyl | H | Cl | Cl | Cl |
| I-643 | 3-pyridin-4-yl-allyl | H | Cl | Cl | Cl |
| I-644 | 3-(2-Chloro-pyridin-4-yl)-allyl | H | Cl | Cl | Cl |
| I-645 | 4-chlorobenzyl | Cl | H | Cl | Cl |
| I-646 | Cinnamyl | Cl | H | Cl | Cl |
| I-647 | 4-chlorocinnamyl | Cl | H | Cl | Cl |
| I-648 | 4-fluorocinnamyl | Cl | H | Cl | Cl |
| I-649 | 4-bromocinnamyl | Cl | H | Cl | Cl |
| I-650 | 4-trifluoromethylcinnamyl- | Cl | H | Cl | Cl |
| I-651 | 4-trifluoromethoxycinnamyl | Cl | H | Cl | Cl |
| I-652 | 4-pentafluoroethoxycinnamyl | Cl | H | Cl | Cl |
| I-653 | 4-methoxycinnamyl | Cl | H | Cl | Cl |
| I-654 | 4-ethoxycinnamyl | Cl | H | Cl | Cl |
| I-655 | 4-cyanocinnamyl | Cl | H | Cl | Cl |
| I-656 | 3-(6-chloro-pyridin-3-yl)-allyl | Cl | H | Cl | Cl |
| I-657 | 3-(4-chlorophenyl)-but-2-enyl | Cl | H | Cl | Cl |
| I-658 | 3-(4-chlorophenyl)-3-fluoro-allyl | Cl | H | Cl | Cl |
| I-659 | 3-chloro-4-fluoro-cinnamyl | Cl | H | Cl | Cl |
| I-660 | 3,5-dichloro-cinnamyl | Cl | H | Cl | Cl |
| I-661 | 5-phenyl-penta-2,4-dienyl | Cl | H | Cl | Cl |
| I-662 | 4-isopropyloxycarbonylamino-cinnamyl | Cl | H | Cl | Cl |
| I-663 | 3-naphthalen-2-yl-allyl | Cl | H | Cl | Cl |
| I-664 | 3-(5-trifluoromethyl-pyridin-2-yl)-allyl | Cl | H | Cl | Cl |
| I-665 | 3-(5-chloro-pyridin-2-yl)-allyl | Cl | H | Cl | Cl |
| I-666 | 3-pyridin-4-yl-allyl | Cl | H | Cl | Cl |
| I-667 | 3-(2-Chloro-pyridin-4-yl)-allyl | Cl | H | Cl | Cl |
| I-668 | 4-chlorobenzyl | Cl | Cl | H | Cl |
| I-669 | Cinnamyl | Cl | Cl | H | Cl |
| I-670 | 4-chlorocinnamyl | Cl | Cl | H | Cl |
| I-671 | 4-fluorocinnamyl | Cl | Cl | H | Cl |
| I-672 | 4-bromocinnamyl | Cl | Cl | H | Cl |
| I-673 | 4-trifluoromethylcinnamyl | Cl | Cl | H | Cl |
| I-674 | 4-trifluoromethoxycinnamyl | Cl | Cl | H | Cl |
| I-675 | 4-pentafluoroethoxycinnamyl | Cl | Cl | H | Cl |
| I-676 | 4-methoxycinnamyl | Cl | Cl | H | Cl |
| I-677 | 4-ethoxycinnamyl | Cl | Cl | H | Cl |
| I-678 | 4-cyanocinnamyl | Cl | Cl | H | Cl |
| I-679 | 3-(6-chloro-pyridin-3-yl)-allyl | Cl | Cl | H | Cl |
| I-680 | 3-(4-chlorophenyl)-but-2-enyl | Cl | Cl | H | Cl |
| I-681 | 3-(4-chlorophenyl)-3-fluoro-allyl | Cl | Cl | H | Cl |
| I-682 | 3-chloro-4-fluoro-cinnamyl | Cl | Cl | H | Cl |
| I-683 | 3,5-dichloro-cinnamyl | Cl | Cl | H | Cl |
| I-684 | 5-phenyl-penta-2,4-dienyl | Cl | Cl | H | Cl |
| I-685 | 4-isopropyloxycarbonylamino-cinnamyl | Cl | Cl | H | Cl |
| I-686 | 3-naphthalen-2-yl-allyl | Cl | Cl | H | Cl |
| I-687 | 3-(5-trifluoromethyl-pyridin-2-yl)-allyl | Cl | Cl | H | Cl |
| I-688 | 3-(5-chloro-pyridin-2-yl)-allyl | Cl | Cl | H | Cl |
| I-689 | 3-pyridin-4-yl-allyl | Cl | Cl | H | Cl |
| I-690 | 3-(2-Chloro-pyridin-4-yl)-allyl | Cl | Cl | H | Cl |
| I-691 | 4-chlorobenzyl | Cl | Cl | Cl | H |
| I-692 | Cinnamyl | Cl | Cl | Cl | H |
| I-693 | 4-chlorocinnamyl | Cl | Cl | Cl | H |
| I-694 | 4-fluorocinnamyl | Cl | Cl | Cl | H |
| I-695 | 4-bromocinnamyl | Cl | Cl | Cl | H |
| I-696 | 4-trifluoromethylcinnamyl | Cl | Cl | Cl | H |
| I-697 | 4-trifluoromethoxycinnamyl | Cl | Cl | Cl | H |
| I-698 | 4-pentafluoroethoxycinnamyl | Cl | Cl | Cl | H |
| I-699 | 4-methoxycinnamyl | Cl | Cl | Cl | H |
| I-700 | 4-ethoxycinnamyl | Cl | Cl | Cl | H |
| I-701 | 4-cyanocinnamyl | Cl | Cl | Cl | H |
| I-702 | 3-(6-chloro-pyridin-3-yl)-allyl | Cl | Cl | Cl | H |
| I-703 | 3-(4-chlorophenyl)-but-2-enyl | Cl | Cl | Cl | H |
| I-704 | 3-(4-chlorophenyl)-3-fluoro-allyl | Cl | Cl | Cl | H |
| I-705 | 3-chloro-4-fluoro-cinnamyl | Cl | Cl | Cl | H |
| I-706 | 3,5-dichloro-cinnamyl | Cl | Cl | Cl | H |
| I-707 | 5-phenyl-penta-2,4-dienyl | Cl | Cl | Cl | H |
| I-708 | 4-isopropyloxycarbonylamino-cinnamyl | Cl | Cl | Cl | H |
| I-709 | 3-naphthalen-2-yl-allyl | Cl | Cl | Cl | H |
| I-710 | 3-(5-trifluoromethyl-pyridin-2-yl)-allyl | Cl | Cl | Cl | H |

TABLE 1-continued

| Compound No | R8 | R4a | R4b | R4c | R4d |
|---|---|---|---|---|---|
| I-711 | 3-(5-chloro-pyridin-2-yl)-allyl | Cl | Cl | Cl | H |
| I-712 | 3-pyridin-4-yl-allyl | Cl | Cl | Cl | H |
| I-713 | 3-(2-Chloro-pyridin-4-yl)-allyl | Cl | Cl | Cl | H |
| I-714 | 4-chlorobenzyl | Cl | Cl | Cl | Cl |
| I-715 | Cinnamyl | Cl | Cl | Cl | Cl |
| I-716 | 4-chlorocinnamyl | Cl | Cl | Cl | Cl |
| I-717 | 4-fluorocinnamyl | Cl | Cl | Cl | Cl |
| I-718 | 4-bromocinnamyl | Cl | Cl | Cl | Cl |
| I-719 | 4-trifluoromethylcinnamyl | Cl | Cl | Cl | Cl |
| I-720 | 4-trifluoromethoxycinnamyl | Cl | Cl | Cl | Cl |
| I-721 | 4-pentafluoroethoxycinnamyl | Cl | Cl | Cl | Cl |
| I-722 | 4-methoxycinnamyl | Cl | Cl | Cl | Cl |
| I-723 | 4-ethoxycinnamyl | Cl | Cl | Cl | Cl |
| I-724 | 4-cyanocinnamyl | Cl | Cl | Cl | Cl |
| I-725 | 3-(6-chloro-pyridin-3-yl)-allyl | Cl | Cl | Cl | Cl |
| I-726 | 3-(4-chlorophenyl)-but-2-enyl | Cl | Cl | Cl | Cl |
| I-727 | 3-(4-chlorophenyl)-3-fluoro-allyl | Cl | Cl | Cl | Cl |
| I-728 | 3-chloro-4-fluoro-cinnamyl | Cl | Cl | Cl | Cl |
| I-729 | 3,5-dichloro-cinnamyl | Cl | Cl | Cl | Cl |
| I-730 | 5-phenyl-penta-2,4-dienyl | Cl | Cl | Cl | Cl |
| I-731 | 4-isopropyloxycarbonylamino-cinnamyl | Cl | Cl | Cl | Cl |
| I-732 | 3-naphthalen-2-yl-allyl | Cl | Cl | Cl | Cl |
| I-733 | 3-(5-trifluoromethyl-pyridin-2-yl)-allyl | Cl | Cl | Cl | Cl |
| I-734 | 3-(5-chloro-pyridin-2-yl)-allyl | Cl | Cl | Cl | Cl |
| I-735 | 3-pyridin-4-yl-allyl | Cl | Cl | Cl | Cl |
| I-736 | 3-(2-Chloro-pyridin-4-yl)-allyl | Cl | Cl | Cl | Cl |
| I-737 | 4-chlorobenzyl | F | F | F | F |
| I-738 | Cinnamyl | F | F | F | F |
| I-739 | 4-chlorocinnamyl | F | F | F | F |
| I-740 | 4-fluorocinnamyl | F | F | F | F |
| I-741 | 4-bromocinnamyl | F | F | F | F |
| I-742 | 4-trifluoromethylcinnamyl | F | F | F | F |
| I-743 | 4-trifluoromethoxycinnamyl | F | F | F | F |
| I-744 | 4-pentafluoroethoxycinnamyl | F | F | F | F |
| I-745 | 4-methoxycinnamyl | F | F | F | F |
| I-746 | 4-ethoxycinnamyl | F | F | F | F |
| I-747 | 4-cyanocinnamyl | F | F | F | F |
| I-748 | 3-(6-chloro-pyridin-3-yl)-allyl | F | F | F | F |
| I-749 | 3-(4-chlorophenyl)-but-2-enyl | F | F | F | F |
| I-750 | 3-(4-chlorophenyl)-3-fluoro-allyl | F | F | F | F |
| I-751 | 3-chloro-4-fluoro-cinnamyl | F | F | F | F |
| I-752 | 3,5-dichloro-cinnamyl | F | F | F | F |
| I-753 | 5-phenyl-penta-2,4-dienyl | F | F | F | F |
| I-754 | 4-isopropyloxycarbonylamino-cinnamyl | F | F | F | F |
| I-755 | 3-naphthalen-2-yl-allyl | F | F | F | F |
| I-756 | 3-(5-trifluoromethyl-pyridin-2-yl)-allyl | F | F | F | F |
| I-757 | 3-(5-chloro-pyridin-2-yl)-allyl | F | F | F | F |
| I-758 | 3-pyridin-4-yl-allyl | F | F | F | F |
| I-759 | 3-(2-Chloro-pyridin-4-yl)-allyl | F | F | F | F |
| I-760 | 4-chlorobenzyl | H | F | H | F |
| I-761 | Cinnamyl | H | F | H | F |
| I-762 | 4-chlorocinnamyl | H | F | H | F |
| I-763 | 4-fluorocinnamyl | H | F | H | F |
| I-764 | 4-bromocinnamyl | H | F | H | F |
| I-765 | 4-trifluoromethylcinnamyl | H | F | H | F |
| I-766 | 4-trifluoromethoxycinnamyl | H | F | H | F |
| I-767 | 4-pentafluoroethoxycinnamyl | H | F | H | F |
| I-768 | 4-methoxycinnamyl | H | F | H | F |
| I-769 | 4-ethoxycinnamyl | H | F | H | F |
| I-770 | 4-cyanocinnamyl | H | F | H | F |
| I-771 | 3-(6-chloro-pyridin-3-yl)-allyl | H | F | H | F |
| I-772 | 3-(4-chlorophenyl)-but-2-enyl | H | F | H | F |
| I-773 | 3-(4-chlorophenyl)-3-fluoro-allyl | H | F | H | F |
| I-774 | 3-chloro-4-fluoro-cinnamyl | H | F | H | F |
| I-775 | 3,5-dichloro-cinnamyl | H | F | H | F |
| I-776 | 5-phenyl-penta-2,4-dienyl | H | F | H | F |
| I-777 | 4-isopropyloxycarbonylamino-cinnamyl | H | F | H | F |
| I-778 | 3-naphthalen-2-yl-allyl | H | F | H | F |
| I-779 | 3-(5-trifluoromethyl-pyridin-2-yl)-allyl | H | F | H | F |
| I-780 | 3-(5-chloro-pyridin-2-yl)-allyl | H | F | H | F |
| I-781 | 3-pyridin-4-yl-allyl | H | F | H | F |
| I-782 | 3-(2-Chloro-pyridin-4-yl)-allyl | H | F | H | F |
| I-783 | 4-chlorobenzyl | H | F | F | H |
| I-784 | Cinnamyl | H | F | F | H |
| I-785 | 4-chlorocinnamyl | H | F | F | H |
| I-786 | 4-fluorocinnamyl | H | F | F | H |
| I-787 | 4-bromocinnamyl | H | F | F | H |
| I-788 | 4-trifluoromethylcinnamyl | H | F | F | H |
| I-789 | 4-trifluoromethoxycinnamyl | H | F | F | H |
| I-790 | 4-pentafluoroethoxycinnamyl | H | F | F | H |
| I-791 | 4-methoxycinnamyl | H | F | F | H |
| I-792 | 4-ethoxycinnamyl | H | F | F | H |
| I-793 | 4-cyanocinnamyl | H | F | F | H |
| I-794 | 3-(6-chloro-pyridin-3-yl)-allyl | H | F | F | H |
| I-795 | 3-(4-chlorophenyl)-but-2-enyl | H | F | F | H |
| I-796 | 3-(4-chlorophenyl)-3-fluoro-allyl | H | F | F | H |
| I-797 | 3-chloro-4-fluoro-cinnamyl | H | F | F | H |
| I-798 | 3,5-dichloro-cinnamyl | H | F | F | H |
| I-799 | 5-phenyl-penta-2,4-dienyl | H | F | F | H |
| I-800 | 4-isopropyloxycarbonylamino-cinnamyl | H | F | F | H |
| I-801 | 3-naphthalen-2-yl-allyl | H | F | F | H |
| I-802 | 3-(5-trifluoromethyl-pyridin-2-yl)-allyl | H | F | F | H |
| I-803 | 3-(5-chloro-pyridin-2-yl)-allyl | H | F | F | H |
| I-804 | 3-pyridin-4-yl-allyl | H | F | F | H |
| I-805 | 3-(2-Chloro-pyridin-4-yl)-allyl | H | F | F | H |
| I-806 | 4-chlorobenzyl | H | F | F | H |
| I-807 | Cinnamyl | H | H | F | F |
| I-808 | 4-chlorocinnamyl | H | H | F | F |
| I-809 | 4-fluorocinnamyl | H | H | F | F |
| I-810 | 4-bromocinnamyl | H | H | F | F |
| I-811 | 4-trifluoromethylcinnamyl | H | H | F | F |
| I-812 | 4-trifluoromethoxycinnamyl | H | H | F | F |
| I-813 | 4-pentafluoroethoxycinnamyl | H | H | F | F |
| I-814 | 4-methoxycinnamyl | H | H | F | F |
| I-815 | 4-ethoxycinnamyl | H | H | F | F |
| I-816 | 4-cyanocinnamyl | H | H | F | F |
| I-817 | 3-(6-chloro-pyridin-3-yl)-allyl | H | H | F | F |
| I-818 | 3-(4-chlorophenyl)-but-2-enyl | H | H | F | F |
| I-819 | 3-(4-chlorophenyl)-3-fluoro-allyl | H | H | F | F |
| I-820 | 3-chloro-4-fluoro-cinnamyl | H | H | F | F |
| I-821 | 3,5-dichloro-cinnamyl | H | H | F | F |
| I-822 | 5-phenyl-penta-2,4-dienyl | H | H | F | F |
| I-823 | 4-isopropyloxycarbonylamino-cinnamyl | H | H | F | F |
| I-824 | 3-naphthalen-2-yl-allyl | H | H | F | F |
| I-825 | 3-(5-trifluoromethyl-pyridin-2-yl)-allyl | H | H | F | F |
| I-826 | 3-(5-chloro-pyridin-2-yl)-allyl | H | H | F | F |
| I-827 | 3-pyridin-4-yl-allyl | H | H | F | F |
| I-828 | 3-(2-Chloro-pyridin-4-yl)-allyl | H | H | F | F |
| I-829 | 4-chlorobenzyl | H | H | Cl | Cl |
| I-830 | Cinnamyl | H | H | Cl | Cl |
| I-831 | 4-chlorocinnamyl | H | H | Cl | Cl |
| I-832 | 4-fluorocinnamyl | H | H | Cl | Cl |
| I-833 | 4-bromocinnamyl | H | H | Cl | Cl |
| I-834 | 4-trifluoromethylcinnamyl | H | H | Cl | Cl |
| I-835 | 4-trifluoromethoxycinnamyl | H | H | Cl | Cl |
| I-836 | 4-pentafluoroethoxycinnamyl | H | H | Cl | Cl |
| I-837 | 4-methoxycinnamyl | H | H | Cl | Cl |
| I-838 | 4-ethoxycinnamyl | H | H | Cl | Cl |
| I-839 | 4-cyanocinnamyl | H | H | Cl | Cl |
| I-840 | 3-(6-chloro-pyridin-3-yl)-allyl | H | H | Cl | Cl |
| I-841 | 3-(4-chlorophenyl)-but-2-enyl | H | H | Cl | Cl |
| I-842 | 3-(4-chlorophenyl)-3-fluoro-allyl | H | H | Cl | Cl |
| I-843 | 3-chloro-4-fluoro-cinnamyl | H | H | Cl | Cl |
| I-844 | 3,5-dichloro-cinnamyl | H | H | Cl | Cl |
| I-845 | 5-phenyl-penta-2,4-dienyl | H | H | Cl | Cl |

TABLE 1-continued

| Compound No | R⁸ | R⁴ᵃ | R⁴ᵇ | R⁴ᶜ | R⁴ᵈ |
|---|---|---|---|---|---|
| I-846 | 4-isopropyloxycarbonylamino-cinnamyl | H | H | Cl | Cl |
| I-847 | 3-naphthalen-2-yl-allyl | H | H | Cl | Cl |
| I-848 | 3-(5-trifluoromethyl-pyridin-2-yl)-allyl | H | H | Cl | Cl |
| I-849 | 3-(5-chloro-pyridin-2-yl)-allyl | H | H | Cl | Cl |
| I-850 | 3-pyridin-4-yl-allyl | H | H | Cl | Cl |
| I-851 | 3-(2-Chloro-pyridin-4-yl)-allyl | H | H | Cl | Cl |
| I-852 | 4-chlorobenzyl | H | Cl | Cl | H |
| I-853 | Cinnamyl | H | Cl | Cl | H |
| I-854 | 4-chlorocinnamyl | H | Cl | Cl | H |
| I-855 | 4-fluorocinnamyl | H | Cl | Cl | H |
| I-856 | 4-bromocinnamyl | H | Cl | Cl | H |
| I-857 | 4-trifluoromethylcinnamyl | H | Cl | Cl | H |
| I-858 | 4-trifluoromethoxycinnamyl | H | Cl | Cl | H |
| I-859 | 4-pentafluoroethoxycinnamyl | H | Cl | Cl | H |
| I-860 | 4-methoxycinnamyl | H | Cl | Cl | H |
| I-861 | 4-ethoxycinnamyl | H | Cl | Cl | H |
| I-862 | 4-cyanocinnamyl | H | Cl | Cl | H |
| I-863 | 3-(6-chloro-pyridin-3-yl)-allyl | H | Cl | Cl | H |
| I-864 | 3-(4-chlorophenyl)-but-2-enyl | H | Cl | Cl | H |
| I-865 | 3-(4-chlorophenyl)-3-fluoro-allyl | H | Cl | Cl | H |
| I-866 | 3-chloro-4-fluoro-cinnamyl | H | Cl | Cl | H |
| I-867 | 3,5-dichloro-cinnamyl | H | Cl | Cl | H |
| I-868 | 5-phenyl-penta-2,4-dienyl | H | Cl | Cl | H |
| I-869 | 4-isopropyloxycarbonylamino-cinnamyl | H | Cl | Cl | H |
| I-870 | 3-naphthalen-2-yl-allyl | H | Cl | Cl | H |
| I-871 | 3-(5-trifluoromethyl-pyridin-2-yl)-allyl | H | Cl | Cl | H |
| I-872 | 3-(5-chloro-pyridin-2-yl)-allyl | H | Cl | Cl | H |
| I-873 | 3-pyridin-4-yl-allyl | H | Cl | Cl | H |
| I-874 | 3-(2-Chloro-pyridin-4-yl)-allyl | H | Cl | Cl | H |
| I-875 | 4-chlorobenzyl | H | Cl | H | Cl |
| I-876 | Cinnamyl | H | Cl | H | Cl |
| I-877 | 4-chlorocinnamyl | H | Cl | H | Cl |
| I-878 | 4-fluorocinnamyl | H | Cl | H | Cl |
| I-879 | 4-bromocinnamyl | H | Cl | H | Cl |
| I-880 | 4-trifluoromethylcinnamyl | H | Cl | H | Cl |
| I-881 | 4-trifluoromethoxycinnamyl | H | Cl | H | Cl |
| I-882 | 4-pentafluoroethoxycinnamyl | H | Cl | H | Cl |
| I-883 | 4-methoxycinnamyl | H | Cl | H | Cl |
| I-884 | 4-ethoxycinnamyl | H | Cl | H | Cl |
| I-885 | 4-cyanocinnamyl | H | Cl | H | Cl |
| I-886 | 3-(6-chloro-pyridin-3-yl)-allyl | H | Cl | H | Cl |
| I-887 | 3-(4-chlorophenyl)-but-2-enyl | H | Cl | H | Cl |
| I-888 | 3-(4-chlorophenyl)-3-fluoro-allyl | H | Cl | H | Cl |
| I-889 | 3-chloro-4-fluoro-cinnamyl | H | Cl | H | Cl |
| I-890 | 3,5-dichloro-cinnamyl | H | Cl | H | Cl |
| I-891 | 5-phenyl-penta-2,4-dienyl | H | Cl | H | Cl |
| I-892 | 4-isopropyloxycarbonylamino-cinnamyl | H | Cl | H | Cl |
| I-893 | 3-naphthalen-2-yl-allyl | H | Cl | H | Cl |
| I-894 | 3-(5-trifluoromethyl-pyridin-2-yl)-allyl | H | Cl | H | Cl |
| I-895 | 3-(5-chloro-pyridin-2-yl)-allyl | H | Cl | H | Cl |
| I-896 | 3-pyridin-4-yl-allyl | H | Cl | H | Cl |
| I-897 | 3-(2-Chloro-pyridin-4-yl)-allyl | H | Cl | H | Cl |

Table II provides 897 compounds of formula Ib

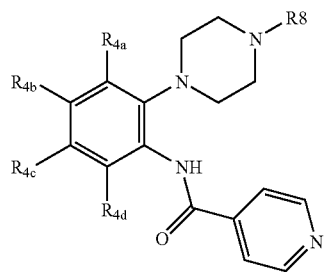

(Ib)

wherein the values of $R^8$, $R^{4a}$, $R^{4b}$, $R^{4c}$ and $R^{4d}$ are given in Table 1.

Table III provides 897 compounds of formula Ic

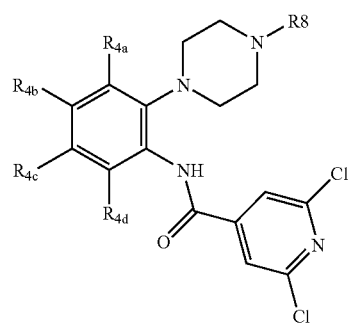

(Ic)

wherein the values of $R^8$, $R^{4a}$, $R^{4b}$, $R^{4c}$ and $R^{4d}$ are given in Table 1

Table IV provides 897 compounds of formula Id

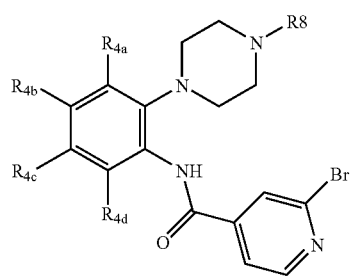

(Id)

wherein the values of $R^8$, $R^{4a}$, $R^{4b}$, $R^{4c}$ and $R^{4d}$ are given in Table 1

Table V provides 897 compounds of formula Ie

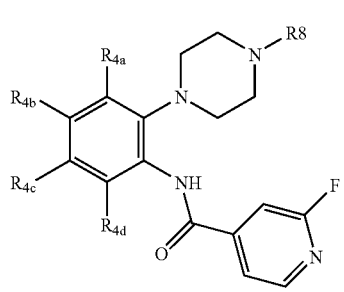
(Ie)

wherein and the values of $R^8$, $R^{4a}$, $R^{4b}$, $R^{4c}$ and $R^{4d}$ are given in Table 1

Table VI provides 897 compounds of formla If

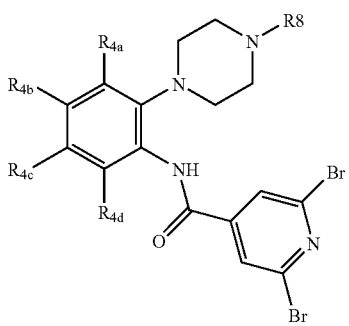
(If)

wherein the values of $R^8$, $R^{4a}$, $R^{4b}$, $R^{4c}$ and $R^{4d}$ are given in Table 1

Table VII provides 897 compounds of formula Ig

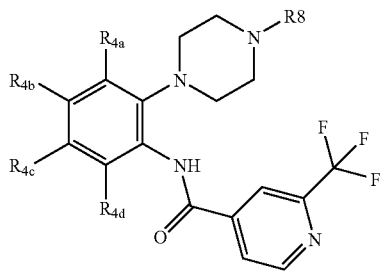
(Ig)

wherein the values of $R^8$, $R^{4a}$, $R^{4b}$, $R^{4c}$ and $R^{4d}$ are given in Table 1.

Table VIII provides 897 compounds of formula Ih

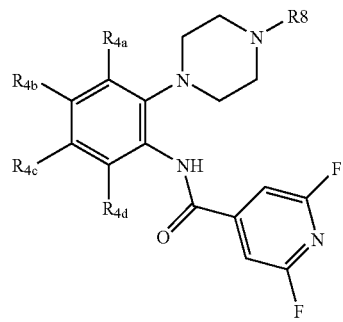
(Ih)

wherein the values of $R^8$, $R^{4a}$, $R^{4b}$, $R^{4c}$ and $R^{4d}$ are given in Table 1

Table IX provides 897 compounds of formula Ii

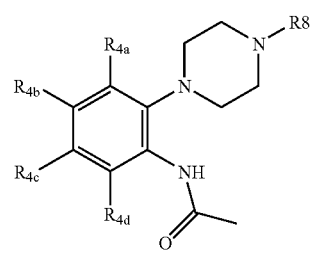
(Ii)

wherein the values of $R^8$, $R^{4a}$, $R^{4b}$, $R^{4c}$ and $R^{4d}$ are given in Table 1.

Table X provides 897 compounds of formula Ij

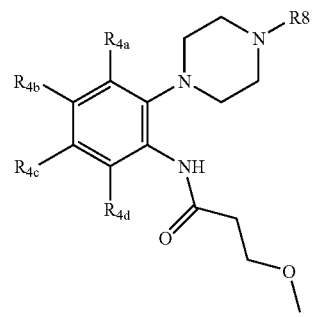
(Ij)

wherein the values of $R^8$, $R^{4a}$, $R^{4b}$, $R^{4c}$ and $R^{4d}$ are given in Table 1.

Table XI provides 897 compounds of formula Ik

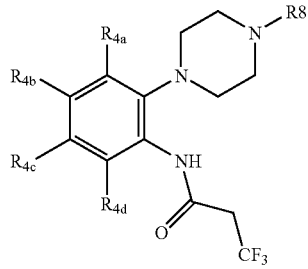

wherein the values of $R^8$, $R^{4a}$, $R^{4b}$, $R^{4c}$ and $R^{4d}$ are given in Table 1.

Table XII provides 897 compounds of formula Il

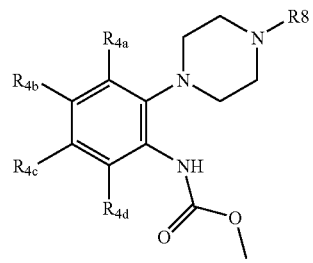

wherein the values of $R^8$, $R^{4a}$, $R^{4b}$, $R^{4c}$ and $R^{4d}$ are given in Table 1.

Table XIII provides 897 compounds of formula Im

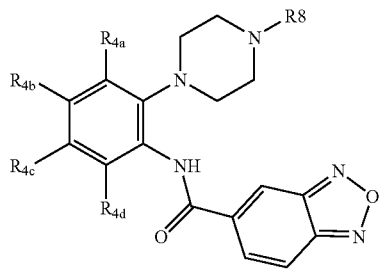

wherein the values of $R^8$, $R^{4a}$, $R^{4b}$, $R^{4c}$ and $R^{4d}$ are given in Table 1.

Table XIV provides 897 compounds of formula In

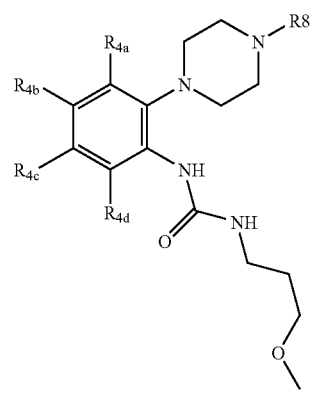

wherein the values of $R^8$, $R^{4a}$, $R^{4b}$, $R^{4c}$ and $R^{4d}$ are given in Table 1.

Table XV provides 897 compounds of formula Io

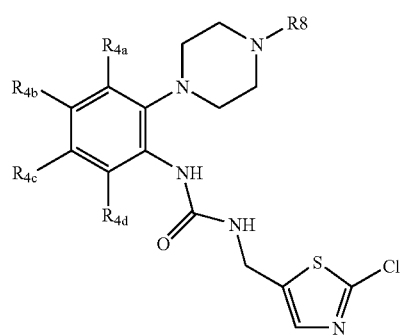

wherein the values of $R^8$, $R^{4a}$, $R^{4b}$, $R^{4c}$ and $R^{4d}$ are given in Table 1.

Table XVI provides 897 compounds of formula Ip

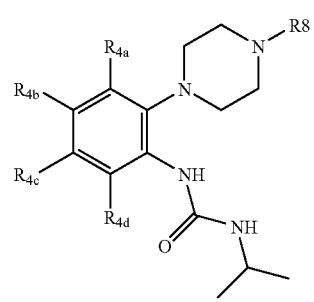

wherein the values of $R^8$, $R^{4a}$, $R^{4b}$, $R^{4c}$ and $R^{4d}$ are given in Table 1.

Table XVII provides 897 compounds of formula Iq

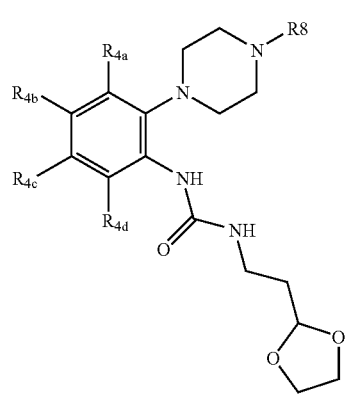

(Iq)

wherein the values of $R^8$, $R^{4a}$, $R^{4b}$, $R^{4c}$ and $R^{4d}$ are given in Table 1.

Table XVIII provides 897 compounds of formula Ir

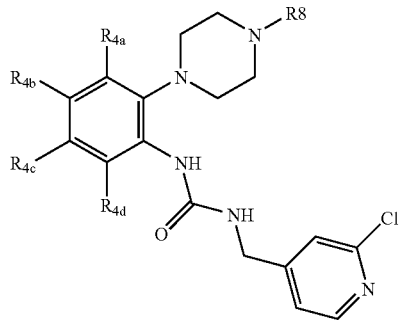

(Ir)

wherein the values of $R^8$, $R^{4a}$, $R^{4b}$, $R^{4c}$ and $R^{4d}$ are given in Table 1.

Table XIX provides 897 compounds of formula Is

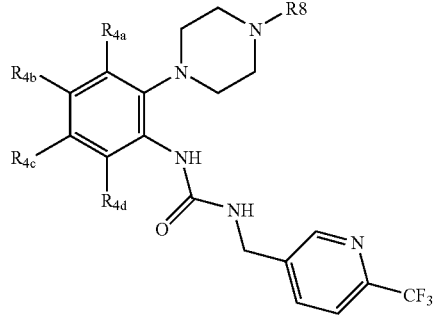

(Is)

wherein the values of $R^8$, $R^{4a}$, $R^{4b}$, $R^{4c}$ and $R^{4d}$ are given in Table 1.

Table XX provides 897 compounds of formula It

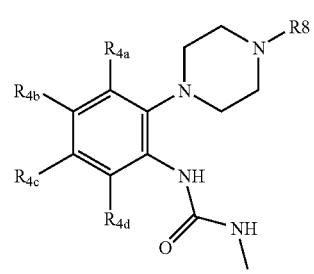

(It)

wherein the values of $R^8$, $R^{4a}$, $R^{4b}$, $R^{4c}$ and $R^{4d}$ are given in Table 1.

Table XXI provides 897 compounds of formula Iu

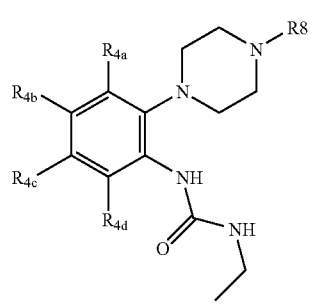

(Iu)

wherein the values of $R^8$, $R^{4a}$, $R^{4b}$, $R^{4c}$ and $R^{4d}$ are given in Table 1.

Table XXII provides 897 compounds of formula Iv

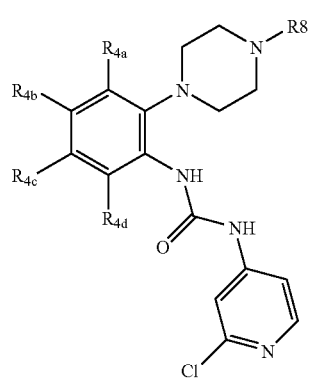

(Iv)

wherein the values of $R^8$, $R^{4a}$, $R^{4b}$, $R^{4c}$ and $R^{4d}$ are given in Table 1.

Table XXIII provides 897 compounds of formula Iw

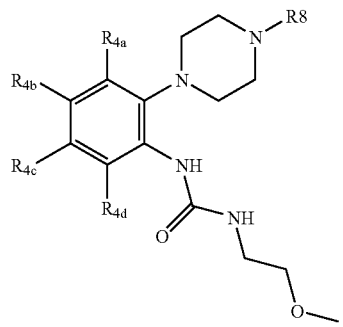

(Iw)

wherein the values of $R^8$, $R^{4a}$, $R^{4b}$, $R^{4c}$ and $R^{4d}$ are given in Table 1.

Table XXIV provides 110 compounds of formula Ix

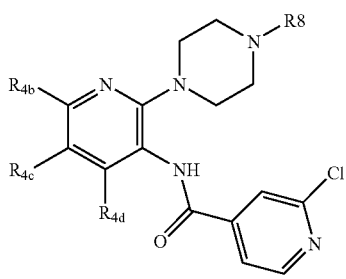

(Ix)

wherein the values of $R^8$, $R^{4b}$, $R^{4c}$ and $R^{4d}$ are given in Table 24.

TABLE 24

| Compound No | $R^8$ | $R^{4b}$ | $R^{4c}$ | $R^{4d}$ |
|---|---|---|---|---|
| XXIV-1 | Cinnamyl | H | H | H |
| XXIV-2 | 4-chlorocinnamyl | H | H | H |
| XXIV-3 | 4-fluorocinnamyl | H | H | H |
| XXIV-4 | 4-bromocinnamyl | H | H | H |
| XXIV-5 | 4-trifluoromethylcinnamyl | H | H | H |
| XXIV-6 | 4-trifluoromethoxycinnamyl | H | H | H |
| XXIV-7 | 4-pentafluoroethoxycinnamyl | H | H | H |
| XXIV-8 | 4-methoxycinnamyl | H | H | H |
| XXIV-9 | 4-ethoxycinnamyl | H | H | H |
| XXIV-10 | 4-cyanocinnamyl | H | H | H |
| XXIV-11 | 3-(6-chloro-pyridin-3-yl)-allyl | H | H | H |
| XXIV-12 | 3-(4-chlorophenyl)-but-2-enyl | H | H | H |
| XXIV-13 | 3-(4-chlorophenyl)-3-fluoro-allyl | H | H | H |
| XXIV-14 | 3-chloro-4-fluoro-cinnamyl | H | H | H |
| XXIV-15 | 3,5-dichloro-cinnamyl | H | H | H |
| XXIV-16 | 5-phenyl-penta-2,4-dienyl | H | H | H |
| XXIV-17 | 4-isopropyloxycarbonylamino-cinnamyl | H | H | H |
| XXIV-18 | 3-naphthalen-2-yl-allyl | H | H | H |
| XXIV-19 | 3-(5-trifluoromethyl-pyridin-2-yl)-allyl | H | H | H |
| XXIV-20 | 3-(5-chloro-pyridin-2-yl)-allyl | H | H | H |
| XXIV-21 | 3-pyridin-4-yl-allyl | H | H | H |
| XXIV-22 | 3-(2-Chloro-pyridin-4-yl)-allyl | H | H | H |
| XXIV-23 | Cinnamyl | F | H | H |
| XXIV-24 | 4-chlorocinnamyl | F | H | H |
| XXIV-25 | 4-fluorocinnamyl | F | H | H |
| XXIV-26 | 4-bromocinnamyl | F | H | H |
| XXIV-27 | 4-trifluoromethylcinnamyl | F | H | H |
| XXIV-28 | 4-trifluoromethoxycinnamyl | F | H | H |
| XXIV-29 | 4-pentafluoroethoxycinnamyl | F | H | H |
| XXIV-30 | 4-methoxycinnamyl | F | H | H |
| XXIV-31 | 4-ethoxycinnamyl | F | H | H |
| XXIV-32 | 4-cyanocinnamyl | F | H | H |
| XXIV-33 | 3-(6-chloro-pyridin-3-yl)-allyl | F | H | H |
| XXIV-34 | 3-(4-chlorophenyl)-but-2-enyl | F | H | H |
| XXIV-35 | 3-(4-chlorophenyl)-3-fluoro-allyl | F | H | H |
| XXIV-36 | 3-chloro-4-fluoro-cinnamyl | F | H | H |
| XXIV-37 | 3,5-dichloro-cinnamyl | F | H | H |
| XXIV-38 | 5-phenyl-penta-2,4-dienyl | F | H | H |
| XXIV-39 | 4-isopropyloxycarbonylamino-cinnamyl | F | H | H |
| XXIV-40 | 3-naphthalen-2-yl-allyl | F | H | H |
| XXIV-41 | 3-(5-trifluoromethyl-pyridin-2-yl)-allyl | F | H | H |
| XXIV-42 | 3-(5-chloro-pyridin-2-yl)-allyl | F | H | H |
| XXIV-43 | 3-pyridin-4-yl-ayl | F | H | H |
| XXIV-44 | 3-(2-Chloro-pyridin-4-yl)-allyl | F | H | H |
| XXIV-45 | Cinnamyl | Cl | H | H |
| XXIV-46 | 4-chlorocinnamyl | Cl | H | H |
| XXIV-47 | 4-fluorocinnamyl | Cl | H | H |
| XXIV-48 | 4-bromocinnamyl | Cl | H | H |
| XXIV-49 | 4-trifluoromethylcinnamyl | Cl | H | H |
| XXIV-50 | 4-trifluoromethoxycinnamyl | Cl | H | H |
| XXIV-51 | 4-pentafluoroethoxycinnamyl | Cl | H | H |
| XXIV-52 | 4-methoxycinnamyl | Cl | H | H |
| XXIV-53 | 4-ethoxycinnamyl | Cl | H | H |
| XXIV-54 | 4-cyanocinnamyl | Cl | H | H |
| XXIV-55 | 3-(6-chloro-pyridin-3-yl)-allyl | Cl | H | H |
| XXIV-56 | 3-(4-chlorophenyl)-but-2-enyl | Cl | H | H |
| XXIV-57 | 3-(4-chlorophenyl)-3-fluoro-allyl | Cl | H | H |
| XXIV-58 | 3-chloro-4-fluoro-cinnamyl | Cl | H | H |
| XXIV-59 | 3,5-dichloro-cinnamyl | Cl | H | H |
| XXIV-60 | 5-phenyl-penta-2,4-dienyl | Cl | H | H |
| XXIV-61 | 4-isopropyloxycarbonylamino-cinnamyl | Cl | H | H |
| XXIV-62 | 3-naphthalen-2-yl-allyl | Cl | H | H |
| XXIV-63 | 3-(5-trifluoromethyl-pyridin-2-yl)-allyl | Cl | H | H |
| XXIV-64 | 3-(5-chloro-pyridin-2-yl)-allyl | Cl | H | H |
| XXIV-65 | 3-pyridin-4-yl-allyl | Cl | H | H |
| XXIV-66 | 3-(2-Chloro-pyridin-4-yl)-allyl | Cl | H | H |
| XXIV-67 | Cinnamyl | H | F | H |
| XXIV-68 | 4-chlorocinnamyl | H | F | H |
| XXIV-69 | 4-fluorocinnamyl | H | F | H |
| XXIV-70 | 4-bromocinnamyl | H | F | H |
| XXIV-71 | 4-trifluoromethylcinnamyl | H | F | H |
| XXIV-72 | 4-trifluoromethoxycinnamyl | H | F | H |
| XXIV-73 | 4-pentafluoroethoxycinnamyl | H | F | H |
| XXIV-74 | 4-methoxycinnamyl | H | F | H |
| XXIV-75 | 4-ethoxycinnamyl | H | F | H |
| XXIV-76 | 4-cyanocinnamyl | H | F | H |
| XXIV-77 | 3-(6-chloro-pyridin-3-yl)-allyl | H | F | H |
| XXIV-78 | 3-(4-chlorophenyl)-but-2-enyl | H | F | H |
| XXIV-79 | 3-(4-chlorophenyl)-3-fluoro-allyl | H | F | H |
| XXIV-80 | 3-chloro-4-fluoro-cinnamyl | H | F | H |
| XXIV-81 | 3,5-dichloro-cinnamyl | H | F | H |
| XXIV-82 | 5-phenyl-penta-2,4-dienyl | H | F | H |
| XXIV-83 | 4-isopropyloxycarbonylamino-cinnamyl | H | F | H |
| XXIV-84 | 3-naphthalen-2-yl-allyl | H | F | H |
| XXIV-85 | 3-(5-trifluoromethyl-pyridin-2-yl)-allyl | H | F | H |
| XXIV-86 | 3-(5-chloro-pyridin-2-yl)-allyl | H | F | H |
| XXIV-87 | 3-pyridin-4-yl-allyl | H | F | H |
| XXIV-88 | 3-(2-Chloro-pyridin-4-yl)-allyl | H | F | H |
| XXIV-89 | Cinnamyl | H | Cl | H |
| XXIV-90 | 4-chlorocinnamyl | H | Cl | H |
| XXIV-91 | 4-fluorocinnamyl | H | Cl | H |
| XXIV-92 | 4-bromocinnamyl | H | Cl | H |

TABLE 24-continued

| Compound No | R⁸ | R⁴ᵇ | R⁴ᶜ | R⁴ᵈ |
|---|---|---|---|---|
| XXIV-93 | 4-trifluoromethylcinnamyl | H | Cl | H |
| XXIV-94 | 4-trifluoromethoxycinnamyl | H | Cl | H |
| XXIV-95 | 4-pentafluoroethoxycinnamyl | H | Cl | H |
| XXIV-96 | 4-methoxycinnamyl | H | Cl | H |
| XXIV-97 | 4-ethoxycinnamyl | H | Cl | H |
| XXIV-98 | 4-cyanocinnamyl | H | Cl | H |
| XXIV-99 | 3-(6-chloro-pyridin-3-yl)-allyl | H | Cl | H |
| XXIV-100 | 3-(4-chlorophenyl)-but-2-enyl | H | Cl | H |
| XXIV-101 | 3-(4-chlorophenyl)-3-fluoro-allyl | H | Cl | H |
| XXIV-102 | 3-chloro-4-fluoro-cinnamyl | H | Cl | H |
| XXIV-103 | 3,5-dichloro-cinnamyl | H | Cl | H |
| XXIV-104 | 5-phenyl-penta-2,4-dienyl | H | Cl | H |
| XXIV-105 | 4-isopropyloxycarbonylamino-cinnamyl | H | Cl | H |
| XXIV-106 | 3-naphthalen-2-yl-allyl | H | Cl | H |
| XXIV-107 | 3-(5-trifluoromethyl-pyridin-2-yl)-allyl | H | Cl | H |
| XXIV-108 | 3-(5-chloro-pyridin-2-yl)-allyl | H | Cl | H |
| XXIV-109 | 3-pyridin-4-yl-allyl | H | Cl | H |
| XXIV-110 | 3-(2-Chloro-pyridin-4-yl)-allyl | H | Cl | H |

Table XXV provides 897 compounds of formula Iy

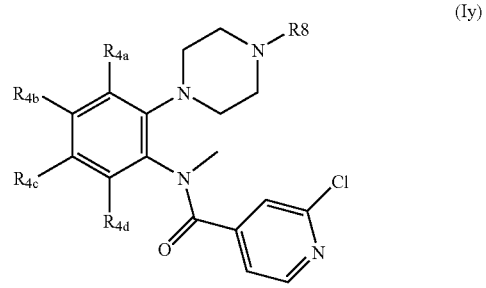

wherein the values of $R^8$, $R^{4a}$, $R^{4b}$, $R^{4c}$ and $R^{4d}$ are given in Table 1.

The compounds of the invention may be made by a variety of methods. For example they may be prepared according to the reactions of Scheme 1.

SCHEME 1

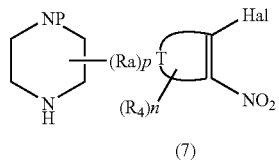

(7)

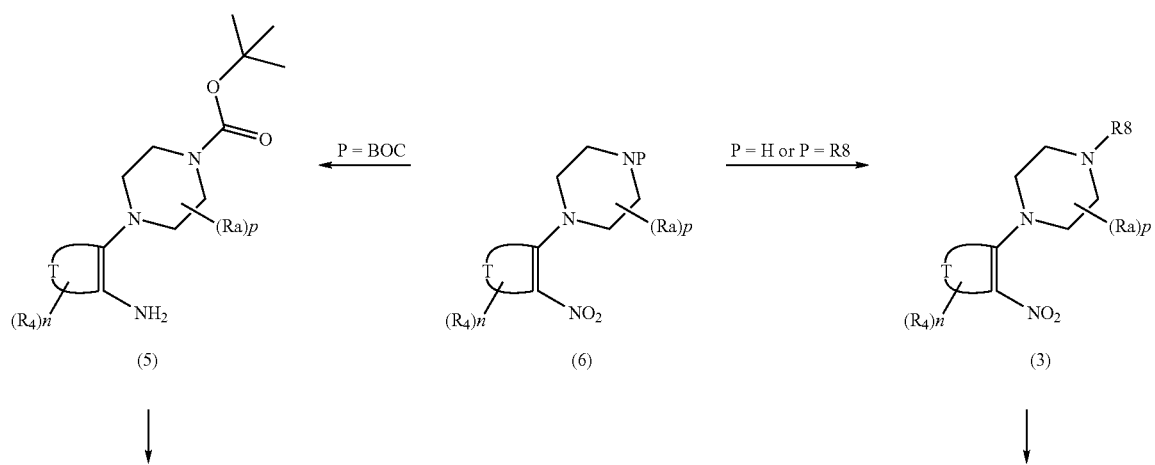

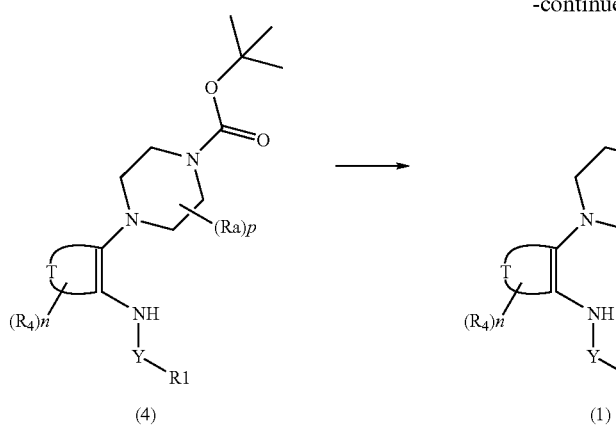

(4)    (1)    (2)

Thus a compound of formula 1 may be obtained from a compound of formula 2 by reaction with a suitable electrophilic species. Compounds of formula 1 where Y is a carbonyl group may be formed by the reaction of compounds of formula 2 with a carboxylic acid derivative of formula R1-C(O)—Z where Z is chloride, hydroxy, alkoxy or acyloxy at a temperature between 0° C. and 150° C. optionally in an organic solvent such as dichloromethane, chloroform or 1,2-dichloroethane, optionally in the presence of a tertiary amine base such as triethylamine or diisopropylethylamine and optionally in the presence of a coupling agent such as dicyclohexylcarbodiimide. Compounds of formula 1 where Y is a carbonyl group and R1 is an amino substituent of formula R'—NH— may be formed by the reaction of compounds of formula 4 with an isocyanate of formula R'—N=C=O under similar conditions. Compounds of formula 1 where Y is a group of formula $S(O)_m$ may be formed from compounds of formula 2 by treatment with compounds of formula of R1-S(O)$_m$—Cl under similar conditions. Compounds of formula 1 where Y is a thiocarbonyl group and R1 is an amino substituent of formula R'—NH— may be formed by the reaction of compounds of formula 2 with an isothiocyanate of formula R'—N=C=S under similar conditions.

Alternatively compounds of formula 1 where Y is a thiocarbonyl group and R1 is a carbon substituent may be formed by treatment of compounds of formula 1 where Y is a carbonyl group and R1 is a carbon substituent with a suitable thionating agent such as Lawesson's reagent.

In the above procedures, acid derivatives of the formula R1-C(O)-Z, isocyanates of formula R'—N=C=O, isothiocyanates of formula R'—N=C=S and sulfur electrophiles of formula R1-S(O)$_q$—Cl are either known compounds or may be formed from known compounds by known methods by a person skilled in the art.

Compounds of formula 2 may be prepared from compounds of formula 3 by reduction of the nitro group, according to known methods by a person skilled in the art.

Compounds of formula 3 may be obtained from compounds of formula 6 where P is H by reaction with an alkylating agent of the formula R8-L, where L is chloride, bromide, iodide or a sulfonate (e.g. mesylate or tosylate) or similar leaving group at a temperature of between ambient temperature and 100° C., typically 65° C., in an organic solvent such as dichloromethane, chloroform or 1,2-dichloroethane in the presence of a tertiary amine base such as triethylamine or diisopropylethylamine and optionally catalysed by halide salts such as sodium iodide, potassium iodide or tetrabutylammonium iodide. Alternatively, a compound of formula 6 where P is H may be reacted with an aldehyde of the formula RzCHO at a temperature between ambient temperature and 100° C. in an organic solvent such as tetrahydrofuran or ethanol or mixtures of solvents in the presence of a reducing agent such as borane-pyridine complex, sodium borohydride, sodium (triacetoxy)borohydride, sodium cyanoborohydride or such like, to produce a compound of formula 3 where R8 is CH$_2$-Rz.

Alternatively, a compound of formula 1 may be obtained from a compound of formula 4 by (1) reaction with an acid such as trifluoroacetic acid at ambient temperature in an organic solvent such as dichloromethane, chloroform or 1,2-dichloroethane followed by neutralisation of the reaction mixture with an aqueous solution of an inorganic base such as sodium carbonate, sodium bicarbonate or similar compound; then (2) reaction with an alkylating agent or an aldehyde as described above.

Compounds of formula 4 may be formed by reaction of compounds of formula 5 with a suitable electrophile, as described above in the method for converting compounds of formula 2 to compounds of formula 1.

Compounds of formula 5 may be obtained from compounds of formula 6 where P is t-butoxycarbonyl by reduction of the nitro group according to known methods.

Compounds of formula 6 may be obtained from compounds of formula 7 by reaction with piperazine (P=H) or N-BOC-piperazine (P=t-butoxycarbonyl) at a temperature between 0° C. and 180° C., in a solvent such as dichloromethane, 1,2-dichloroethane, acetonitrile, dimethylformamide or dimethylsulfoxide in the presence of a base such as triethylamine, diisopropylethylamine or potassium carbonate or in the absence of base.

Compounds of formula 5, formula 6 and formula 7 are known compounds or may be made from known compounds by known methods.

Certain compounds of formula 2, formula 3 and formula 4 are novel and as such form a further aspect of the invention.

The skilled person will readily recognise that it is possible to convert one compound of formula 1 wherein R2 is H or an intermediate of Scheme 1 to other compounds of formula I. Examples of such transformations are given in Schemes 2, 3 and 4 in which the R groups have the meanings as defined for a compound of formula I above.

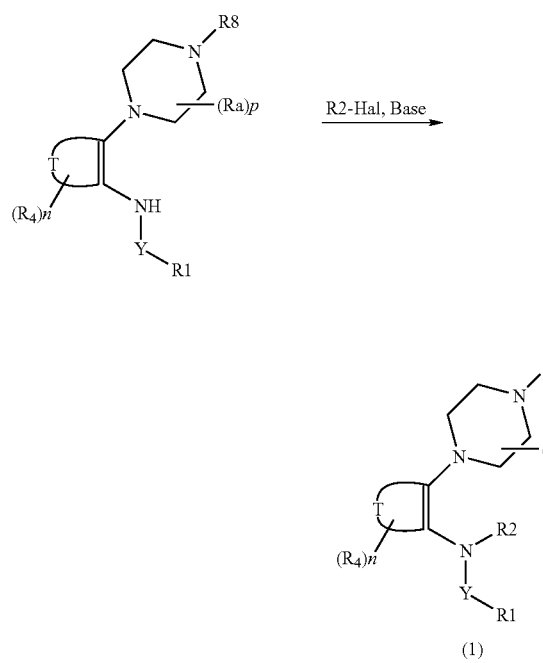
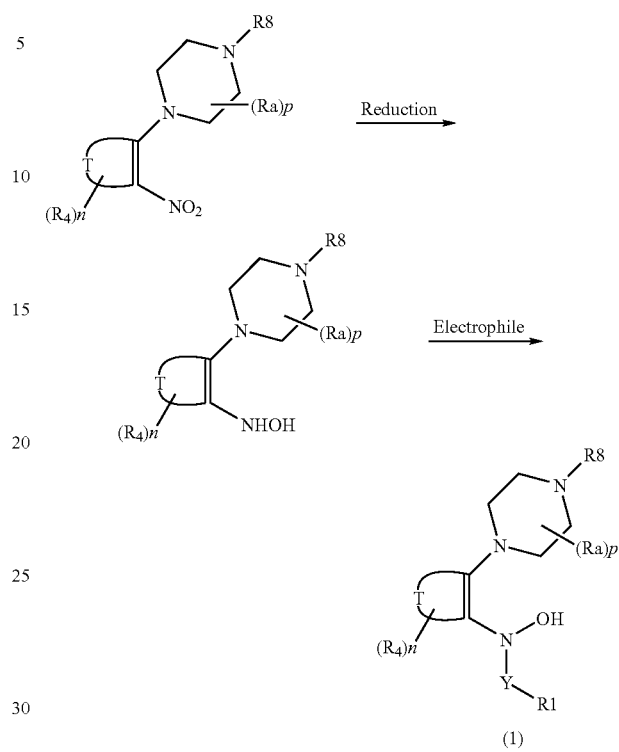
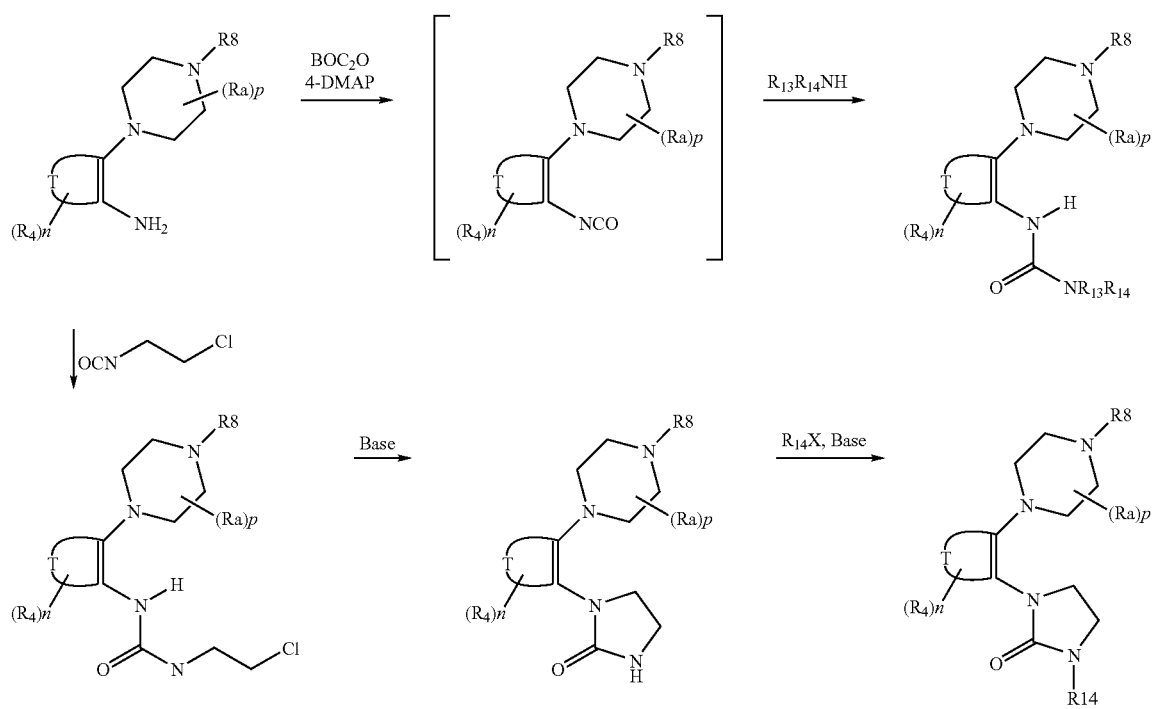

The compounds of formula (I) can be used to combat and control infestations of insect pests such as Lepidoptera, Diptera, Hemiptera, Thysanoptera, Orthoptera, Dictyoptera, Coleoptera, Siphonaptera, Hymenoptera and Isoptera and also other invertebrate pests, for example, acarine, nematode and mollusc pests. Insects, acarines, nematodes and molluscs are hereinafter collectively referred to as pests. The pests which may be combated and controlled by the use of the invention compounds include those pests associated with agriculture (which term includes the growing of crops for food and fibre products), horticulture and animal husbandry, companion animals, forestry and the storage of products of vegetable origin (such as fruit, grain and timber); those pests associated with the damage of man-made structures and the transmission of diseases of man and animals; and also nuisance pests (such as flies).

Examples of pest species which may be controlled by the compounds of formula (I) include: *Myzus persicae* (aphid), *Aphis gossypii* (aphid), *Aphis fabae* (aphid), *Lygus* spp. (capsids), *Dysdercus* spp. (capsids), *Nilaparvata lugens* (planthopper), *Nephotettixc incticeps* (leafhopper), *Nezara* spp. (stinkbugs), *Euschistus* spp. (stinkbugs), *Leptocorisa* spp. (stinkbugs), *Frankliniella occidentalis* (thrip), *Thrips* spp. (thrips), *Leptinotarsa decemlineata* (Colorado potato beetle), *Anthonomus grandis* (boll weevil), *Aonidiella* spp. (scale insects), *Trialeurodes* spp. (white flies), *Bemisia tabaci* (white fly), *Ostrinia nubilalis* (European corn borer), *Spodoptera littoralis* (cotton leafworm), *Heliothis virescens* (tobacco budworm), *Helicoverpa armigera* (cotton bollworm), *Helicoverpa zea* (cotton bollworm), *Sylepta derogata* (cotton leaf roller), *Pieris brassicae* (white butterfly), *Plutella xylostella* (diamond back moth), *Agrotis* spp. (cutworms), *Chilo suppressalis* (rice stem borer), *Locusta migratoria* (locust), *Chortiocetes terminifera* (locust), *Diabrotica* spp. (rootworms), *Panonychus ulmi* (European red mite), *Panonychus citri* (citrus red mite), *Tetranychus urticae* (two-spotted spider mite), *Tetranychus cinnabarinus* (carmine spider mite), *Phyllocoptruta oleivora* (citrus rust mite), *Polyphagotarsonemus latus* (broad mite), *Brevipalpus* spp. (flat mites), *Boophilus microplus* (cattle tick), *Dermacentor variabilis* (American dog tick), *Ctenocephalides felis* (cat flea), *Liriomyza* spp. (leafminer), *Musca domestica* (housefly), *Aedes aegypti* (mosquito), *Anopheles* spp. (mosquitoes), *Culex* spp. (mosquitoes), *Lucillia* spp. (blowflies), *Blattella germanica* (cockroach), *Periplaneta americana* (cockroach), *Blatta orientalis* (cockroach), termites of the *Mastotermitidae* (for example *Mastotermes* spp.), the *Kalotermitidae* (for example *Neotermes* spp.), the Rhinoternitidae (for example *Coptotermes formosanus; Reticulitermes flavipes, R. speratu, R. virginicus, R. hesperus*, and *R. santonensis*) and the *Termitidae* (for example *Globitermes sulphureus*), *Solenopsis geminata* (fire ant), *Monomorium pharaonis* (pharaoh's ant), *Damalinia* spp. and *Linognathus* spp. (biting and sucking lice), *Meloidogyne* spp. (root knot nematodes), *Globodera* spp. and *Heterodera* spp. (cyst nematodes), *Pratylenchus* spp. (lesion nematodes), *Rhodopholus* spp. (banana burrowing nematodes), *Tylenchulus* spp. (citrus nematodes), *Haemonchus contortus* (barber pole worm), *Caenorhabditis elegans*-(vinegar eelworm), *Trichostrongylus* spp. (gastrointestinal nematodes) and *Deroceras reticulatum* (slug).

The invention therefore provides a method of combating and controlling insects, acarines, nematodes or molluscs which comprises applying an insecticidally, acaricidally, nematicidally or molluscicidally effective amount of a compound of formula (I), or a composition containing a compound of formula (I), to a pest, a locus of pest, or to a plant susceptible to attack by a pest, The compounds of formula (I) are preferably used against insects, acarines or nematodes.

The term "plant" as used herein includes seedlings, bushes and trees.

In order to apply a compound of formula (I) as an insecticide, acaricide, nematicide or molluscicide to a pest, a locus of pest, or to a plant susceptible to attack by a pest, a compound of formula (I) is usually formulated into a composition which includes, in addition to the compound of formula (I), a suitable inert diluent or carrier and, optionally, a surface active agent (SFA). SFAs are chemicals which are able to modify the properties of an interface (for example, liquid/solid, liquid/air or liquid/liquid interfaces) by lowering the interfacial tension and thereby leading to changes in other properties (for example dispersion, emulsification and wetting). It is preferred that all compositions (both solid and liquid formulations) comprise, by weight, 0.0001 to 95%, more preferably 1 to 85%, for example 5 to 60%, of a compound of formula (I). The composition is generally used for the control of pests such that a compound of formula (I) is applied at a rate of from 0.1 g to 10 kg per hectare, preferably from 1 g to 6 kg per hectare, more preferably from 1 g to 1 kg per hectare.

When used in a seed dressing, a compound of formula (I) is used at a rate of 0.0001 g to 10 g (for example 0.001 g or 0.05 g), preferably 0.005 g to 10 g, more preferably 0.005 g to 4 g, per kilogram of seed.

In another aspect the present invention provides an insecticidal, acaricidal, nematicidal or molluscicidal composition comprising an insecticidally, acaricidally, nematicidally or molluscicidally effective amount of a compound of formula (I) and a suitable carrier or diluent therefor. The composition is preferably an insecticidal, acaricidal, nematicidal or molluscicidal composition.

In a still further aspect the invention provides a method of combating and controlling pests at a locus which comprises treating the pests or the locus of the pests with an insecticidally, acaricidally, nematicidally or molluscicidally effective amount of a composition comprising a compound of formula (I). The compounds of formula (I) are preferably used against insects, acarines or nematodes.

The compositions can be chosen from a number of formulation types, including dustable powders (DP), soluble powders (SP), water soluble granules (SG), water dispersible granules (WG), wettable powders (WP), granules (GR) (slow or fast release), soluble concentrates (SL), oil miscible liquids (OL), ultra low volume liquids (UL), emulsifiable concentrates (EC), dispersible concentrates (DC), emulsions (both oil in water (EW) and water in oil (EO)), micro-emulsions (ME), suspension concentrates (SC), aerosols, fogging/smoke formulations, capsule suspensions (CS) and seed treatment formulations. The formulation type chosen in any instance will depend upon the particular purpose envisaged and the physical, chemical and biological properties of the compound of formula (I).

Dustable powders (DP) may be prepared by mixing a compound of formula (I) with one or more solid diluents (for example natural clays, kaolin, pyrophyllite, bentonite, alumina, montmorillonite, kieselguhr, chalk, diatomaceous earths, calcium phosphates, calcium and magnesium carbonates, sulphur, lime, flours, talc and other organic and inorganic solid carriers) and mechanically grinding the mixture to a fine powder.

Soluble powders (SP) may be prepared by mixing a compound of formula (I) with one or more water-soluble inorganic salts (such as sodium bicarbonate, sodium carbonate or magnesium sulphate) or one or more water-soluble organic solids (such as a polysaccharide) and, optionally, one or more wetting agents, one or more dispersing agents or a mixture of said agents to improve water dispersibility/solubility. The mixture is then ground to a fine powder. Similar compositions may also be granulated to form water soluble granules (SG).

Wettable powders (WP) may be prepared by mixing a compound of formula (I) with one or more solid diluents or carriers, one or more wetting agents and, preferably, one or more dispersing agents and, optionally, one or more suspending agents to facilitate the dispersion in liquids. The mixture is then ground to a fine powder. Similar compositions may also be granulated to form water dispersible granules (WG).

Granules (GR) may be formed either by granulating a mixture of a compound of formula (I) and one or more powdered solid diluents or carriers, or from pre-formed blank granules by absorbing a compound of formula (I) (or a solution thereof, in a suitable agent) in a porous granular material (such as pumice, attapulgite clays, fuller's earth, kieselguhr, diatomaceous earths or ground corn cobs) or by adsorbing a compound of formula (I) (or a solution thereof, in a suitable agent) on to a hard core material (such as sands, silicates, mineral carbonates, sulphates or phosphates) and drying if necessary. Agents which are commonly used to aid absorption or adsorption include solvents (such as aliphatic and aromatic petroleum solvents, alcohols, ethers, ketones and esters) and sticking agents (such as polyvinyl acetates, polyvinyl alcohols, dextrins, sugars and vegetable oils). One or more other additives may also be included in granules (for example an emulsifying agent, wetting agent or dispersing agent).

Dispersible Concentrates (DC) may be prepared by dissolving a compound of formula (I) in water or an organic solvent, such as a ketone, alcohol or glycol ether. These solutions may contain a surface active agent (for example to improve water dilution or prevent crystallisation in a spray tank).

Emulsifiable concentrates (EC) or oil-in-water emulsions (EW) may be prepared by dissolving a compound of formula (I) in an organic solvent (optionally containing one or more wetting agents, one or more emulsifying agents or a mixture of said agents). Suitable organic solvents for use in ECs include aromatic hydrocarbons (such as alkylbenzenes or alkylnaphthalenes, exemplified by SOLVESSO 100, SOLVESSO 150 and SOLVESSO 200; SOLVESSO is a Registered Trade Mark), ketones (such as cyclohexanone or methylcyclohexanone) and alcohols (such as benzyl alcohol, furfuryl alcohol or butanol), N-alkylpyrrolidones (such as N-methylpyrrolidone or N-octylpyrrolidone), dimethyl amides of fatty acids (such as $C_8$-$C_{10}$ fatty acid dimethylamide) and chlorinated hydrocarbons. An EC product may spontaneously emulsify on addition to water, to produce an emulsion with sufficient stability to allow spray application through appropriate equipment. Preparation of an EW involves obtaining a compound of formula (I) either as a liquid (if it is not a liquid at room temperature, it may be melted at a reasonable temperature, typically below 70° C.) or in solution (by dissolving it in an appropriate solvent) and then emulsiflying the resultant liquid or solution into water containing one or more SFAs, under high shear, to produce an emulsion. Suitable solvents for use in EWs include vegetable oils, chlorinated hydrocarbons (such as chlorobenzenes), aromatic solvents (such as alkylbenzenes or alkylnaphthalenes) and other appropriate organic solvents which have a low solubility in water.

Microemulsions (ME) may be prepared by mixing water with a blend of one or more solvents with one or more SFAs, to produce spontaneously a thermodynamically stable isotropic liquid formulation. A compound of formula (I) is present initially in either the water or the solvent/SFA blend. Suitable solvents for use in MEs include those hereinbefore described for use in ECs or in EWs. An ME may be either an oil-in-water or a water-in-oil system (which system is present may be determined by conductivity measurements) and may be suitable for mixing water-soluble and oil-soluble pesticides in the same formulation. An ME is suitable for dilution into water, either remaining as a microemulsion or forming a conventional oil-in-water emulsion.

Suspension concentrates (SC) may comprise aqueous or non-aqueous suspensions of finely divided insoluble solid particles of a compound of formula (I). SCs may be prepared by ball or bead milling the solid compound of formula (I) in a suitable medium, optionally with one or more dispersing agents, to produce a fine particle suspension of the compound. One or more wetting agents may be included in the composition and a suspending agent may be included to reduce the rate at which the particles settle. Alternatively, a compound of formula (I) may be dry milled and added to water, containing agents hereinbefore described, to produce the desired end product.

Aerosol formulations comprise a compound of formula (I) and a suitable propellant (for example n-butane). A compound of formula (I) may also be dissolved or dispersed in a suitable medium (for example water or a water miscible liquid, such as n-propanol) to provide compositions for use in non-pressurised, hand-actuated spray pumps.

A compound of formula (I) may be mixed in the dry state with a pyrotechnic mixture to form a composition suitable for generating, in an enclosed space, a smoke containing the compound.

Capsule suspensions (CS) may be prepared in a manner similar to the preparation of EW formulations but with an additional polymerisation stage such that an aqueous dispersion of oil droplets is obtained, in which each oil droplet is encapsulated by a polymeric shell and contains a compound of formula (I) and, optionally, a carrier or diluent therefor. The polymeric shell may be produced by either an interfacial polycondensation reaction or by a coacervation procedure. The compositions may provide for controlled release of the compound of formula (I) and they may be used for seed treatment. A compound of formula (I) may also be formulated in a biodegradable polymeric matrix to provide a slow, controlled release of the compound.

A composition may include one or more additives to improve the biological performance of the composition (for example by improving wetting, retention or distribution on surfaces; resistance to rain on treated surfaces; or uptake or mobility of a compound of formula (I)). Such additives include surface active agents, spray additives based on oils, for example certain mineral oils or natural plant oils (such as soy bean and rape seed oil), and blends of these with other bio-enhancing adjuvants (ingredients which may aid or modify the action of a compound of formula (I)).

A compound of formula (I) may also be formulated for use as a seed treatment, for example as a powder composition, including a powder for dry seed treatment (DS), a water soluble powder (SS) or a water dispersible powder for slurry treatment (WS), or as a liquid composition, including a flowable concentrate (FS), a solution (LS) or a capsule suspension (CS). The preparations of DS, SS, WS, FS and LS compositions are very similar to those of, respectively, DP, SP, WP, SC and DC compositions described above. Compositions for treating seed may include an agent for assisting the adhesion of the composition to the seed (for example a mineral oil or a film-forming barrier).

Wetting agents, dispersing agents and emulsifying agents may be surface SFAs of the cationic, anionic, amphoteric or non-ionic type.

Suitable SFAs of the cationic type include quaternary ammonium compounds (for example cetyltrimethyl ammonium bromide), imidazolines and amine salts.

Suitable anionic SFAs include alkali metals salts of fatty acids, salts of aliphatic monoesters of sulphuric acid (for example sodium lauryl sulphate), salts of sulphonated aromatic compounds (for example sodium dodecylbenzenesulphonate, calcium dodecylbenzenesulphonate, butylnaphthalene sulphonate and mixtures of sodium di-isopropyl- and tri-isopropyl-naphthalene sulphonates), ether sulphates, alcohol ether sulphates (for example sodium laureth-3-sulphate), ether carboxylates (for example sodium laureth-3-carboxylate), phosphate esters (products from the reaction between one or more fatty alcohols and phosphoric acid (predominately mono-esters) or phosphorus pentoxide (predominately di-esters), for example the reaction between lauryl alcohol and tetraphosphoric acid; additionally these products may be ethoxylated), sulphosuccinamates, paraffin or olefine sulphonates, taurates and lignosulphonates.

Suitable SFAs of the amphoteric type include betaines, propionates and glycinates.

Suitable SFAs of the non-ionic type include condensation products of alkylene oxides, such as ethylene oxide, propylene oxide, butylene oxide or mixtures thereof, with fatty alcohols (such as oleyl alcohol or cetyl alcohol) or with alkylphenols (such as octylphenol, nonylphenol or octylcresol); partial esters derived from long chain fatty acids or hexitol anhydrides; condensation products of said partial esters with ethylene oxide; block polymers (comprising ethylene oxide and propylene oxide); alkanolamides; simple esters (for example fatty acid polyethylene glycol esters); amine oxides (for example lauryl dimethyl amine oxide); and lecithins.

Suitable suspending agents include hydrophilic colloids (such as polysaccharides, polyvinylpyrrolidone or sodium carboxymethylcellulose) and swelling clays (such as bentonite or attapulgite).

A compound of formula (I) may be applied by any of the known means of applying pesticidal compounds. For example, it may be applied, formulated or unformulated, to the pests or to a locus of the pests (such as a habitat of the pests, or a growing plant liable to infestation by the pests) or to any part of the plant, including the foliage, stems, branches or roots, to the seed before it is planted or to other media in which plants are growing or are to be planted (such as soil surrounding the roots, the soil generally, paddy water or hydroponic culture systems), directly or it may be sprayed on, dusted on, applied by dipping, applied as a cream or paste formulation, applied as a vapour or applied through distribution or incorporation of a composition (such as a granular composition or a composition packed in a water-soluble bag) in soil or an aqueous environment.

A compound of formula (I) may also be injected into plants or sprayed onto vegetation using electrodynamic spraying techniques or other low volume methods, or applied by land or aerial irrigation systems.

Compositions for use as aqueous preparations (aqueous solutions or dispersions) are generally supplied in the form of a concentrate containing a high proportion of the active ingredient, the concentrate being added to water before use. These concentrates, which may include DCs, SCs, ECs, EWs, MEs SGs, SPs, WPs, WGs and CSs, are often required to withstand storage for prolonged periods and, after such storage, to be capable of addition to water to form aqueous preparations which remain homogeneous for a sufficient time to enable them to be applied by conventional spray equipment. Such aqueous preparations may contain varying amounts of a compound of formula (I) (for example 0.0001 to 10%, by weight) depending upon the purpose for which they are to be used.

A compound of formula (I) may be used in mixtures with fertilisers (for example nitrogen-, potassium- or phosphorus-containing fertilisers). Suitable formulation types include granules of fertiliser. The mixtures suitably contain up to 25% by weight of the compound of formula (I).

The invention therefore also provides a fertiliser composition comprising a fertiliser and a compound of formula (I).

The compositions of this invention may contain other compounds having biological activity, for example micronutrients or compounds having fungicidal activity or which possess plant growth regulating, herbicidal, insecticidal, nematicidal or acaricidal activity.

The compound of formula (I) may be the sole active ingredient of the composition or it may be admixed with one or more additional active ingredients such as a pesticide, fungicide, synergist, herbicide or plant growth regulator where appropriate. An additional active ingredient may: provide a composition having a broader spectrum of activity or increased persistence at a locus; synergise the activity or complement the activity (for example by increasing the speed of effect or overcoming repellency) of the compound of formula (I); or help to overcome or prevent the development of resistance to individual components. The particular additional active ingredient will depend upon the intended utility of the composition. Examples of suitable pesticides include the following:

a) Pyrethroids, such as permethrin, cypermethrin, fenvalerate, esfenvalerate, deltamethrin, cyhalothrin (in particular lambda-cyhalothrin), bifenthrin, fenpropathrin, cyfluthrin, tefluthrin, fish safe pyrethroids (for example ethofenprox), natural pyrethrin, tetramethrin, s-bioallethrin, fenfluthrin, prallethrin or 5-benzyl-3-furylmethyl-($E$)-(1R,3S)- 2,2-dimethyl-3-(2-oxothiolan-3-ylidenemethyl)cyclopropane carboxylate;

b) Organophosphates, such as, profenofos, sulprofos, acephate, methyl parathion, azinphos-methyl, demeton-s-methyl, heptenophos, thiometon, fenamiphos, monocrotophos, profenofos, triazophos, methamidophos, dimethoate, phosphamidon, malathion, chlorpyrifos, phosalone, terbufos, fensulfothion, fonofos, phorate, phoxim, pirimiphos-methyl, pirimiphos-ethyl, fenitrothion, fosthiazate or diazinon;

c) Carbamates (including aryl carbamates), such as pirimicarb, triazamate, cloethocarb, carbofuran, furathiocarb, ethiofencarb, aldicarb, thiofurox, carbosulfan, bendiocarb, fenobucarb, propoxur, methomyl or oxamyl;

d) Benzoyl ureas, such as diflubenzuron, triflumuron, hexaflumuron, flufenoxuron or chlorfluazuron;

e) Organic tin compounds, such as cyhexatin, fenbutatin oxide or azocyclotin;

f) Pyrazoles, such as tebufenpyrad and fenpyroximate;

g) Macrolides, such as avermectins or milbemycins, for example abamectin, emamectin benzoate, ivermectin, milbemycin, spinosad or azadirachtin;

h) Hormones or pheromones;

i) Organochlorine compounds such as endosulfan, benzene hexachloride, DDT, chlordane or dieldrin;

j) Amidines, such as chlordimeform or amitraz;

k) Fumigant agents, such as chloropicrin, dichloropropane, methyl bromide or metam;

l) Chloronicotinyl compounds such as imidacloprid, thiacloprid, acetamiprid, nitenpyram or thiamethoxam;

m) Diacylhydrazines, such as tebufenozide, chromafenozide or methoxyfenozide;
n) Diphenyl ethers, such as diofenolan or pyriproxifen;
o) Indoxacarb;
p) Chlorfenapyr; or
q) Pymetrozine.

In addition to the major chemical classes of pesticide listed above, other pesticides having particular targets may be employed in the composition, if appropriate for the intended utility of the composition. For instance, selective insecticides for particular crops, for example stemborer specific insecticides (such as cartap) or hopper specific insecticides (such as buprofezin) for use in rice may be employed. Alternatively insecticides or acaricides specific for particular insect species/stages may also be included in the compositions (for example acaricidal ovo-larvicides, such as clofentezine, flubenzimine, hexythiazox or tetradifon; acaricidal motilicides, such as dicofol or propargite; acaricides, such as bromopropylate or chlorobenzilate; or growth regulators, such as hydramethylnon, cyromazine, methoprene, chlorfluazuron or diflubenzuron).

Examples of fungicidal compounds which may be included in the composition of the invention are (E)-N-methyl-2-[2-(2,5-dimethylphenoxymethyl)phenyl]-2-methoxyiminoacetamide (SSF-129), 4-bromo-2-cyano-N,N-dimethyl-6-trifluoromethylbenzimidazole-1-sulphonamide, α-[N-(3-chloro-2,6-xylyl)-2-methoxyacetamido]-γ-butyrolactone, 4-chloro-2-cyano-N,N-dimethyl-5-p-tolylimidazole-1-sulfonamide (IKF-916, cyamidazosulfamid), 3-5-dichloro-N-(3-chloro-1-ethyl-1-methyl-2-oxopropyl)-4-methylbenzamide (RH-7281, zoxamide), N-allyl-4,5,-dimethyl-2-trimethylsilylthiophene-3-carboxamide (MON65500), N-(1-cyano-1,2-dimethylpropyl)-2-(2,4-dichlorophenoxy)propionamide (AC382042), N-(2-methoxy-5-pyridyl)-cyclopropane carboxamide, acibenzolar (CGA245704), alanycarb, aldimorph, anilazine, azaconazole, azoxystrobin, benalaxyl, benomyl, biloxazol, bitertanol, blasticidin S, bromuconazole, bupirimate, captafol, captan, carbendazim, carbendazim chlorhydrate, carboxin, carpropaamid, carvone, CGA41396, CGA41397, chinomethionate, chlorothalonil, chlorozolinate, clozylacon, copper containing compounds such as copper oxychloride, copper oxyquinolate, copper sulphate, copper tallate and Bordeaux mixture, cymoxanil, cyproconazole, cyprodinil, debacarb, di-2-pyridyl disulphide 1,1'-dioxide, dichlofluanid, diclomezine, dicloran, diethofencarb, difenoconazole, difenzoquat, diflumetorim, O,O-di-iso-propyl-5-benzyl thiophosphate, dimefluazole, dimetconazole, dimethomorph, dimethirimol, diniconazole, dinocap, dithianon, dodecyl dimethyl ammonium chloride, dodemorph, dodine, doguadine, edifenphos, epoxiconazole, ethirimol, ethyl(Z)-N-benzyl-N([methyl(methyl-thioethylideneaminooxycarbonyl)amino]thio)-β-alaninate, etridiazole, famoxadone, fenamidone (RPA407213), fenarimol, fenbuconazole, fenfuram, fenhexamid (KBR2738), fenpiclonil, fenpropidin, fenpropimorph, fentin acetate, fentin hydroxide, ferbam, ferimzone, fluazinam, fludioxonil, flumetover, fluoroimide, fluquinconazole, flusilazole, flutolanil, flutriafol, folpet, fuberidazole, furalaxyl, furametpyr, guazatine, hexaconazole, hydroxyisoxazole, hymexazole, imazalil, imibenconazole, iminoctadine, iminoctadine triacetate, ipconazole, iprobenfos, iprodione, iprovalicarb (SZX0722), isopropanyl butyl carbamate, isoprothiolane, kasugamycin, kresoxim-methyl, LY186054, LY211795, LY248908, mancozeb, maneb, mefenoxam, mepanipyrim, mepronil, metalaxyl, metconazole, metiram, metiram-zinc, metominostrobin, myclobutanil, neoasozin, nickel dimethyldithiocarbamate, nitrothal-isopropyl, nuarimol, ofurace, organomercury compounds, oxadixyl, oxasulfuron, oxolinic acid, oxpoconazole, oxycarboxin, pefurazoate, penconazole, pencycuron, phenazin oxide, phosetyl-Al, phosphorus acids, phthalide, picoxystrobin (ZA1963), polyoxin D, polyram, probenazole, prochloraz, procymidone, propamocarb, propiconazole, propineb, propionic acid, pyrazophos, pyrifenox, pyrimethanil, pyroquilon, pyroxyfur, pyrrolnitrin, quaternary ammonium compounds, quinomethionate, quinoxyfen, quintozene, sipconazole (F-155), sodium pentachlorophenate, spiroxamine, streptomycin, sulphur, tebuconazole, tecloftalam, tecnazene, tetraconazole, thiabendazole, thifluzamid, 2-(thiocyanomethylthio)benzothiazole, thiophanate-methyl, thiram, timibenconazole, tolclofos-methyl, tolylfluanid, triadimefon, triadimenol, triazbutil, triazoxide, tricyclazole, tridemorph, trifloxystrobin (CGA279202), triforine, triflumizole, triticonazole, validamycin A, vapam, vinclozolin, zineb and ziram.

The compounds of formula (I) may be mixed with soil, peat or other rooting media for the protection of plants against seed-borne, soil-borne or foliar fungal diseases.

Examples of suitable synergists for use in the compositions include piperonyl butoxide, sesamex, safroxan and dodecyl imidazole.

Suitable herbicides and plant-growth regulators for inclusion in the compositions will depend upon the intended target and the effect required.

An example of a rice selective herbicide which may be included is propanil. An example of a plant growth regulator for use in cotton is PIX™.

Some mixtures may comprise active ingredients which have significantly different physical, chemical or biological properties such that they do not easily lend themselves to the same conventional formulation type. In these circumstances other formulation types may be prepared. For example, where one active ingredient is a water insoluble solid and the other a water insoluble liquid, it may nevertheless be possible to disperse each active ingredient in the same continuous aqueous phase by dispersing the solid active ingredient as a suspension (using a preparation analogous to that of an SC) but dispersing the liquid active ingredient as an emulsion (using a preparation analogous to that of an EW). The resultant composition is a suspoemulsion (SE) formulation.

The invention is illustrated by the following Examples:

Mass spectra data were obtained for selected compounds of the following examples using LCMS: LC5: 254 nm—gradient 10% A to 100% B A=H2O+0.01% HCOOH B=CH3CN/CH3OH+0.01% HCOOH positive electrospray 150-1000 m/z.

EXAMPLE 1

This Example illustrates the preparation of 2-chloro-N-(4-chloro-2-{4-[(E)-3-(4-chloro-phenyl)-allyl]-piperazin-1-yl}-phenyl)-isonicotinamide

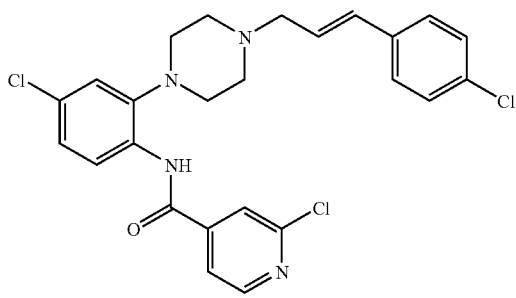

Step A: Triethylamine (4.2 ml) was added to a stirred solution of 2,4-dichloronitrobenzene (1.9 g) and 1-t-butoxycarbonyl-piperazine (2.2 g) in dimethylsulfoxide (18 ml) under $N_2$. The resulting solution was stirred at 70° C. for 48 hours then cooled to room temperature. Water was added and the mixture extracted three times with ethyl acetate; the combined organic layers were dried over sodium sulfate and concentrated in vacuo. The residue was subjected to silica gel chromatography (cyclohexane:ethyl acetate 8:2) to afford 4-(5-chloro-2-nitrophenyl)-piperazine-1-carboxylic acid tert-butyl ester (2.6 g) as a foam. $^1$H NMR (400 MHz, $CDCl_3$) 1.5 (s, 9H), 2.9 (br s, 4H), 3.5 (br s, 4H), 6.9 (d, J=10 Hz, 1H), 7.0 (s, 1H), 7.7 (d, J=10 Hz, 1H); MS (ES+) 242/244 (M+H$^+$—$CO_2$-isobutene), 286/288 (M+H$^+$-isobutene).

Step B: To a stirred suspension of the compound obtained in Step A (2.5 g) in ethanol (40 ml) and water (30 ml) at 60° C. was added sodium dithionite (7.6 g). The resulting mixture was stirred at 60° C. for 1 hour then ethanol was removed in vacuo. The suspension was extracted three times with ethyl acetate, the combined organic layers were dried over sodium sulfate and concentrated in vacuo. The residue was subjected to silica gel chromatography (cyclohexane:ethyl acetate 1:1) to afford 4-(2-Amino-5-chlorophenyl)-piperazine-1-carboxylic acid tert-butyl ester (1.0 g) as white crystals. M.p. 125-127° C.; $^1$H NMR (400 MHz, $CDCl_3$) 1.5 (s, 9H), 2.8 (m, 4H), 3.5 (m, 4H), 3.9 (s, 2H), 6.6 (d, J=10 Hz, 1H), 6.8 (d, J=10 Hz, 1H), 6.9 (s, 1H); MS (ES+) 212/214 (M+H$^+$—$CO_2$-isobutene), 256/258 (M+H$^+$-isobutene), 312/314 (M+H$^+$).

Step C: triethylamine (2 ml) was added to a stirred solution of the compound obtained in Step B (1.0 g) in dichloromethane (20 ml); the solution was cooled to 0° C. and 2-chloro-isonicotinoyl chloride (1.2 g) was added. The resulting mixture was stirred at room temperature for 12 hours, poured into water, extracted two times with dichloromethane, the combined organic layers were dried over sodium sulfate and concentrated in vacuo. The residue was subjected to silica gel chromatography (cyclohexane:ethyl acetate 7:2) to afford 4-{5-Chloro-2-[(2-chloro-pyridine-4-carbonyl)-amino]-phenyl}-piperazine-1-carboxylic acid tert-butyl ester, which was recrystallised (845 mg) from hexane/ethyl acetate to give white crystals. M.p. 185-189° C.; $^1$H NMR (400 MHz, $CDCl_3$) 1.5 (s, 9H), 2.9 (m, 4H), 3.7 (m, 4H), 7.2 (d, J=1.5 Hz, 1H), 7.2 (dd, J=1.5, 10 Hz, 1H), 7.6 (d, J=5.5 Hz, 1H), 7.8 (s, 1H), 8.5 (d, J=10 Hz, 1H), 8.63 (d, J=5.5 Hz, 1H), 9.4 (s, 1H, NH); MS (ES+) 351/353 (M+H$^+$—$CO_2$-isobutene), 395/397 (M+H$^+$-isobutene), 451/453 (M+H$^+$).

Step D: A solution of the compound obtained in Step C (200 mg) in dichloromethane (10 ml) was treated with trifluoroacetic acid (0.3 ml) for 48 hours at room temperature. The reaction mixture was basified with saturated aqueous sodium bicarbonate, extracted two times with dichloromethane, the organic layer was dried over sodium sulfate and concentrated in vacuo. The residue was dissolved in acetonitrile (20 ml), diisopropylethylamine (0.16 ml) and 4-chlorocinnamyl chloride (96 mg) were added. The solution was stirred 50 hours at room temperature, the solvent was removed in vacuo and the residue was subjected to silica gel chromatography (cyclohexane:ethyl acetate 7:2) to afford the title product (162 mg) as a yellow solid. M.p. 129-132° C.; $^1$H NMR (400 MHz, $CDCl_3$) 2.7 (m, 4H), 2.9 (m, 4H), 3.2 (d, J=9 Hz, 2H), 6.2 (dt, J=18, 9 Hz, 1H), 6.5 (d, J=18 Hz, 1H), 7.1-7.3 (m, 6H), 7.6 (d, J=5.5 Hz, 1H), 7.70 (s, 1H), 8.4 (d, J=10 Hz, 1H), 8.5 (d, J=5.5 Hz, 1H), 9.4 (s, 1H, NH); Retention Time HPLC 2.46 min; MS (ES+) 501/503/505 (M+H$^+$).

The following compounds were prepared according to procedures analogous to those described in Example 1:

| Compound Name | Structure | M.p (° C.) | MH$^+$ | Retention Time (min) |
|---|---|---|---|---|
| 2-chloro-N-(2-{4-[(E)-3-(4-chloro-phenyl)-allyl]-piperazin-1-yl}-phenyl)-isonicotinamide | 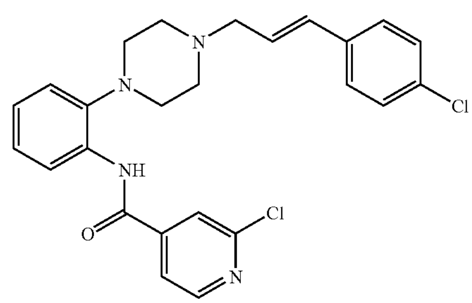 | | 467/469 | 2.26 |

-continued

| Compound Name | Structure | M.p (° C.) | MH+ | Retention Time (min) |
|---|---|---|---|---|
| 2-chloro-N-(2-{4-[(E)-3-(4-trifluoromethyl-phenyl)-allyl]-piperazin-1-yl}-phenyl)-isonicotinamide | 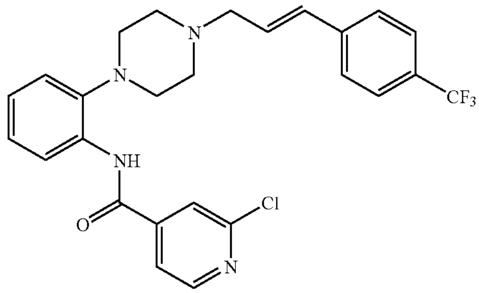 | | 501 | 2.32 |
| 2-chloro-N-(2-{4-[(E)-3-(4-trifluoromethoxy-phenyl)-allyl]-piperazin-1-yl}-phenyl)-isonicotinamide | 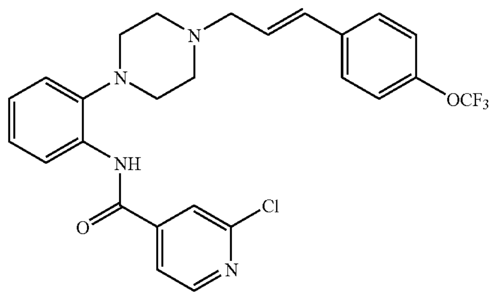 | | 517 | 2.46 |
| 2-chloro-N-(4-fluoro-2-{4-[(E)-3-(4-chloro-phenyl)-allyl]-piperazin-1-yl}-phenyl)-isonicotinamide | 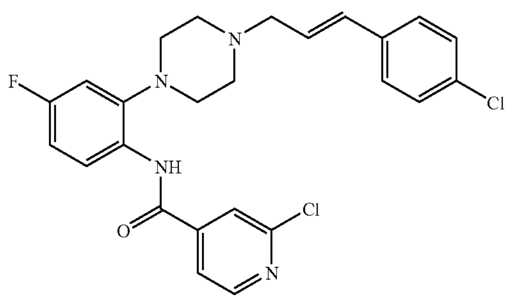 | 145-147 | 485/487 | 2.29 |
| 2-chloro-N-(4-fluoro-2-{4-[(E)-3-(4-trifluoromethyl-phenyl)-allyl]-piperazin-1-yl}-phenyl)-isonicotinamide | 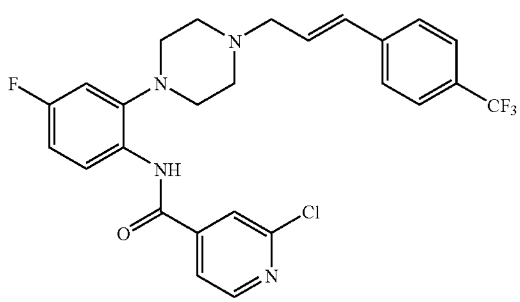 | 98-100 | 519 | 1.91 |
| 2-chloro-N-(4-fluoro-2-{4-[(E)-3-(4-trifluoromethoxy-phenyl)-allyl]-piperazin-1-yl}-phenyl)-isonicotinamide | 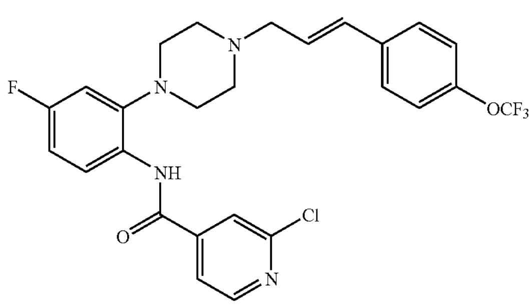 | 85-89 | 535/537 | 2.44 |

-continued

| Compound Name | Structure | M.p (° C.) | MH+ | Retention Time (min) |
|---|---|---|---|---|
| 2-chloro-N-(5-fluoro-2-{4-[(E)-3-(4-chloro-phenyl)-allyl]-piperazin-1-yl}-phenyl)-isonicotinamide | 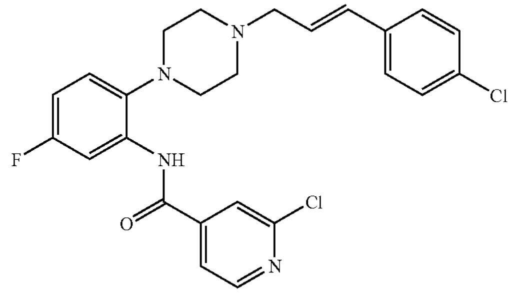 | 80-83 | 485/487 | 2.28 |
| 2-chloro-N-(5-fluoro-2-{4-[(E)-3-(4-trifluoromethyl-phenyl)-allyl]-piperazin-1-yl}-phenyl)-isonicotinamide | 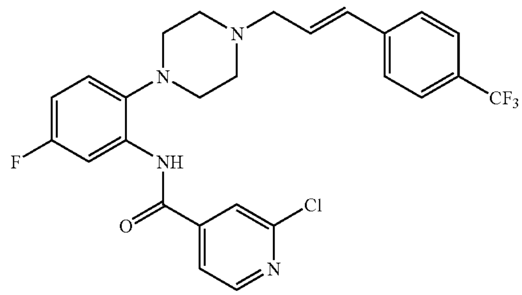 | 105-109 | 519 | 2.51 |
| 2-chloro-N-(5-fluoro-2-{4-[(E)-3-(4-trifluoromethoxy-phenyl)-allyl]-piperazin-1-yl)-phenyl)-isonicotinamide | 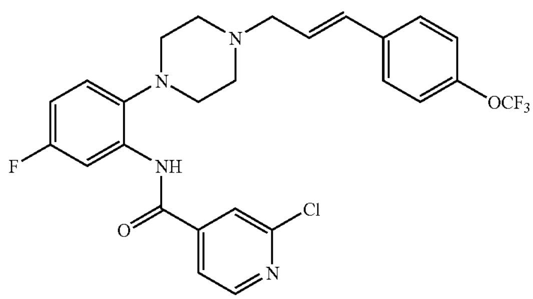 | 110-114 | 535 | 2.48 |
| 2-chloro-N-(4-chloro-2-{4-[(E)-3-(4-trifluoromethyl-phenyl)-allyl]-piperazin-1-yl}-phenyl)-isonicotinamide | 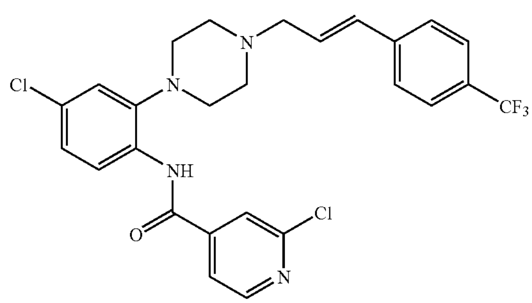 | 129-131 | 131 | 2.56 |
| 2-chloro-N-(4-chloro-2-{4-[(E)-3-(4-trifluoromethoxy-phenyl)-allyl]-piperazin-1-yl}-phenyl)-isonicotinamide | 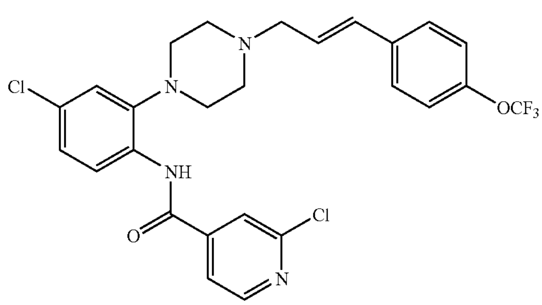 | 92-95 | 551/553 | 2.63 |

-continued

| Compound Name | Structure | M.p (° C.) | MH+ | Retention Time (min) |
|---|---|---|---|---|
| 2-chloro-N-(3,4-dichloro-2-{4-[(E)-3-(4-chloro-phenyl)-allyl]-piperazin-1-yl}-phenyl)-isonicotinamide | 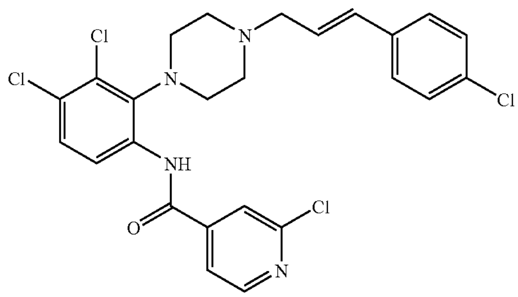 | 154-156 | 537/539 | 2.38 |
| 2,6-dichloro-N-(3,4-dichloro-2-{4-[(E)-3-(4-chloro-phenyl)-allyl]-piperazin-1-yl}-phenyl)-isonicotinamide | 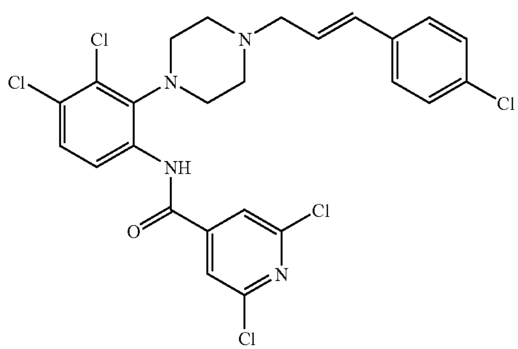 | 178-181 | 571/573 | 2.67 |
| N-(4-chloro-2-{4-[(E)-3-(4-chloro-phenyl)-allyl]-piperazin-1-yl}-phenyl)-benzamide | 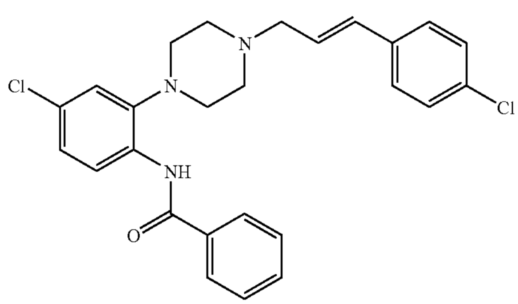 | 79-81 | 466/468 | 2.49 |
| N-(4-chloro-2-{4-[(E)-3-(4-chloro-phenyl)-allyl]-piperazin-1-yl}-phenyl)-isonicotinamide | 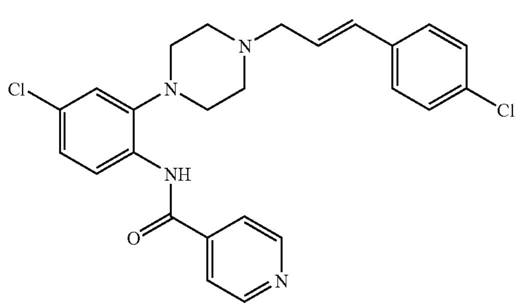 | 152-154 | 467-469 | 2.11 |

-continued

| Compound Name | Structure | M.p (° C.) | MH+ | Retention Time (min) |
|---|---|---|---|---|
| 2,6-dichloro-N-(4-chloro-2-{4-[(E)-3-(4-chloro-phenyl)-allyl]-piperazin-1-yl}-phenyl)-isonicotinamide | 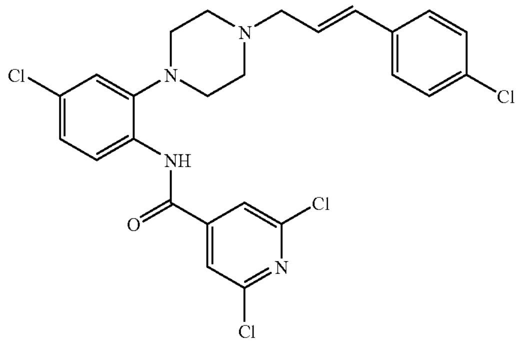 | 121-123 | 537/539 | 2.77 |
| 6-chloro-N-(4-chloro-2-{4-[(E)-3-(4-chloro-phenyl)-allyl]-piperazin-1-yl}-phenyl)-nicotinamide | 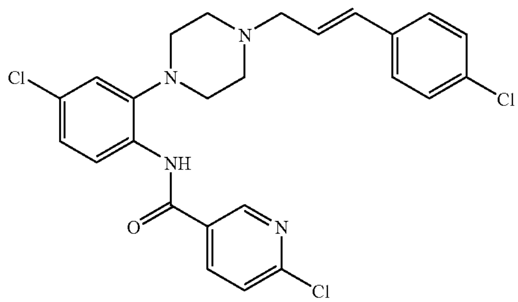 | 120-123 | 467/469 | 2.10 |
| N-(4-chloro-2-{4-[(E)-3-(4-chloro-phenyl)-allyl]-piperazin-1-yl}-phenyl)-4-trifluoromethoxy-benzamide | 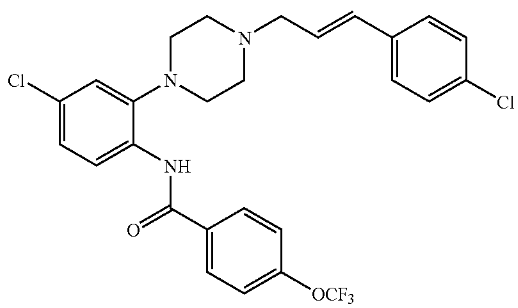 | 104-107 | 550/552 | 3.22 |
| N-(4-chloro-2-{4-[(E)-3-(4-chloro-phenyl)-allyl]-piperazin-1-yl}-phenyl)-4-chloro-benzamide | 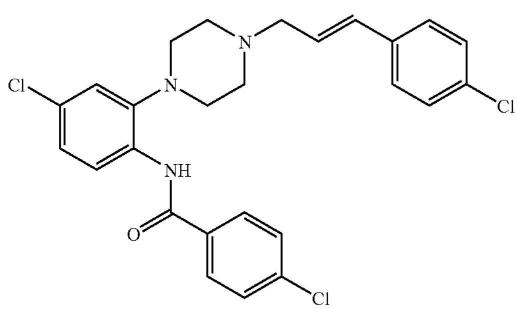 | 62-64 | 502/504 | 2.85 |
| N-(4-chloro-2-{4-[(E)-3-(4-chloro-phenyl)-allyl]-piperazin-1-yl}-phenyl)-acetamide | 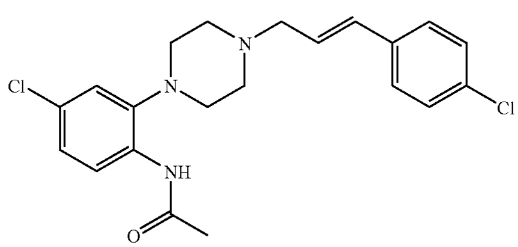 | 145-148 | 404/406 | 1.95 |

-continued

| Compound Name | Structure | M.p (° C.) | MH+ | Retention Time (min) |
|---|---|---|---|---|
| cyclopropanecarboxylic acid (4-chloro-2-{4-[(E)-3-(4-chloro-phenyl)-allyl]-piperazin-1-yl}-phenyl)-amide | 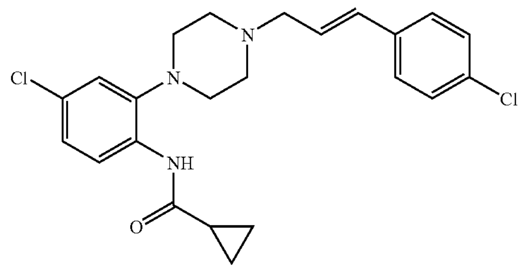 | 87-89 | 430/432 | 2.17 |
| (4-chloro-2-{4-[(E)-3-(4-chloro-phenyl)-allyl]-piperazin-1-yl}-phenyl)-carbamic acid methyl ester | 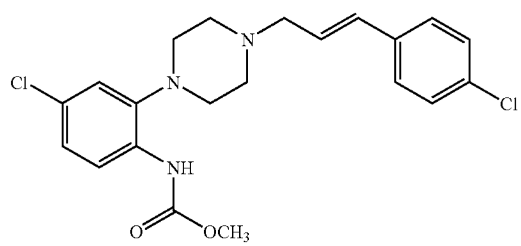 | 73-76 | 420/422 | 2.17 |
| 2-fluoro-N-(4-chloro-2-{4-[(E)-3-(4-chloro-phenyl)-allyl]-piperazin-1-yl}-phenyl)-isonicotinamide | 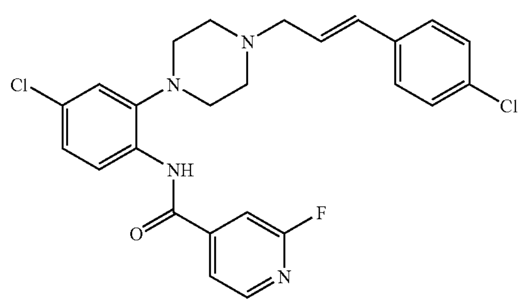 | 162-165 | 485/487 | 2.31 |
| 2-(3-chloro-pyridin-2-yl)-5-trifluoromethyl-2H-pyrazole-3-carboxylic acid (4-chloro-2-{4-[(E)-3-(4-chloro-phenyl)-allyl]-piperazin-1-yl}-phenyl)-amide | 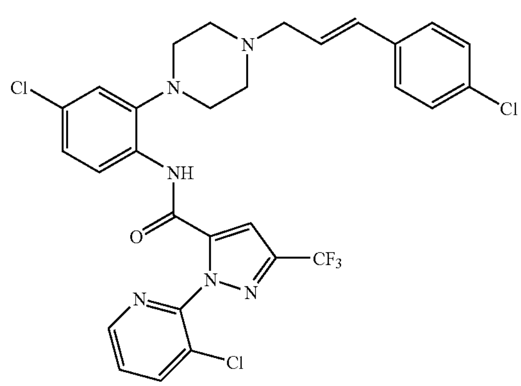 | 97-100 | 637/639 | 2.65 |

| Compound Name | Structure | M.p (° C.) | MH+ | Retention Time (min) |
|---|---|---|---|---|
| 2-chloro-N-(4-chloro-5-trifluoromethyl-2-{4-[(E)-3-(4-chloro-phenyl)-allyl]-piperazin-1-yl}-phenyl)-isonicotinamide | 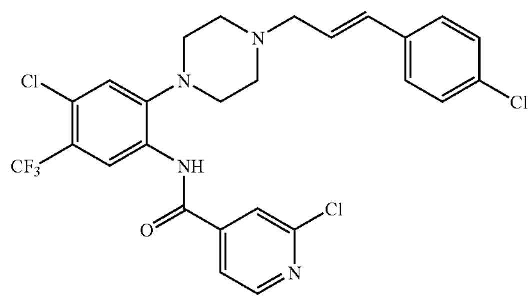 | 135-136 | 569/571 | 2.92 |
| 2-Chloro-N-{4-chloro-2-[4-(4-chloro-benzyl)-piperazin-1-yl]-phenyl}-isonicotinamide | | 116-118 | 475/477 | 2.50 |
| N-(4-Chloro-2-{4-[(E)-3-(4-chloro-phenyl)-allyl]-piperazin-1-yl}-phenyl)-methanesulfonamide | 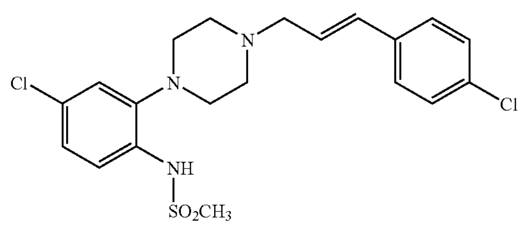 | 81-83 | 440-442 | 2.01 |

EXAMPLE 2

This Example illustrates the preparation of 2-chloro-N-(2-{4-[(E)-3-(4-chloro-phenyl)-allyl]-piperazin-1-yl}-phenyl)-N-methyl-isonicotinamide.

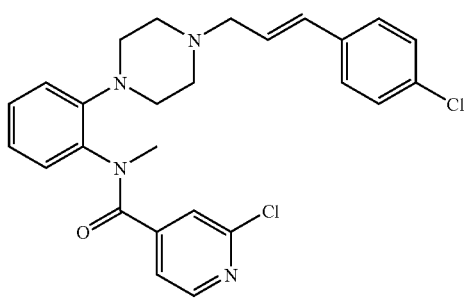

4-{2-[(2-chloro-pyridine-4-carbonyl)-amino]-phenyl}-piperazine-1-carboxylic acid tert-butyl ester (100 mg, prepared as described in Example 1, Steps A-C) was added to a suspension of sodium hydride (50% in oil, 24 mg) in tetrahydrofuran at 0° C. and the resulting mixture was stirred at 0° C. for 1 hour at which time iodomethane (0.03 ml) was added. The reaction mixture was stirred at room temperature for 3 hours, diluted with ethyl acetate, washed three times with water, dried over sodium sulfate and concentrated in vacuo. The residue was subjected to silica gel chromatography (cyclohexane:ethyl acetate 7:3) to afford 4-{2-[(2-Chloro-pyridine-4-carbonyl)-methyl-amino]-phenyl}-piperazine-1-carboxylic acid tert-butyl ester as white crystals. M.p. 59-61° C.; $^1$H NMR (400 MHz, CDCl$_3$) 1.5 (s, 9H), 2.2 (m, 2H), 2.8 (m, 2H), 3.4 (m, 2H), 3.4 (s, 3H), 3.5 (m, 2H), 6.7 (m, 1H), 6.9 (m, 1H), 7.0-7.3 (m, 4H), 8.1 (m, 1H); MS (ES+) 331 (M+H$^+$—CO$_2$-isobutene), 375 (M+H$^+$-isobutene), 431 (M+H$^+$). This compound was treated according to Example 1 Step D to afford the title product as yellow crystals. M.p. 117-120° C.; $^1$H NMR (400 MHz, CDCl$_3$) 2.4 (m, 2H), 2.5 (m, 2H), 2.6 (m, 2H), 2.9 (m, 2H), 3.2 (m, 2H), 3.5 (s, 3H), 3.5 (m, 2H), 6.2 (dt, J=18, 9 Hz, 1H), 6.5 (d, J=18 Hz, 1H), 6.8 (d, J=9 Hz, 1H), 6.9

(d, J=5 Hz, 1H), 7.0-7.3 (m, 6H), 8.1 (d, J=5 Hz, 1H); retention Time HPLC 2.17 min; MS (ES+) 481/483 (M+H⁺).

The following compounds were prepared according to procedures analogous to those described in Example 2:

| Compound Name | Structure | M.p (°C.) | MH⁺ | Retention Time (min) |
|---|---|---|---|---|
| 2-chloro-N-(5-fluoro-2-{4-[(E)-3-(4-chloro-phenyl)-allyl]-piperazin-1-yl}-phenyl)-N-methyl-isonicotinamide | 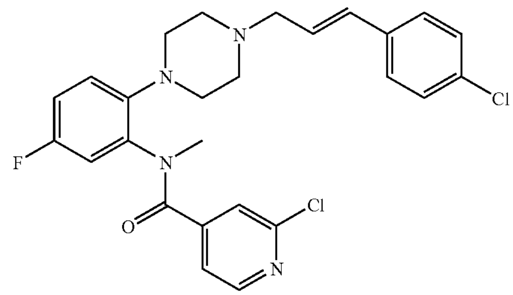 | 60-64 | 499/501 | 2.12 |
| 2-chloro-N-(4-fluoro-2-{4-[(E)-3-(4-chloro-phenyl)-allyl]-piperazin-1-yl}-phenyl)-N-methyl-isonicotinamide | 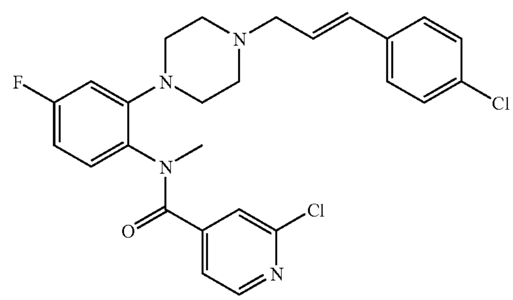 | 110-117 | 499/501 | 2.09 |
| 2-chloro-N-(4-chloro-2-{4-[(E)-3-(4-chloro-phenyl)-allyl]-piperazin-1-yl}-phenyl)-N-methyl-isonicotinamide | 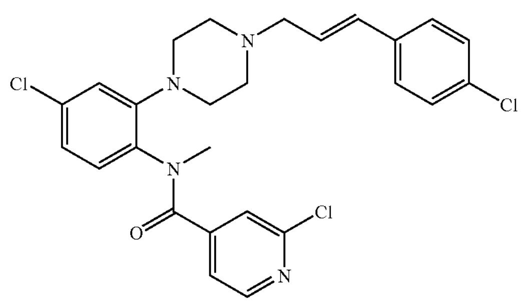 | 130-133 | 517-519 | 2.28 |
| 2-chloro-N-(3,4-dichloro-2-{4-[(E)-3-(4-chloro-phenyl)-allyl]-piperazin-1-yl}-phenyl)-N-methyl-isonicotinamide | 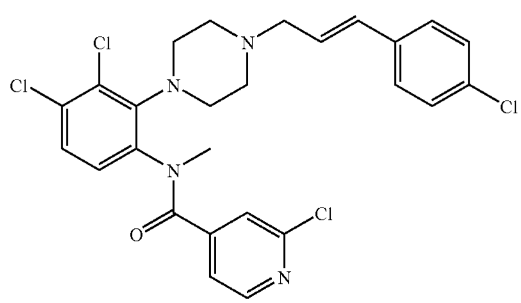 | 112-115 | 551/553 | 2.42 |

EXAMPLE 3

This Example illustrates the preparation of 2-Chloro-N-[4-chloro-2-(4-methyl-piperazin-1-yl)-phenyl]-isonicotinamide.

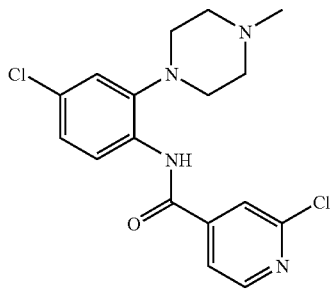

Step A: A solution of 4-{5-chloro-2-[(2-chloro-pyridine-4-carbonyl)-amino]-phenyl}-piperazine-1-carboxylic acid tert-butyl ester (6.7 g, Example 1, Step C) in dichloromethane (20 ml) was treated with trifluoroacetic acid (10 ml) for 20 hours at room temperature. Concentration of the solution under reduced pressure afforded 2-chloro-N-[4-chloro-2-(piperazin-1-yl)-phenyl]-isonicotinamide trifluoroacetate (6.9 g) as a brown solid. MS (ES+) 351/353 (M+H[+]).

Step B: The product obtained in Step A (300 mg), formic acid (16 ml) and 37% aqueous formaldehyde (0.47 ml) were refluxed for 2 hours. The reaction mixture was diluted with water, made basic with saturated aqueous sodium bicarbonate and extracted with ethyl acetate. The organic layer was dried over sodium sulfate and concentrated in vacuo. The residue was subjected to silica gel chromatography (ethyl acetate:methanol 8:2) to afford the title product. M.p. 118-120° C.; $^1$H NMR (400 MHz, CDCl$_3$) 2.4 (s, 3H), 2.7 (m, 2H), 3.0 (m, 4H), 7.2 (m, 2H), 7.6 (d, J=5.0 Hz, 1H), 7.7 (s, 1H), 8.4 (d, J=9.0 Hz, 1H), 8.5 (d, J=5.0 Hz, 1H), 9.4 (br s, 1H); MS (ES+) 365/367 (M+H[+]).

EXAMPLE 4

This Example illustrates the preparation of 1-(2-{4-[(E)-3-(4-chloro-phenyl)-allyl]-piperazin-1-yl}-4-fluoro-phenyl)-3-(3-methoxy-propyl)-urea.

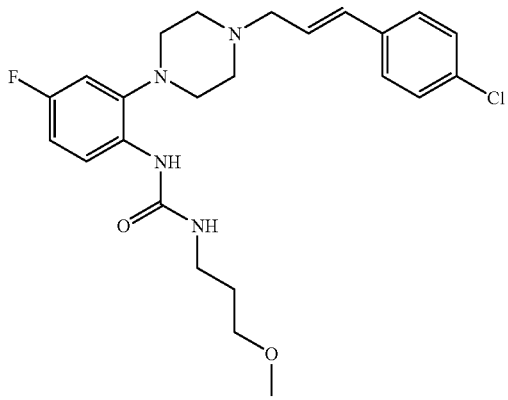

Step A: A solution of 4-(5-fluoro-2-nitrophenyl)-piperazine-1-carboxylic acid tert-butyl ester (10 g, prepared from 2,4-difluoronitrobenzene as described in Example 1, Step A) in dichloromethane (80 ml) was treated with trifluoroacetic acid (23 ml) for 24 hours at room temperature. The reaction mixture was concentrated in vacuo. The residue was dissolved in acetonitrile (100 ml), diisopropylethylamine (27 ml) and 4-chloro-cinnamyl chloride (6.8 g) were added. The solution was stirred for 17 hours at room temperature, the solvent was removed in vacuo and the residue was subjected to silica gel chromatography (cyclohexane:ethyl acetate 1:1) to afford 1-[(E)-3-(4-chloro-phenyl)-allyl]-4-(5-fluoro-2-nitro-phenyl)-piperazine (10.5 g); $^1$H NMR (400 MHz, CDCl$_3$) 2.7 (t, J=8 Hz, 4H), 3.1 (t, J=8 Hz, 4H), 3.2 (d, J=9 Hz, 2H), 6.2 (dt, J=18, 9 Hz, 1H), 6.5 (d, J=18 Hz, 1H), 6.6 (dt, J=1.0, 7.0 Hz, 1H), 6.7 (dd, J=1.0, 10 Hz, 1H), 7.2-7.3 (m, 4H), 7.8 (d, J=7.0, 10.0 Hz, 1H); MS (ES+) 151/153, 376/378 (M+H[+]).

Step B: To a stirred suspension of the compound obtained in Step A (8.0 g) in ethanol (66 ml) and water (80 ml) at 60° C. was added sodium dithionite (11 g). The resulting mixture was stirred at 60° C. for 1 hour then ethanol was removed in vacuo. The suspension was extracted three times with ethyl acetate, the combined organic layers were dried over sodium sulfate and concentrated in vacuo. The residue was filtered on silica gel (eluent ethyl acetate) to afford 1-[(E)-3-(4-chloro-phenyl)-allyl]-4-(5-fluoro-2-amino-phenyl)-piperazine (4.1 g). $^1$H NMR (400 MHz, CDCl$_3$) 2.6 (m, 4H), 2.9 (m, 4H), 3.2 (d, J=9 Hz, 2H), 3.7 (m, 2H), 6.2 (dt, J=18, 9 Hz, 1H), 6.5 (d, J=18 Hz, 1H), 6.6 (m, 2H), 6.7 (d, J=10 Hz, 1H), 7.2-7.3 (m, 4H); MS (ES+) 151/153, 346/348 (M+H[+]).

Step C: To a stirred solution of di-tert-butyl carbonate (266 mg) in dichloromethane (4 ml) under nitrogen was added 4-dimethylaminopyridine (106 mg) in dichloromethane (4 ml) followed by the product obtained in Step B (300 mg). The solution was stirred at room temperature until gas evolution ceased. 3-Methoxypropylamine (155 mg) dissolved in dichloromethane (4 ml) was then added dropwise and the resulting solution stirred at room temperature for 1 hour. The solvent was removed under reduced pressure and the residue purified by silica gel chromatography (cyclohexane:ethyl acetate 1:9) to afford the title product (210 mg). M.p. 86-90° C.; $^1$H NMR (400 MHz, CDCl$_3$) 1.8 (quint, J=7 Hz, 2H), 2.6 (m, 4H), 2.9 (m, 4H), 3.2 (d, J=9 Hz, 2H), 3.2 (s, 3H), 3.3 (q, J=7 Hz, 2H), 3.4 (t, J=7 Hz, 2H), 5.3 (m, 1H), 6.2 (dt, J=18, 9 Hz, 1H), 6.5 (d, J=18 Hz, 1H), 6.8 (m, 2H), 6.9 (s, 1H), 7.2-7.3 (m, 6H), 7.7 (m, 1H); Retention Time HPLC 1.93; MS (ES+) 372/374, 461/463 (M+H[+]).

The following compounds were prepared according to procedures analogous to those described in Example 4:

| Compound Name | Structure | M.p (° C.) | MH+ | Retention Time (min) |
|---|---|---|---|---|
| 1-(4-Chloro-2-{4-[(E)-3-(4-chloro-phenyl)-allyl]-piperazin-1-yl}-phenyl)-3-(2-methoxy-ethyl)-urea | 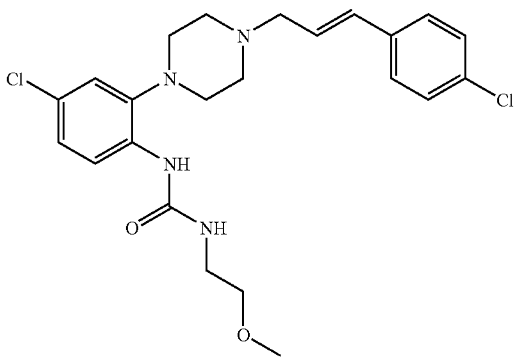 | 178 | 463/465 | 1.97 |
| 1-(2-{4-[(E)-3-(4-chloro-phenyl)-allyl]-piperazin-1-yl}-4-fluoro-phenyl)-3-(2-chloro-thiazol-5-ylmethyl)-urea | 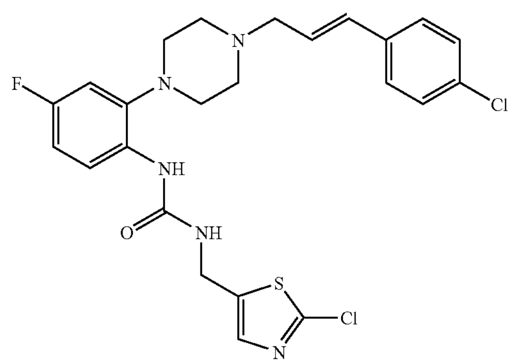 | 94-98 | 520/522 | 2.12 |
| 1-(2-{4-[(E)-3-(4-chloro-phenyl)-allyl]-piperazin-1-yl}-4-fluoro-phenyl)-3-(2-[1,3]dioxolan-2-yl-ethyl)-urea | 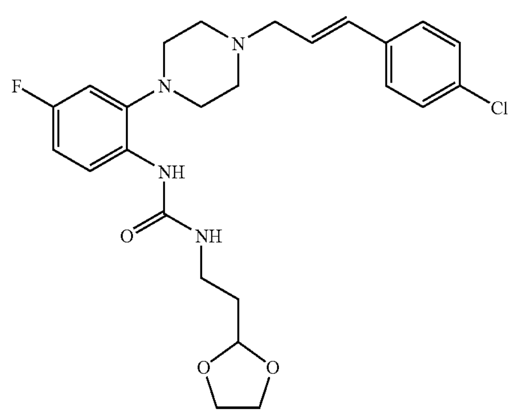 | 76-80 | 489 | 2.02 |
| 1-(2-{4-[(E)-3-(4-chloro-phenyl)-allyl]-piperazin-1-yl}-4-fluoro-phenyl)-3-isopropyl-urea | 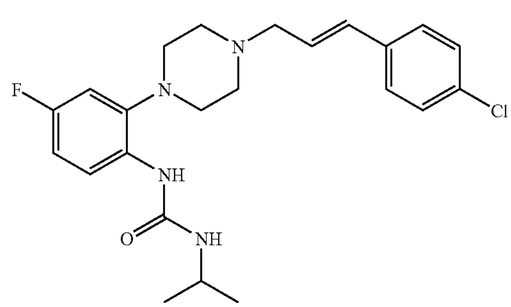 | 162-166 | 431 | 2.08 |

EXAMPLE 5

This Example illustrates the preparation of 1-(2-{4-[(E)-3-(4-Chloro-phenyl)-allyl]-piperazin-1-yl}-4-fluoro-phenyl)-3-(2-chloro-thiazol-5-ylmethyl)-imidazolidin-2-one.

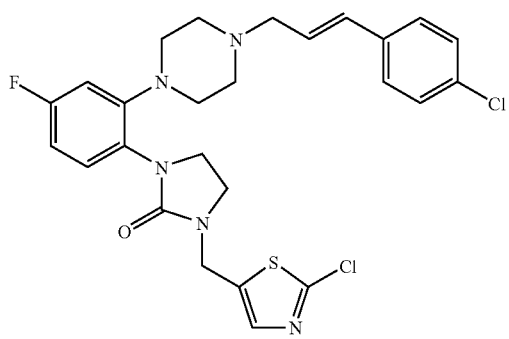

Step A: To a solution of 1-[(E)-3-(4-chloro-phenyl)-allyl]-4-(5-fluoro-2-amino-phenyl)-piperazine (1.0 g, Example 3, Step B) in tetrahydrofuran (10 ml) at 0° C. was added 2-chloroethylisocyanate (327 mg) and the resulting solution was stirred under nitrogen at room temperature for 18 hours. The residue was dissolved in a minimum volume of tetrahydrofuran, then added to a suspension of sodium hydride (146 mg, 50% in oil) in tetrahydrofuran (10 ml). The reaction mixture was stirred at room temperature for 3 hours, concentrated under reduced pressure, then triturated with diethyl ether to afford 1-(2-{4-[(E)-3-(4-chloro-phenyl)-allyl]-piperazin-1-yl}-4-fluoro-phenyl)-imidazolidin-2-one (677 mg) as white crystals. M.p. 170-172° C.; $^1$H NMR (400 MHz, CDCl$_3$) 2.7 (m, 4H), 3.11 (m, 4H), 3.26 (d, J=6.8 Hz, 2H), 3.63 (t, J=5.7 Hz, 2H), 3.99 (t, J=5.7 Hz, 2H), 5.12 (br s, 1H), 6.32 (dt, J=15.6, 6.8 Hz, 1H), 6.57 (d, J=15.6 Hz, 1H), 6.82 (m, 2H), 7.3-7.4 (m, 4H); MS (ES+) 415/417 (M+H$^+$).

Step B: The product obtained in Step A (250 mg) dissolved in dimethylacetamide (4 ml) was added to a suspension of sodium hydride (50% in oil, 29 mg) in dimethylacetamide (4 ml) at 0° C. and the resulting mixture was stirred at 0° C. for 30 min at which time C-(2-chloro-thiazol-5-yl)-methylamine (102 mg) dissolved in dimethylacetamide (4 ml) was added. The reaction mixture was stirred at room temperature for 2 hours, quenched by addition of water, extracted with ethyl acetate (three times), dried over sodium sulfate and concentrated in vacuo. The residue was subjected to silica gel chromatography (cyclohexane:ethyl acetate 1:9) to afford the title product as a yellow solid. M.p. 72-77° C.; $^1$H NMR (400 MHz, CDCl$_3$) 2.7 (m, 4H), 3.0 (m, 4H), 3.2 (d, J=7 Hz, 2H), 3.35 (t, J=6 Hz, 2H), 3.8 (t, J=6 Hz, 2H), 4.5 (s, 2H), 6.3 (dt, J=16, 7 Hz, 1H), 6.5 (d, J=16 Hz, 1H), 6.8 (m, 2H), 7.2-7.3 (m, 4H), 7.4 (s, 1H); MS (ES+) 546/548 (M+H$^+$).

EXAMPLE 6

This Example illustrates the preparation of 2-chloro-N-(5-chloro-2-{4-[(E)-3-(4-trifluoromethyl-phenyl)-allyl]-piperazin-1-yl}-pyridin-3-yl)-isonicotinamide.

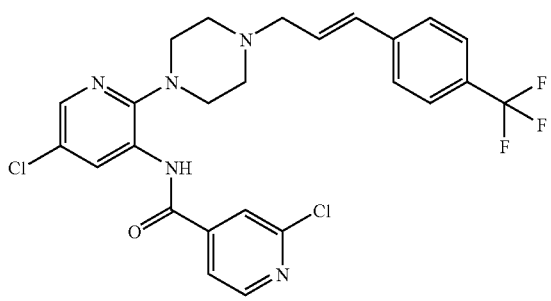

Step A: piperazine (1.38 g) was added to a stirred solution of 2,6-dichloro-3-nitropyridine (3.0 g, prepared according to *J. Heterocyclic Chem.* 1994, 31, 73) and diisopropylethylamine (3.0 ml) in dichloromethane (100 ml) at 0° C. under N$_2$. The resulting solution was stirred at room temperature for 2 hours then poured into saturated aqueous sodium bicarbonate, extracted with dichloromethane, dried over sodium sulfate and concentrated in vacuo. The residue was subjected to silica gel chromatography (ethyl acetate: methanol 8:2) to afford 1-(6-Chloro-3-nitro-pyridin-2-yl)-piperazine (2.99 g) as a red solid. M.p. 50-53° C.; MS (ES+) 243/245 (M+H$^+$).

Step B: The product obtained in Step A (800 mg) was dissolved in acetonitrile (320 ml), diisopropylethylamine (1.2 ml) and 4-trifluoromethylcinnamyl chloride (728 mg) were added. The solution was stirred at room temperature for 24 hours, the solvent was removed in vacuo and the residue was subjected to silica gel chromatography (cyclohexane: ethyl acetate 7:3) to afford 1-(5-Chloro-3-nitro-pyridin-2-yl)-4-[(E)-3-(4-trifluoromethyl-phenyl)-allyl]-piperazine (0.79 g) as a yellow foam. M.p. 129-132° C.; $^1$H NMR (400 MHz, CDCl$_3$) 2.7 (m, 4H), 3.3 (d, J=9 Hz, 1H), 3.5 (m, 4H), 6.3 (dt, J=18, 9 Hz, 1H), 6.5 (d, J=18 Hz, 1H), 7.4 (m, 4H), 8.2 (d, J=2 Hz, 1H), 8.3 (d, J=2 Hz, 1H); MS (ES+) 427/429 (M+H$^+$).

Step C: The product obtained in Step B (435 mg) was reduced and acylated as described in Example 1 Step B and C to afford after silica gel chromatography (cyclohexane:ethyl acetate 7:3) the title product (185 mg). M.p. 156-159° C.; $^1$H NMR (400 MHz, CDCl$_3$) 2.7 (m, 4H), 3.1 (m, 4H), 3.2 (d, J=9 Hz, 2H), 6.3 (dt, J=18, 9 Hz, 1H), 6.5 (d, J=18 Hz, 1H), 7.4 (d, J=9 Hz, 2H), 7.45 (d, J=9 Hz, 2H), 7.5 (d, J=5 Hz, 1H), 7.6 (s, 1H), 8.0 (d, J=1.5 Hz, 1H), 8.55 (d, J=5 Hz, 1H), 8.65 (d, J=1.5 Hz, 1H), 8.8 (s, 1H, NH); HPLC Retention Time 2.12 min; MS (ES+) 536/538 (M+H$^+$).

The following compounds were prepared according to procedures analogous to those described in Example 6:

| Compound Name | Structure | M.p (° C.) | MH+ | Retention Time (min) |
|---|---|---|---|---|
| 2-chloro-N-(2-{4-[(E)-3-(4-chloro-phenyl)-allyl]-piperazin-1-yl}-pyridin-3-yl)-isonicotinamide | 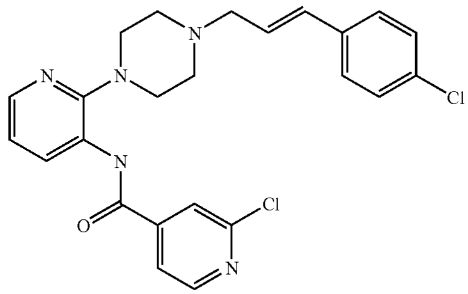 | 106-109 | 468/470 | 2.05 |
| 2-chloro-N-(2-{4-[(E)-3-(4-trifluoromethoxy-phenyl)-allyl]-piperazin-1-yl}-pyridin-3-yl)-isonicotinamide | 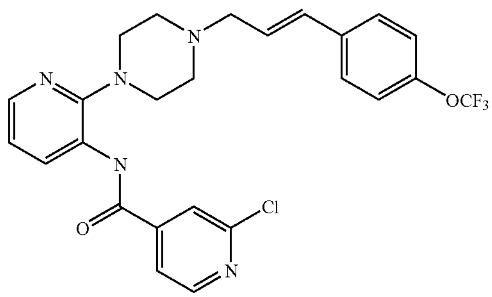 | | 518/520 | 2.19 |
| 2-chloro-N-(6-chloro-2-{4-[(E)-3-(4-chloro-phenyl)-allyl]-piperazin-1-yl}-pyridin-3-yl)-isonicotinamide | 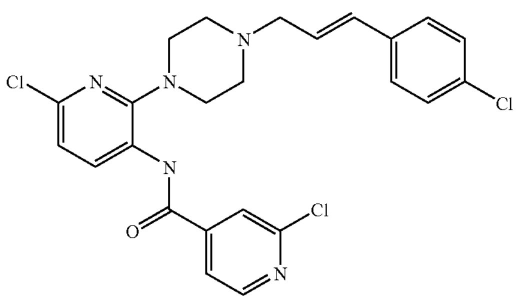 | 70-73 | 502/504 | 2.16 |
| 2-chloro-N-(5-chloro-2-{4-[(E)-3-(4-chloro-phenyl)-allyl]-piperazin-1-yl}-pyridin-3-yl)-isonicotinamide | 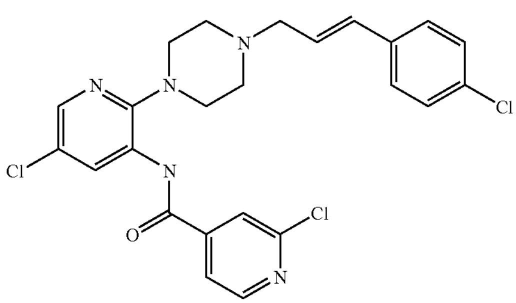 | 127-129 | 502/504 | 2.29 |
| 2-chloro-N-(5-chloro-2-{4-[(E)-3-(4-trifluoromethoxy-phenyl)-allyl]-piperazin-1-yl}-pyridin-3-yl)-isonicotinamide | 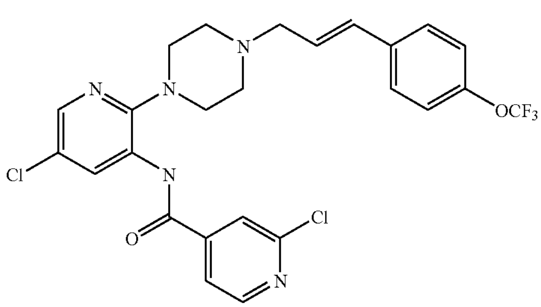 | 115-117 | 552/554 | 2.40 |

-continued

| Compound Name | Structure | M.p (° C.) | MH+ | Retention Time (min) |
|---|---|---|---|---|
| 2-chloro-N-(6-methyl-2-{4-[(E)-3-(4-chloro-phenyl)-allyl]-piperazin-1-yl}-pyridin-3-yl)-isonicotinamide | 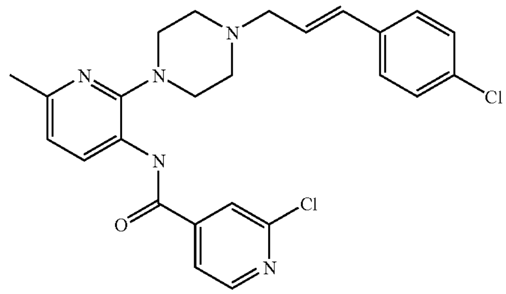 | 67-70 | 482/484 | 2.44 |
| 2-Chloro-N-(4-chloro-6-{4-[(E)-3-(4-chloro-phenyl)-allyl]-piperazin-1-yl}-pyrimidin-5-yl)-isonicotinamide | 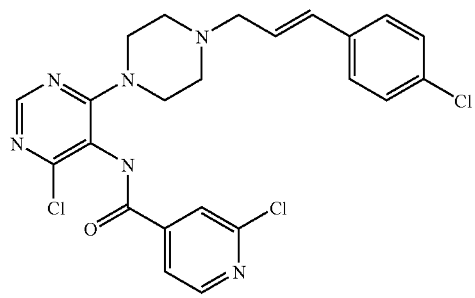 | 84-87 | 503/505 | 2.48 |
| 2-Chloro-N-(4-{4-[(E)-3-(4-chloro-phenyl)-allyl]-piperazin-1-yl}-pyridin-3-yl)-isonicotinamide | 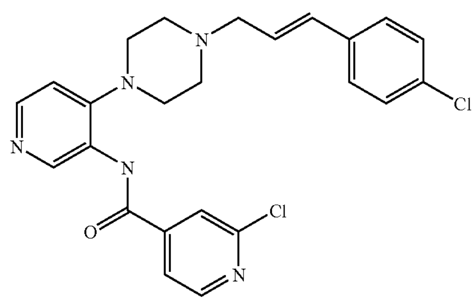 | 77-79 | 468/470 | 1.99 |

EXAMPLE 7

This Example illustrates the preparation of 2-chloro-N-(2-chloro-4-{4-[(E)-3-(4-trifluoromethoxy-phenyl)-allyl]-piperazin-1-yl}-pyrimidin-5-yl)-isonicotinamide.

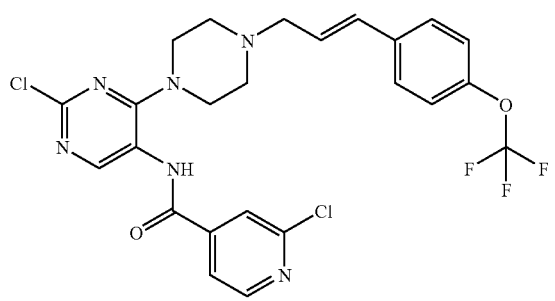

1-t-Butoxycarbonyl-piperazine (2.36 g) was condensed with 2,4-dichloro-pyrimidin-5-ylamine (2.0 g) in dimethylsulfoxide (20 ml) in the presence of triethylamine (5.3 ml) according to the method described in Example 1, Step A. 4-(5-Amino-2-chloro-pyrimidin-4-yl)-piperazine-1-carboxylic acid tert-butyl ester (3.4 g) was obtained as violet crystals. MS (ES+) 314/316 (M+H+). The title product (120 mg) was obtained from this intermediate according to the methods described in Example 1, step C and D. 2-Chloro-N-(2-chloro-4-{4-[(E)-3-(4-trifluoromethoxy-phenyl)-allyl]-piperazin-1-yl}-pyrimidin-5-yl)-isonicotinamide. M.p. 210-211° C.; $^1$H NMR (400 MHz, CDCl$_3$) 2.5 (m, 4H), 3.1 (d, J=9 Hz, 1H), 3.6 (m, 4H), 6.1 (dt, J=18, 9 Hz, 1H), 6.4 (d, J=18 Hz, 1H), 7.1 (d, J=11 Hz, 2H), 7.3 (d, J=11 Hz, 2H), 7.6 (d, J=5 Hz, 1H), 7.7 (s, 1H), 7.8 (s, 1H, NH), 8.4 (s, 1H), 8.5 (d, J=5 Hz, 1H); MS (ES+) 553/555 (M+H+).

The following compounds were prepared according to procedures analogous to those described in Example 7:

| Compound Name | Structure | M.p (° C.) | MH+ | Retention Time (min) |
|---|---|---|---|---|
| 2-chloro-N-(2-chloro-4-{4-[(E)-3-(4-chloro-phenyl)-allyl]-piperazin-1-yl}-pyrimidin-5-yl)-isonicotinamide | 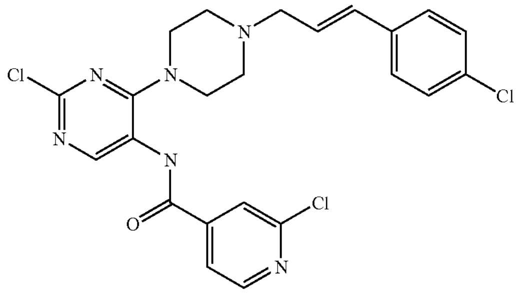 | 187-189 | 503/505 | 2.09 |
| 2-chloro-N-(2-chloro-4-{4-[(E)-3-(4-trifluoromethyl-phenyl)-allyl]-piperazin-1-yl}-pyrimidin-5-yl)-isonicotinamide | 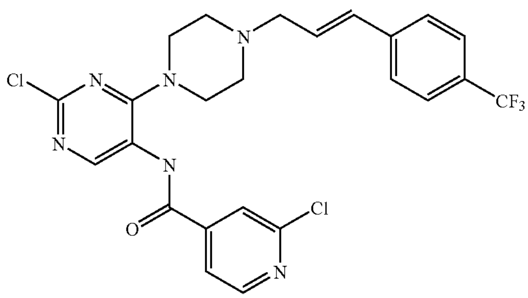 | 169-173 | 537/539 | 2.21 |

EXAMPLE 8

This Example illustrates the preparation of 2-Chloro-N-(5-{4-[(E)-3-(4-chloro-phenyl)-allyl]-piperazin-1-yl}-1,3-dimethyl-1H-pyrazol-4-yl)-isonicotinamide.

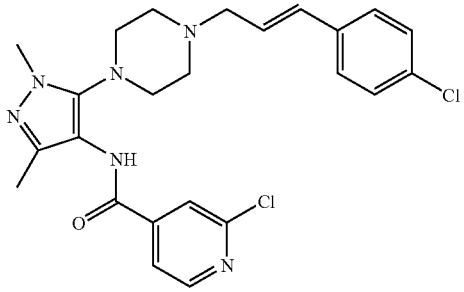

Step A: A solution of N-BOC-piperazine (4.3 g) and triethylamine (9 ml) in dimethylsulfoxide (40 ml) at 0° C. under nitrogen was treated with 4-chlorocinnamyl chloride (5 g) and the resulting solution was stirred at room temperature for 18 hours, poured into water, extracted with ethyl acetate (three times), dried over sodium sulfate and concentrated in vacuo. The residue was filtered over silica gel to afford crude 4-[(E)-3-(4-Chloro-phenyl)-allyl]-piperazine-1-carboxylic acid tert-butyl ester. This compound was dissolved in dichloromethane (30 ml) and treated with trifluoroacetic acid (10 ml) at room temperature for 18 hours. Concentration afforded 1-[(E)-3-(4-Chloro-phenyl)-allyl]-piperazine (5.8 g), which was characterised by its mass and NMR spectra. MS (ES+) 151/153 (M-piperazine), 237/239 (M+H+).

Step B: The product obtained in Step A (3.1 g) was condensed with 5-Chloro-1,3-dimethyl-4-nitro-1H-pyrazole (1.5 g) in dimethylsulfoxide (20 ml) in the presence of triethylamine (3.4 ml) as described in Example 1, Step A to afford 1-[(E)-3-(4-Chloro-phenyl)-allyl]-4-(2,5-dimethyl-4-nitro-2H-pyrazol-3-yl)-piperazine (1.82 g) as a brown solid. $^1$H NMR (400 MHz, CDCl$_3$) 2.4 (s, 3H), 2.6 (m, 4H), 3.2 (m, 6H), 3.7 (s, 3H), 6.3 (dt, J=18, 9 Hz, 1H), 6.5 (d, J=18 Hz, 1H), 7.2-7.3 (m, 4H); MS (ES+) 151/153, 376/378 (M+H+).

Step C: To a solution of the product obtained in Step B (800 mg) in tetrahydrofuran (8 ml) and methanol (8 ml) at room temperature under nitrogen was added tin(II)chloride monohydrate (2.9 g) and sodium acetate trihydrate (3.5 g). The resulting mixture was stirred at room temperature for 34 hours. The reaction mixture was partitioned between 1M sodium hydroxide and ethyl acetate, stirred for 10 min, the organic layer was separated, dried over sodium sulfate and concentrated. 1-[(E)-3-(4-Chlorophenyl)-allyl]-4-(2,5-dimethyl-4-amino-2H-pyrazol-3-yl)-piperazine (510 mg) was obtained as a red solid. $^1$H NMR (400 MHz, CDCl$_3$) 2.3 (s, 3H), 2.8 (m, 4H), 3.3 (m, 4H), 3.4 (d, J=9 Hz, 2H), 3.8 (s, 3H), 6.4 (dt, J=18, 9 Hz, 1H), 6.7 (d, J=18 Hz, 1H), 7.3-7.4 (m, 4H); MS (ES+) 151/153 (cinnamyl), 196 (M-cinnamyl), 346/348 (M+H+).

Step D: triethylamine (0.46 ml) was added to a stirred solution of the compound obtained in Step C (250 mg) in dichloromethane (10 ml); the solution was cooled to 0° C. and 2-chloro-isonicotinoyl chloride (250 mg) was added. The resulting mixture was stirred at room temperature for 12 hours, poured into water, extracted two times with dichloromethane, the combined organic layers were dried over sodium sulfate and concentrated in vacuo. The residue was subjected to silica gel chromatography (ethyl acetate: ethanol 9:5) to afford the title compound (158 mg). M.p. 85-88° C.; $^1$H NMR (400 MHz, CDCl$_3$) 2.0 (s, 3H), 2.52

(br s, 4H), 3.05 (t, J=4.8 Hz, 4H), 3.1 (d, J=6.8 Hz, 2H), 3.58 (s, 3H), 6.13 (dt, J=15.6, 6.8 Hz, 1H), 6.40 (d, J=15.6 Hz, 1H), 7.20 (s, 4H), 7.55 (d, J=5.2 Hz, 1H), 7.69 (s, 1H), 8.49 (d, J=5.2 Hz, 1H); Retention Time LCMS 2.26 min; MS (ES+) 485/487 (M+H$^+$).

The following compounds were prepared according to procedures analogous to those described in Example 8:

| Compound Name | Structure | M.p (° C.) | MH$^+$ | Retention Time (min) |
| --- | --- | --- | --- | --- |
| 2-Chloro-N-(2-{4-[(E)-3-(4-chloro-phenyl)-allyl]-piperazin-1-yl}-6-methoxy-pyridin-3-yl)-isonicotinamide | 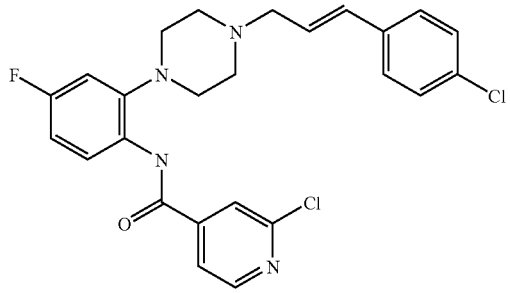 | 65-69 | 498/500 | 2.39 |

EXAMPLE 9

This Example illustrates the preparation of 2-Chloro-N-(2-{4-[(E)-3-(4-chloro-phenyl)-allyl]-2-oxo-piperazin-1-yl}-4-fluoro-phenyl)-isonicotinamide.

Step A: Piperazinone was prepared according to the method described in U.S. Pat. No. 6,433,134: ethyl chloroformate (10 g) in ethanol (50 ml) was added dropwise to a solution of ethylene diamine (32.85 ml) in ethanol (150 ml) at room temperature under nitrogen. The resulting solution was stirred at room temperature for 48 hrs, then treated dropwise over 30 min with a freshly prepared solution of sodium ethanolate in ethanol (prepared from 1.9 g sodium and 90 ml ethanol). The solution was stirred at room temperature for 2 hours, filtered on Hyflo (rinsed with ethanol), then the solvent and the excess diamine were removed in vacuo. The oily residue was refluxed in toluene (400 ml) for 3 hours, the toluene layer decanted and separated from the remaining oil; the toluene layer was kept at 0° C. overnight and the solid collected by filtration to afford piperazinone (3.6 g). M.p. 108-109° C.

Step B: piperazinone (3.6 g) was dissolved in acetonitrile (100 ml) then treated with diisopropylethylamine (9 ml) and 4-chlorocinnamyl chloride (6.7 g). The resulting reaction mixture was stirred at room temperature under nitrogen for 48 hours. The white precipitate was collected by filtration, washed with cold acetonitrile and dried under vacuum (white solid, 4.35 g). The filtrate was concentrated in vacuo and the residue crystallized from acetonitrile (white crystals, 1.4 g). M.p. 129-130° C. Both fractions showed satisfactory analytical data: N-4-[(E)-3-(4-chloro-phenyl)-allyl]-piperazin-2-one. $^1$H NMR (400 MHz, CDCl$_3$) 2.63 (t, J=5 Hz, 2H), 3.12 (s, 2H), 3.15 (d, J=7 Hz, 2H), 3.32 (m, 2H), 6.1 (dt, J=18, 9 Hz, 1H), 6.5 (d, J=18 Hz, 1H), 7.2-7.3 (m, 4H).

Step C: To a solution of the product obtained in Step B (2.51 g) in dimethylformamide (50 ml) at room temperature under nitrogen was added potassium carbonate (3.45 g) and 2,4-difluoronitrobenzene (1.59 g). The resulting mixture was stirred at 100° C. for 24 hours. Potassium carbonate (1.4 g) and 2,4-difluoronitrobenzene (1.4 g) were added again and the resulting mixture stirred at 110° C. for 48 hours. The reaction mixture was cooled to room temperature, poured into water, extracted three times with ethyl acetate; the combined organic layers were washed with brine, dried (Na$_2$SO$_4$) and concentrated in vacuo. Column chromatography (cyclohexane/ethyl acetate 6:4) afforded 4-[(E)-3-(4-chloro-phenyl)-allyl]-1-(5-fluoro-2-nitro-phenyl)-piperazin-2-one (1.9 g) as a brown solid. M.p. 57° C.; MS (ES+) 151/153 (cinnamyl), 390/392 (M+H$^+$).

Step D: Raney nickel (50% slurry in water, 200 mg) was added to a solution of the compound obtained in Step C (389 mg) in ethanol (10 ml); hydrazine hydrate (0.5 ml) was added and the reaction mixture was stirred at room temperature until gas evolution ceased (1 hour). The reaction mixture was filtered over Hyflo, the solvent removed in vacuo and the residue purified by column chromatography (2.5% methanol in ethyl acetate) to afford 1-(2-Amino-5-fluoro-phenyl)-4-[(E)-3-(4-chloro-phenyl)-allyl]-piperazin-2-one (162 mg). Retention Time LCMS 2.81 min; MS (ES+) 360/362 (M+H$^+$).

Step E: triethylamine (0.14 ml) was added to a stirred solution of the compound obtained in Step D (140 mg) in dichloromethane (10 ml); the solution was cooled to 0° C. and 2-chloro-isonicotinoyl chloride (200 mg) was added. The resulting mixture was stirred at room temperature for 3 hours, poured into water, extracted two times with dichloromethane, the combined organic layers were dried over sodium sulfate and concentrated in vacuo. The residue was subjected to silica gel chromatography (ethyl acetate:cyclohexane 1:1) to afford the title compound as a white powder (130 mg). M.p. 75-77° C.; Retention Time LCMS 3.46 min; MS (ES+) 150/152, 499/501 (M+H+).

EXAMPLE 10

This Example illustrates the preparation of 2-chloro-N-(2-{4-[(E)-3-(4-chloro-phenyl)-allyl]-piperazin-1-yl}-4,6-dichloro-phenyl)-isonicotinamide.

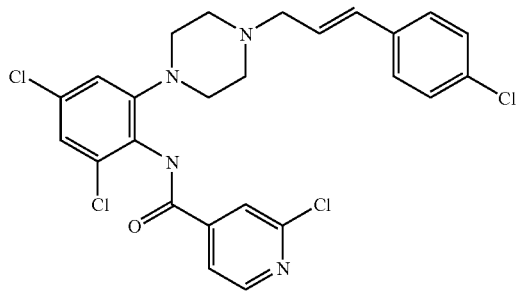

Step A: A solution of 1,3,5-trichloronitrobenzene (800 mg) and 1-t-butoxycarbonyl-piperazine (790 mg) in toluene (20 ml) was stirred at 80° C. under $N_2$ for 15 hours. The reaction mixture was cooled to room temperature, partitioned between water and ethyl acetate, the organic layer was dried ($Na_2SO_4$) and concentrated in vacuo. The residue was subjected to silica gel chromatography (cyclohexane:ethyl acetate 8:2) to afford 4-(3,5-dichloro-2-nitrophenyl)-piperazine-1-carboxylic acid tert-butyl ester (0.37 g). $^1$H NMR (400 MHz, CDCl$_3$) 1.5 (s, 9H), 2.9 (m, 4H), 3.5 (m, 4H), 7.0 (d, J=2 Hz, 1H), 7.16 (d, J=2 Hz, 1H); Retention Time HPLC 2.33 min; MS (ES+) 276/278 (M-BOC), 317/319 (M-isoprene).

Step B: The product obtained in Step A (200 mg) was reduced with tin chloride then acylated with 2-chloroisonicotinoyl chloride as described in example 8, step C and D to afford 4-(2-[(2-Chloro-pyridine-4-carbonyl)-amino]-3,5-dichloro-phenyl)-piperazine-1-carboxylic acid tert-butyl ester (1.04 g). Retention Time HPLC 2.05 min; MS (ES+) 431/433, 485/487/489 (MH+).

Step C: A solution of the compound obtained in Step C (0.08 g) in dichloromethane (1 ml) was treated with trifluoroacetic acid (0.1 ml) for 24 hours at room temperature. The reaction mixture was concentrated in vacuo. The residue was dissolved in acetonitrile (1 ml), diisopropylethylamine (0.15 ml) and 4-chlorocinnamyl chloride (0.05 g) were added. The solution was stirred 24 hours at room temperature, the solvent was removed in vacuo and the residue was subjected to silica gel chromatography to afford the title product (66 mg) as a solid. M.p. 79-80° C.; $^1$H NMR (400 MHz, CDCl$_3$) 2.37 (m, 4H), 2.6 (m, 4H), 3.1 (d, J=9 Hz, 2H), 6.2 (dt, J=18, 9 Hz, 1H), 6.5 (d, J=18 Hz, 1H), 6.9 (d, J=2 Hz, 1H), 7.2-7.3 (m, 5H), 7.5 (s, 1H, NH), 7.6 (d, J=4.5 Hz, 1H), 7.7 (s, 1H), 8.5 (d, J=5.5 Hz, 1H); Retention Time HPLC 1.44 min; MS (ES+) 535/537/539 (M+H+).

The following compounds were prepared according to procedures analogous to those described in Example 10:

| Compound Name | Structure | M.p (° C.) | MH+ | Retention Time (min) |
|---|---|---|---|---|
| 2-chloro-N-(2-{4-[(E)-3-(4-chloro-phenyl)-allyl]-piperazin-1-yl}-4,5-difluoro-phenyl)-isonicotinamide | 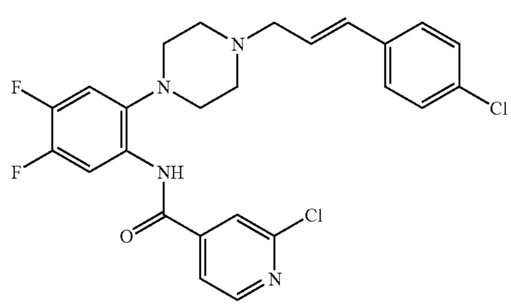 | 55-58 | 503-505 | 1.62 |
| 2-chloro-N-(2-{4-[(E)-3-(4-chloro-phenyl)-allyl]-piperazin-1-yl}-4-chloro-5-fluoro-phenyl)-isonicotinamide | 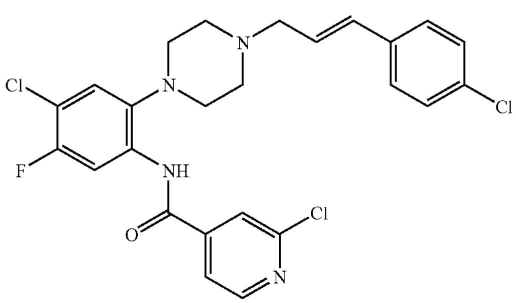 | 122-123 | 519 | 1.52 |

-continued

| Compound Name | Structure | M.p (° C.) | MH+ | Retention Time (min) |
|---|---|---|---|---|
| 2-chloro-N-(2-{4-[(E)-3-(4-chloro-phenyl)-allyl]-piperazin-1-yl}-4,5-dichloro-phenyl)-isonicotinamide | 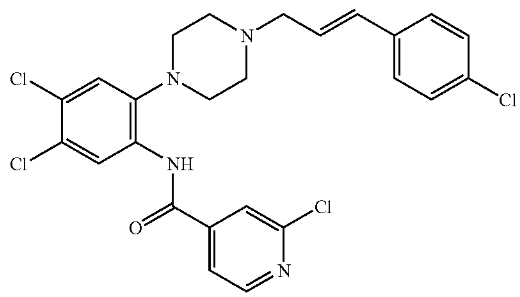 | 154-155 | 535/537/539 | 1.57 |
| 2-chloro-N-(2-{4-[(E)-3-(4-chloro-phenyl)-allyl]-piperazin-1-yl}-4,5,6-trifluoro-phenyl)-isonicotinamide | 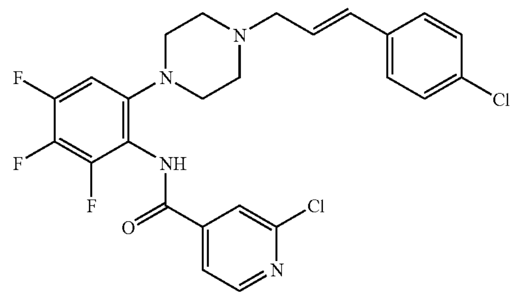 | 94-96 | 521/523 | 1.39 |
| 2-chloro-N-(2-{4-[(E)-3-(4-chloro-phenyl)-allyl]-piperazin-1-yl}-4,5-difluoro-phenyl)-isonicotinamide | 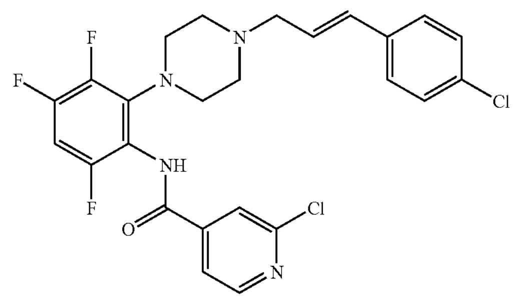 | 80-82 | 521/523 | 1.36 |

EXAMPLE 11

This Example illustrates the pesticidal/insecticidal properties of compounds of formula (I).

Test against were performed as follows:

*Spodoptera littoralis* (Egyptian Cotton Leafworm)

Cotton leaf discs were placed on agar in a 24-well microtiter plate and sprayed with test solutions at an application rate of 200 ppm. After drying, the leaf discs were infested with 5 $L_1$ larvae. The samples were checked for mortality, repellent effect, feeding behaviour, and growth regulation 3 days after treatment (DAT). The following compounds gave at least 80% control of *Spodoptera littoralis*:

I-3, I-26, I-29, I-30, I-49, I-52, I-53, I-75, I-417, I-532, I-578, I-785, I-854, I-877, II-49, III-49, V-49, XII-49, XIV-26, XV-26, XXIV-2, XXIV-46, XXIV-90, XXIV-93, XXIV-94, XXV-26 and XXV-49.

*Heliothis virescens* (Tobacco Budworm):

Eggs (0-24 h old) were placed in 24-well microtiter plate on artificial diet and treated with test solutions at an application rate of 200 ppm by pipetting. After an incubation period of 4 days, samples were checked for egg mortality, larval mortality, and growth regulation. The following compounds gave at least 80% control of *Heliothis virescen*:

I-3, I-6, I-7, I-26, I-29, I-30, I-47, I-49, I-52, I-53, I-72, I-75, I-417, I-532, I-578, I-785, I-854, I-877, III-49, V-49, XII-49, XIV-26, XIV-49, XV-26, XVI-26, XVII-26, XXIV-2, XXIV-46, XXIV-90, XXIV-93, XXIV-94, XXV-2, XXV-26, XXV-49 and XXV-68.

*Plutella xylostella* (Diamond Back Moth):

24-well microtiter plate (MTP) with artificial diet was treated with test solutions at an application rate of 18.2 ppm by pipetting. After drying, the MTP's were infested with larvae (L2)(10-15 per well). After an incubation period of 5 days, samples were checked for larval mortality, antifeedant and growth regulation. The following compounds gave at least 80% control of *Plutella xylostella*:

I-26, I-29, I-30, I-49, I-417, I-532, I-578, I-785, I-854, I-877, V-49, IX-49, XII-49, XIV-26, XV-26, XXIV-46, XXIV-90 and XXV-26.

*Aedes aegypti* (Yellow Fever Mosquito):

10-15 *Aedes* larvae (L2) together with a nutrition mixture are placed in 96-well microtiter plates. Test solutions at an application rate of 2 ppm are pipetted into the wells. 2 days later, insects were checked for mortality and growth inhibition. The following compounds gave at least 80% control of *Aedes aegypti*

I-3, I-26, I-29, I-30, I-49, I-52, I-53, I-72, I-75, I-76, III-49, III-118, XIV-26, XV-26, XXIV-2, XXIV-46, XXIV-90, XXIV-93, XXIV-94 and XXV-68.

*Myzus persicae* (Green Peach Aphid):

Sunflower leaf discs were placed on agar in a 24-well microtiter plate and sprayed with test solutions at an application rate of 200 ppm. After drying, the leaf discs were infested with an aphid population of mixed ages. After an incubation period of 6 DAT, samples were checked for mortality. The following compounds gave at least 80% control of *Myzus persicae*:

I-3, I-26, I-29, I-26, I-29, I-30, I-49, I-52, I-53, I-72, I-75, III-49, V-49, XXIV-46, XXIV-90 and XXIV-94.

The invention claimed is
1. A method of combating and controlling insects, acarines, nematodes or molluscs which comprises applying to a pest, to a locus of a pest, or to a plant susceptible to attack by a pest an insecticidally, acaricidally, nematicidally or molluscicidally effective amount of a compound of formula I

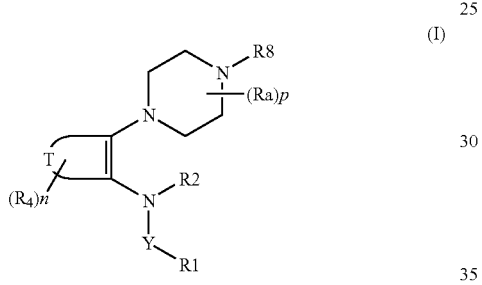

(I)

Y is a single bond, C=O, C=S or $S(O)_m$ where m is 0, 1 or 2;
the ring

is a benzene, pyridine, pyrimidine, pyrazine, pyridazine, triazine, furan, thiophene, pyrrole, imidazole, pyrazole, oxazole, thiazole, isoxazole, isothiazole, [1,2,3]triazole, [1,2,3]oxadiazole or [1,2,3]thiadiazole;

$R^1$ is
$C_{1-6}$ alkyl;
$C_{1-6}$ haloalkyl;
$C_{1-6}$ alkoxy($C_{1-6}$)alkyl;
heteroaryl($C_{1-3}$)alkyl, wherein the heteroaryl group may be optionally substituted by halo, nitro, cyano, $C_{1-6}$ alkyl, $C_{1-6}$ haloalkyl, $C_{1-6}$ alkoxy, $C_{1-6}$ haloalkoxy, $C_{1-6}$ alkylsulfonyl, $C_{1-6}$ alkoxycarbonyl, or two adjacent positions on the heteroaryl system may be cyclised to form a 5, 6 or 7 membered carbocyclic or heterocyclic ring, itself optionally substituted with halogen;
phenyl($C_{1-3}$)alkyl, wherein the phenyl group may be optionally substituted by halogen, $C_{1-4}$ alkyl, $C_{1-4}$ alkoxy, $C_{1-4}$ haloalkyl, $C_{1-4}$ haloalkoxy, CN, $NO_2$, aryl, heteroaryl, amino, dialkylamino, $C_{1-6}$ alkylsulfonyl, $C_{1-6}$ alkoxycarbonyl, or two adjacent positions on the phenyl ring may be cyclised to form a 5, 6 or 7 membered carbocyclic or heterocyclic ring, itself optionally substituted with halogen;
phenyl, wherein the phenyl may be optionally substituted by halogen, $C_{1-4}$ alkyl, $C_{1-4}$ alkoxy, $C_{1-4}$ haloalkyl, $C_{1-4}$ haloalkoxy, CN, $NO_2$, aryl, heteroaryl, amino, dialkylamino, $C_{1-6}$ alkylsulfonyl, $C_{1-6}$ alkoxycarbonyl, or two adjacent positions on the phenyl ring may be cyclised to form a 5, 6 or 7 membered carbocyclic or heterocyclic ring, itself optionally substituted with halogen;
heteroaryl, wherein the heteroaryl may be optionally substituted by halo, nitro, cyano, $C_{1-6}$ alkyl, $C_{1-6}$ haloalkyl, $C_{1-6}$ alkoxy, $C_{1-6}$ haloalkoxy, $C_{1-6}$ alkylsulfonyl, $C_{1-6}$ alkoxycarbonyl, or two adjacent positions on the heteroaryl system may be cyclised to form a 5, 6 or 7 membered carbocyclic or heterocyclic ring, itself optionally substituted with halogen;
$C_{1-6}$ alkoxy;
$C_{1-6}$ haloalkoxy;
$C_{2-6}$ alkenyl;
heterocyclyl, wherein the heterocyclyl may be optionally substituted by halo, cyano, $C_{1-6}$ alkyl, $C_{1-6}$ haloalkyl, $C_{1-6}$ alkoxy or $C_{1-6}$ haloalkoxy;
$C_{1-6}$alkylthio;
$C_{1-6}$ haloalkylthio;
or $NR^{13}R^{14}$, where $R^{13}$ and $R^{14}$ are independently hydrogen, $C_{1-6}$ alkyl or $C_{1-6}$ haloalkyl;
$C_{1-6}$ alkoxy($C_{1-6}$)alkyl;
$C_{2-6}$ alkylcarbonyl;
phenylcarbonyl, wherein the phenyl may be optionally substituted by halogen, $C_{1-4}$ alkyl, $C_{1-4}$ alkoxy, $C_{1-4}$ haloalkyl, $C_{1-4}$ haloalkoxy, CN, $NO_2$, aryl, heteroaryl, amino or dialkylamino; or
heteroaryl($C_{1-3}$)alkyl, wherein the heteroaryl group may be optionally substituted by halo, nitro, cyano, $C_{1-6}$ alkyl, $C_{1-6}$ haloalkyl, $C_{1-6}$ alkoxy, $C_{1-6}$ haloalkoxy, $C_{1-6}$ alkylsulfonyl, $C_{1-6}$ alkysulfinyl, $C_{1-6}$ alkylthio, $C_{1-6}$ alkoxycarbonyl, $C_{1-6}$ alkylcarbonylamino, arylcarbon, or two adjacent positions on the heteroaryl system may be cyclised to form a 5, 6 or 7 membered carbocyclic or heterocyclic ring, itself optionally substituted with halogen;
$R^2$ is hydrogen;
hydroxy,
$C_{1-6}$ alkyl; or
$C_{1-6}$haloalkyl;
each $R^4$ is independently halogen;
cyano;
$C_{1-8}$ alkyl;
$C_{1-8}$ haloalkyl;
$C_{1-8}$ cyanoalkyl;
$C_{1-6}$ alkoxy($C_{1-6}$)alkyl;
$C_{2-6}$ alkynyl;
trimethylsilyl($C_{2-6}$)alkynyl;
$C_{1-6}$ alkoxycarbonyl;
$(C_{3-7})$cycloalkyl;
$C_{1-3}$alkyl($C_{3-7}$)cycloalkyl;
phenyl, wherein the phenyl may be optionally substituted by halogen, $C_{1-4}$ alkyl, $C_{1-4}$ alkoxy, $C_{1-4}$ haloalkyl, $C_{1-4}$ haloalkoxy, CN, $NO_2$, aryl, heteroaryl, amino or dialklamino;
heterocyclyl, wherein the heterocyclyl may be optionally substituted by halo, nitro, cyano, $C_{1-6}$ alkyl, $C_{1-6}$ haloalkyl, $C_{1-6}$ alkoxy or $C_{1-6}$ haloalkoxy;
$C_{1-8}$ alkoxy;
$C_{1-6}$ haloalkoxy;

phenoxy, wherein the phenoxy may be optionally substituted by halogen, $C_{1-4}$ alkyl, $C_{1-4}$ alkoxy, $C_{1-4}$ haloalkyl, $C_{1-4}$ haloalkoxy, CN, NO$_2$, aryl, heteroaryl, amino or dialkylamino;

heteroaryloxy, wherein the heteroaryloxy may be optionally substituted by halo, nitro, cyano, $C_{1-3}$ alkyl, $C_{1-3}$ haloalkyl, $C_{1-3}$ alkoxoy or $C_{1-3}$ haloalkoxy;

di($C_{1-8}$)alkylamino;

or 2 adjacent $R^4$ groups together with the carbon atoms to which they are attached form a 4, 5, 6 or 7 membered carbocyclic or heterocyclic ring which may be optionally substituted by halogen;

n is 0, 1, 2, or 3;

$R^8$ is phenyl($C_{1-4}$)alkyl, wherein the phenyl group may be optionally substituted by halogen, $C_{1-4}$ alkyl, $C_{1-4}$ alkoxy, $C_{1-4}$ haloalkyl, $C_{1-4}$ haloalkoxy, CN, NO$_2$, aryl, heteroaryl, amino or dialkylamino;

heteroaryl($C_{1-6}$)alkyl, wherein the heteroaryl group may be optionally substituted by halogen, $C_{1-4}$ alkyl, $C_{1-4}$ alkoxy, $C_{1-4}$ haloalkyl, $C_{1-4}$ haloalkoxy, CN, NO$_2$, aryl, heteroaryl, amino or dialkylamino;

phenyl($C_{2-6}$)alkenyl, wherein the phenyl group may be optionally substituted by halogen, $C_{1-4}$ alkyl, $C_{1-4}$ alkoxy, $C_{1-4}$ haloalkyl, $C_{1-4}$ haloalkoxy, CN, NO$_2$, aryl, heteroaryl, amino or dialkylamino; heteroaryl ($C_{2-6}$)alkenyl, wherein the heteroaryl group may be optionally substituted by halogen, $C_{1-4}$ alkyl, $C_{1-4}$ alkoxy, $C_{1-4}$ haloalkyl, $C_{1-4}$ haloalkoxy, CN, NO$_2$, aryl, heteroaryl, amino or dialkylamino;

phenyl($C_{2-6}$)alkynyl, wherein the phenyl group may be optionally substituted by halogen, $C_{1-4}$ alkyl, $C_{1-4}$ alkoxy, $C_{1-4}$ haloalkyl, $C_{1-4}$ haloalkoxy, CN, NO$_2$, aryl, heteroaryl, amino or dialkylamino; or —C($R^{51}$)($R^{52}$)—[$CR^{53}$=$CR^{54}$]z-$R^{55}$ where z is 1 or 2:
$R^{51}$ and $R^{52}$ are each independently H, halo or $C_{1-2}$ alkyl;
$R^{53}$ and $R^{54}$ are each independently H, halogen, $C_{1-4}$ alkyl or $C_{1-4}$ haloalkyl; and
$R^{55}$ is optionally substituted aryl or optionally substituted heteroaryl;

each Ra is independently halogen;
hydroxy;
cyano;
optionally substituted $C_{1-8}$ alkyl;
optionally substituted $C_{2-6}$ alkenyl;
optionally substituted $C_{2-6}$ alkynyl;
optionally substituted alkoxycarbonyl;
optionally substituted alkylcarbonyl;
optionally substituted alkylaminocarbonyl;
optionally substituted dialkylaminocarbonyl;
optionally substituted $C_{3-7}$ cycloalkyl;
optionally substituted aryl;
optionally substituted heteroaryl;
optionally substituted heterocyclyl;
optionally substituted alkoxy;
optionally substituted aryloxy;
optionally substituted heteroaryloxy;
optionally substituted alkylthio;
optionally substituted arylthio; or $R^{23}R^{24}$N where $R^{23}$ and $R^{24}$ are, independently, hydrogen, $C_{1-8}$ alkyl, $C_{3-7}$ cycloalkyl, $C_{3-6}$ alkenyl, $C_{3-6}$ alkynyl, $C_{3-7}$ cycloalkyl($C_{1-4}$)alkyl, $C_{2-6}$ haloalkyl, $C_{1-6}$ alkoxy ($C_{1-6}$)alkyl, $C_{1-6}$ alkoxycarbonyl or $R^{23}$ and $R^{24}$ together with the N atom to which they are attached form a five, six or seven-membered heterocyclic ring which may contain one or two further heteroatoms selected from O, N or S and which may be optionally substituted by one or two $C_{1-6}$ alkyl groups, or two Ra groups attached to the same carbon atom are =O, =S, =NRb, or =CRcRd, where each of Rb, Rc and Rd are independently hydrogen or optionally substituted alkyl;

p is 0, 1, 2, 3 or 4 or salts or N-oxides thereof.

2. A method according to claim 1 wherein the ring is a benzene or pyridine ring.

3. A method according to claim 1 wherein Y is a single bond, C=O or C=S.

4. A method according to claim 1 wherein $R^1$ is $C_{1-6}$ alkyl;
$C_{1-6}$ haloalkyl;
heteroaryl($C_{1-3}$)alkyl, wherein the heteroaryl group may be optionally substituted by halo, cyano, $C_{1-6}$ alkyl, $C_{1-6}$ haloalkyl and wherein the heteroaryl group is a thiazole, pyridine, pyrimidine, pyrazine or pyridazine ring;
heteroaryl, (wherein the heteroaryl may be optionally substituted by halo, cyano, $C_{1-6}$ alkyl, $C_{1-6}$ haloalkyl and wherein the heteroaryl group is a pyridine, pyrimidine, 2,1,3-benzoxadiazole, pyrazine or pyridazine ring;
$C_{1-6}$ alkoxy, $C_{1-6}$alkoxy($C_{1-6}$)alkyl;
$C_{1-6}$ alkylamino;
$C_{1-6}$ alkyoxy($C_{1-6}$)alkylamino; or
heteroaryl($C_{1-3}$)alkylamino, wherein the heteroaryl group may be optionally substituted by halo, cyano, $C_{1-6}$ alkyl, $C_{1-6}$ haloalkyl and wherein the heteroaryl group is a thiazole, pyridine, pyrimidine, pyrazine or pyridazine ring.

5. A method according to claim 1 wherein $R^2$ is hydrogen, $C_{1-4}$ alkyl, or $C_{1-4}$ haloalkyl.

6. A method according to claim 1 wherein each $R^4$ is independently
halogen;
cyano;
$C_{1-8}$ alkyl;
$C_{1-8}$ haloalkyl;
$C_{1-8}$ cyanoalkyl;
$C_{1-6}$ alkoxy($C_{1-6}$)alkyl;
$C_{2-6}$ alkynyl,
heterocyclyl, wherein the heterocyclyl group is optionally substituted by $C_{1-6}$ alkyl;
$C_{1-8}$ alkoxy;
$C_{1-6}$ haloalkoxy;
phenoxy, wherein the phenoxy may be optionally substituted by halo, cyano, $C_{1-3}$ alkyl or $C_{1-3}$ haloalkyl;
heteroaryloxy, wherein the heteroaryloxy may be optionally substituted by halo, cyano, $C_{1-3}$ alkyl or $C_{1-3}$ haloalkyl;
di($C_{1-8}$)alkylamino; or
2 adjacent groups $R^4$ together with the carbon atoms to which they are attached form a 4, 5, 6 or 7 membered carbocylic or heterocyclic ring which may be optionally substituted by halogen; and
n is 0, 1, 2 or 3.

7. A method according to claim 1 wherein $R^8$ is
—C($R^{51}$)($R^{52}$)—[$CR^{53}$=$CR^{54}$]z-$R^{55}$ where z is 1 or 2;
$R^{51}$ and $R^{52}$ are each independently H, halo or $C_{1-2}$ alkyl;
$R^{53}$ and $R^{54}$ are each independently H, halogen, $C_{1-4}$ alkyl or $C_{1-4}$ haloalkyl; and
$R^{55}$ is phenyl substituted by halogen, $C_{1-4}$ alkyl, $C_{1-4}$ alkoxy, $C_{1-4}$ haloalkyl, $C_{1-4}$ haloalkoxy, CN, NO$_2$, aryl, heteroaryl, amino or dialkylamino; or $R^{55}$ is heteroaryl substituted by halogen, $C_{1-4}$ alkyl, $C_{1-4}$ alkoxy, $C_{1-4}$ haloalkyl, $C_{1-4}$ haloalkoxy, CN, $NO_2$, aryl, heteroaryl, amino or dialkylamino.

8. A method according to claim 1 wherein Ra is independently halo;
cyano;
$C_{1-3}$ alkyl;
hydroxy; or
two Ra groups together with the carbon atom to which they are attached form =O, =S, =NRb, or =CRcRd where each of Rb, Rc and Rd are independently hydrogen or optionally substituted alkyl; and
p is 0, 1 or 2.

9. A method according to claim 5 wherein $R^2$ is hydrogen or $C_{1-4}$ alkyl.

10. A method according to claim 6 wherein each $R^4$ is independently fluoro;
chloro;
bromo;
cyano;
$C_{1-4}$ alkyl;
$C_{1-4}$ haloalkyl;
$C_{1-4}$ cyanoalkyl; or
$C_{1-3}$ alkoxy($C_{1-3}$)alkyl; and
n is 0, 1, 2 or 3.

11. A method according to claim 7 wherein z is 1.

12. A method according to claim 8 wherein p is 0.

13. A method according to claim 1 wherein
Y is a single bond, C=O or C=S;
the ring

is a benzene or pyridine ring;
$R^1$ is $C_{1-6}$ alkyl;
$C_{1-6}$ haloalkyl;
heteroaryl($C_{1-3}$)alkyl, wherein the heteroaryl group may be optionally substituted by halo, cyano, $C_{1-6}$ alkyl, $C_{1-6}$ haloalkyl and where the heteroaryl group is a thiazole, pyridine, pyrimidine, pyrazine or pyridazine ring;
heteroaryl, wherein the heteroaryl may be optionally substituted by halo, cyano, $C_{1-6}$ alkyl, $C_{1-6}$ haloalkyl and where the heteroaryl group is a pyridine, pyrimidine, 2,1,3-benzoxadiazole, pyrazine or pyridazine ring;
$C_{1-6}$ alkoxy;
$C_{1-6}$ alkoxy($C_{1-6}$)alkyl;
$C_{1-6}$ alkylamino;
$C_{1-6}$ alkyoxy($C_{1-6}$)alkylamino; or
heteroaryl($C_{1-3}$)alkylamino, wherein the heteroaryl group may be optionally substituted by halo, cyano, $C_{1-6}$ alkyl, $C_{1-6}$ haloalkyl and where the heteroaryl group is a thiazole, pyridine, pyrimidine, pyrazine or pyridazine ring;
$R^2$ is hydrogen or $C_{1-4}$ alkyl;
each $R^4$ is independently fluoro;
chloro;
bromo;
cyano;
$C_{1-4}$ alkyl;
$C_{1-4}$ haloalkyl;
$C_{1-4}$ cyanoalkyl; or
$C_{1-3}$ alkoxy($C_{1-3}$)alkyl;
n is 0, 1, 2 or 3;
$R^8$ is —C($R^{51}$)($R^{52}$)—[$CR^{53}$=$CR^{54}$]z-$R^{55}$ where z is 1 or 2;
$R^{51}$ and $R^{52}$ are each independently hydrogen or $C_{1-2}$ alkyl;
$R^{53}$ and $R^{54}$ are each independently hydrogen, halogen, $C_{1-4}$ alkyl or $C_{1-4}$ haloalkyl; and
$R^{55}$ is phenyl substituted by halogen, $C_{1-4}$ alkyl, $C_{1-4}$ alkoxy, $C_{1-4}$ haloalkyl, $C_{1-4}$ haloalkoxy, CN, $NO_2$, aryl, heteroaryl, amino or dialkylamino or heteroaryl substituted by halogen, $C_{1-4}$ alkyl, $C_{1-4}$ alkoxy, $C_{1-4}$ haloalkyl, $C_{1-4}$ haloalkoxy, CN, $NO_2$, aryl, heteroaryl, amino or dialkylamino;
each Ra is independently halo, cyano, $C_{1-3}$ alkyl, hydroxy or two Ra groups together with the carbon atom to which they are attached form =O, =S, =NRb, =CRcRd where Rb, Rc and Rd are independently hydrogen or optionally substituted alkyl; and
p is 0, 1 or 2.

14. A method according to claim 13 wherein z is 1.

* * * * *